(12) United States Patent
Cho et al.

(10) Patent No.: US 10,787,425 B2
(45) Date of Patent: Sep. 29, 2020

(54) THIAZOLIDINEDIONE DERIVATIVE AND USE THEREOF

(71) Applicant: INDUSTRY-ACADEMIC COOPERATION FOUNDATION CHOSUN UNIVERSITY, Gwangju (KR)

(72) Inventors: Hoon Cho, Gwangju (KR); Eunjeong Yoon, Gwangju (KR)

(73) Assignee: INDUSTRY-ACADEMIC COOPERATION FOUNDATION CHOSUN UNIVERSITY, Gwangju (KR)

(*) Notice: Subject to any disclaimer, the term of this patent is extended or adjusted under 35 U.S.C. 154(b) by 0 days.

(21) Appl. No.: 16/068,518

(22) PCT Filed: Aug. 18, 2016

(86) PCT No.: PCT/KR2016/009068
§ 371 (c)(1),
(2) Date: Jul. 6, 2018

(87) PCT Pub. No.: WO2017/119570
PCT Pub. Date: Jul. 13, 2017

(65) Prior Publication Data
US 2019/0016695 A1 Jan. 17, 2019

(30) Foreign Application Priority Data
Jan. 8, 2016 (KR) .................. 10-2016-0002809

(51) Int. Cl.
*C07D 277/34* (2006.01)
*C07D 277/36* (2006.01)
*A61P 9/10* (2006.01)
*A61P 17/14* (2006.01)
*A61P 9/12* (2006.01)
*A61P 13/12* (2006.01)
*A61P 17/02* (2006.01)
*A61P 9/04* (2006.01)
*A61P 1/04* (2006.01)

(52) U.S. Cl.
CPC .............. *C07D 277/34* (2013.01); *A61P 1/04* (2018.01); *A61P 9/04* (2018.01); *A61P 9/10* (2018.01); *A61P 9/12* (2018.01); *A61P 13/12* (2018.01); *A61P 17/02* (2018.01); *A61P 17/14* (2018.01); *C07D 277/36* (2013.01)

(58) Field of Classification Search
CPC .......................... C07D 277/34; C07D 277/36
See application file for complete search history.

(56) References Cited

U.S. PATENT DOCUMENTS

| 7,396,525 B2 | 7/2008 | Rozot et al. |
| 8,637,558 B2 | 1/2014 | Cho et al. |
| 9,216,148 B2 | 12/2015 | Chung et al. |
| 2007/0071699 A1 | 3/2007 | Boulle |

FOREIGN PATENT DOCUMENTS

| IN | 2013MU02615 A | * | 8/2014 |
| KR | 1020110107358 A | | 9/2011 |
| KR | 1020120091650 A | | 8/2012 |
| KR | 1020130103945 A | | 9/2013 |
| WO | 01/02377 A1 | | 1/2001 |
| WO | 2011/063602 A1 | | 6/2011 |

OTHER PUBLICATIONS

Chemical Abstracts Registry No. 292172-34-0, indexed in the Registry file on STN CAS Online on Oct. 3, 2000. (Year: 2000).*
PubChem CID 1350342, National Center for Biotechnology Information. PubChem Database. CID=1350342, https://pubchem.ncbi.nlm.nih.gov/compound/1350342 (accessed on Jun. 5, 2019), create date Jul. 11, 2005. (Year: 2005).*
PubChem CID 9801542 {National Center for Biotechnology Information. PubChem Database. CID=9801542, https://pubchem.ncbi.nlm.nih.gov/compound/9801542 (accessed on Jun. 5, 2019), create date Oct. 25, 2006. (Year: 2006).*
Strittmatter et al., ACS Chemical Biology, 2011, 6(4), pp. 314-319. (Year: 2011).*
Chemical Abstracts Registry No. 895044-93-6, indexed in the Registry file on STN CAS Online Jul. 23, 2006. (Year: 2006).*
Chemical Abstracts Registry No. 938740-39-7, indexed in the Registry file on STN CAS Online Jun. 24, 2007. (Year: 2007).*
Miles et al., FEMS Microbiology Letters, 1992, 90(3), pp. 283-287. (Year: 1992).*
Agrawal et al., Chemical Biology & Drug Design, Feb. 2015, 85(2), pp. 172-180. (Year: 2015).*
STN Express: "Chemical Abstract Compound", RN: 893194-85-9 (Jul. 16, 2006), RN: 893031-86-2 (Jul. 16, 2006) RN: 331987-96-3 (Apr. 20, 2001), RN: 292172-34-0 (Oct. 3, 2000) 2 pages.
Yan Cheng, et al; "Cyclooxygenases, microsomal prostaglandin E synthase-1, and cardiovascular function", The Journal of Clinical Investigation, May 2006;116(5): 1391-1399; Epub Apr. 13, 20066.

(Continued)

*Primary Examiner* — Laura L Stockton

(57) ABSTRACT

Provided are a novel compound represented by any one of Formulae 1a and 1b and use thereof. Provided are novel thiazolidinedione derivatives represented by any one of Formulae 1a and 1b and pharmaceutical compositions containing the same.

15 Claims, 6 Drawing Sheets

(56) References Cited

OTHER PUBLICATIONS

Kyu-Sup Cho, et al; "Prostaglandin E2 and Transforming Growth Factor-β Play a Critical Role in Suppression of Allergic Airway Inflammation by Adipose-Derived Stem Cells", PLoS One, Jul. 15, 2015;10(7): 16 pages.
Dubok Choi, et al; "Control of the intracellular levels of prostaglandin $E_2$ through inhibition of the 15-hydroxyprostaglandin dehydrogenase for wound healing", Journal of Bioorganic & Medicinal Chemistry, vol. 21, pp. 4477-4484, Available online Jun. 4, 2013.
Laurent Colombe, et al; "Prostaglandin metabolism in human hair follicle", Exp Dermatol, Sep. 2007;16(9): 762-9.
Charles Mark Ensor, et al; "15-Hydroxyprostaglandin dehydrogenase", J. Lipid Mediators Cell Signalling Oct. 1, 1995, 12(2-3):313-319.
Wolfram Goessling, et al; "Prostaglandin E2 Enhances Human Cord Blood Stem Cell Xenotransplants and Shows Long-Term Safety in Preclinical Nonhuman Primate Transplant Models", Cell Stem Cell 8, 445-458, Apr. 8, 2011.
Chuan-Ming Hao, et al; "Physiological Regulation of Prostaglandins in the Kidney", Annu. Rev. Physiol. vol. 70, Mar. 17, 2008, pp. 357-377, First Published online as a Review in Advance on Nov. 7, 2007.
Hiroshi Kawaguchi, MD*, et al; "The Role of Prostaglandins in the Regulation of Bone Metabolism", Clinical Orthopaedics and Related Research, No. 313, pp. 36-46, Apr. 1, 1995.
John M Keith; "Selective ortho-cleavage of methoxymethyl- and 4-methoxybenzyl ethers", Tetrahedron Letters, vol. 45, Issue 13, Mar. 22, 2004, pp. 2739-2742.
Johnny Keller, et al; "Effect of local prostaglandin $E_2$ on periosteum and muscle in rabbits", Acta Orthopaedica Scandinavica, Dec. 1992, vol. 63, Issue 6, pp. 623-627; Published online Nov. 24, 2009.
Hyung-Sik Kim, et al; "Human Umbilical Cord Blood Mesenchymal Stem Cell-Derived $PGE_2$ and TFF-⊕1 Alleviate Atopic Dermatitis by Reducing Mast Cell Degranulation", Stem Cells, Apr. 2015; 33(4): 1254-66.
S. J. Konturek, et al; "Prostaglandins and Ulcer Healmg", Journal of Physiology and Pharmacology, Sep. 2005 , 56, Supp 5, 5-31.
Maria Krook, et al; "Purification and Structural Characterization of Placental $NAD^+$—Linked 15-Hydroxyprostaglandin Dehydrogenase. The Primary Structure Reveals the Enzyme to Belong to the Short-Chain Alcohol Dehydrogenase Family", Biochemistry, Jan. 1990, 29(3), pp. 738-743.
Jean Francois Michelet, et al; "Expression of $NAD^+$ dependent 15-hydroxyprostaglandin dehydrogenase and 15 protection of prostaglandins in human hair follicle", Experimental Dermatology, vol. 17, Issue 10, Oct. 2008, pp. 821-828, First published: Sep. 11, 2008.
Shuh Narumiya, et al; "Prostanoid Receptors: Structures, Properties, and Functions", Physiological Reviews, vol. 79, No. 4, Oct. 1999, pp. 1193-1226.
George A Porter, MD; "Contrast-Associated Nephropathy", The American Journal of Cardiology, vol. 64, Issue 9, pp. E22-E26, Sep. 5, 1989.
Hsin-Hsiung Tai, et al; "Structure and Function of Human $NAD^+$—Linked 15-Hydroxyprostaglandin Dehydrogenase", Eicosanoids and Other Bioactive Lipids in Cancel, Inflammaton, and Radiation Injury, 5 pp. 245-250, Part of the Advances in Experimental Medicine and Biology book series (AEMB, vol. 507) . . . Only able to provide a preview of the publication. pp. 245-246 , 2002.
Eva H.C. Tang, et al; "The role of prostaglandin E and thromboxane-prostanoid receptors in the response to prostaglandin $E_2$ in the aorta of Wistar Kyoto rats and spontaneously hypertensive rats", Cardiovascular Research, vol. 78, pp. 130-138, Online publish-ahead-of-print Dec. 18, 2007.
Min Tong, et al; "Induction of $NAD^+$—Linked 15-Hydroxyprostaglandin Dehydrogenase Expression by Androgens in Human Prostate Cancer Cells[1]", Biochemical and Biophysical Research Communications 276, Issue 1, Sep. 16, 2000; pp. 77-81.
John L. Wallace; "Prostaglandins, NSAIDs, and Gastric Mucosal Protection: Why Doesn't the Stomach Digest Itself?", Physiol Rev 88: 1547-1565, Oct. 1, 2008.
Ying Wu, et al; "Synthesis and Biological Evaluation of Novel Thiazolidinedione Analogues as 15-Hydroxyprostaglandin Dehydrogenase Inhibitors", Journal of Medicinal Chemistry, Published Jun. 8, 2011, vol. 54, pp. 5260-5264.
Korean Office Action dated Dec. 14, 2016; Appln. No. 10-2016-0002809.
Korean Notice of Allowance dated Dec. 29, 2017; Appln. No. 10-2016-002809.
The International Search Report dated Nov. 8, 2016; PCT/KR2016/009068.

* cited by examiner

| | Control | 59 | 89 | TGF-β1 |
|---|---|---|---|---|
| 0 hour |  516 μm |  485 μm |  506 μm |  540 μm |
| 24 hour |  444 μm |  133 μm |  159 μm |  189 μm |

FIG. 4

| 59 | Control | 0.5 µM | 1 µM | 3 µM | 5 µM |
|---|---|---|---|---|---|
| 0 hour | 530 µm | 579 µm | 538 µm | 601 µm | 608 µm |
| 24 hour | 421 µm | 319 µm | 250 µm | 249 µm | 191 µm |

FIG. 5

| 89 | Control | 0.5 μM | 1 μM | 3 μM | 5 μM |
|---|---|---|---|---|---|
| 0 hour | 530 μm | 583 μm | 528 μm | 582 μm | 581 μm |
| 24 hour | 421 μm | 323 μm | 277 μm | 249 μm | 212 μm |

THIAZOLIDINEDIONE DERIVATIVE AND USE THEREOF

TECHNICAL FIELD

The present disclosure relates to novel thiazolidinedione derivatives and use thereof. In particular, the present disclosure relates to novel thiazolidinedione derivatives and pharmaceutical compositions containing the same.

BACKGROUND ART

Prostaglandin is a 20 carbon atoms-containing fatty acid derivative that includes a ring consisting of five carbon atoms. This material was discovered in 1935 by the Swedish physiologist Wolf von Euler, who named prostaglandin because he thought it was secreted from the prostate gland. It is now widely known that prostaglandin exists in animal tissues and is rapidly metabolized after synthesis from polyunsaturated fatty acids. Such prostaglandins stimulate smooth muscle contraction according to their shapes, and in some animals, they lower or raise blood pressure, decrease or increase the cohesive force of blood, stimulate ion transport to the membrane, stimulate inflammation, and inhibit vascular disease and virus infection.

Prostaglandins and their analogs are chemically unstable and have a short effective life due to rapid metabolism in vivo. This is because prostaglandins and their analogs generally have active sites when they are in the form of hydroxyl and carboxyl groups, and enzymes rapidly inactivate these active groups. Prostaglandins and their analogs are also present in molecular weights that are small enough to enable the removal and release thereof from the body (Narumiya S. et al., 1999, Physiol. Rev., 79(4), 1193-1226). The chemical instability and the short effective period of prostaglandins and their analogs limit their use for the treatment of diseases such as respiratory, reproductive, neurological, endocrine, and cardiovascular systems.

Therefore, to solve the above-mentioned problems, studies are being conducted to develop a pharmaceutically acceptable formulation which provides, to prostaglandins and their analogs, high stability, an extensive administration method, an effective activity or a longer effective period. As an example of the related art, Korean Patent No. 0598660 discloses a 5-thia-w-substituted phenyl-prostaglandin E derivative capable of binding strongly to a prostaglandin receptor to provide excellent activity, Korean Patent No. 0850133 discloses a prostaglandin nitrooxy derivative which reduces side effects caused by prostaglandin and maximizes pharmacological effect, and Korean Patent Laid-Open No. 2001-0023839 discloses aromatic C16-C20-substituted tetrahydro prostaglandins useful as FP agonists.

Prostaglandin has a short biological activity due to rapid metabolism in vivo. The first step in this metabolic process is the oxidation of prostaglandin in which prostaglandin is deactivated by $NAD^+$-dependent 15-hydroxyprostaglandin dehydrogenase (15-PGDH) (Ensor, C. M, & Tai, H. H., 1995, J. Lipid Mediator Cell Signalling 12:313-319).

15-hydroxyprostaglandin dehydrogenase (15-PGDH) is an enzyme that degrades prostaglandin. In tissues in which 15-PGDH is not expressed, the amount of prostaglandin is increased. In addition, the 15-PGDH enzyme is localized in mammalian tissues and initially extracted and isolated from the placenta, lung, and kidney (Krook M et al., 1990, Biochemistry, 29, 738-743). This enzyme oxidizes prostaglandin-based compounds containing a hydroxyl group (—OH) at a C-15 position for the conversion into 15-keto-prostaglandin and thus prostaglandin-based compounds lose their biological activity (Tai H H et al., 2002, Adv Exp Med Biol, 507, 245-250).

On the other hand, recently published research has shown that 15-PGDH has a potential role in carcinogenesis, that is, when human prostate cancer cells are treated with androgen, 15-PGDH is remarkably expressed compared to when not treated therewith, and it is seen that the expression of 15-PGDH is increased in nude mouse-derived tumors injected with human prostate cancer cells (M. Tong., 2000, Biochem. Biophys. Res. Commun., 276, 77~81). In addition, when the concentration of intracellular prostaglandin $E_2$ is increased by inhibition of 15-PGDH activity, not only hair growth (U.S. Pat. No. 7,396,525) and blood flow improvement but also various physiological activities such as cell regeneration through stem cell activation occur (Yin g Wu et al., 2011, J Med Chem 54 (14), 5260-5264; Goesslin g W et al., Cell Stem Cell 8, 445-458). Therefore, many researchers expected that inhibition or reduction of 15-PGDH expression in cells may lead to a treatment of various diseases caused by lack of intracellular prostaglandin $E_2$, such as cell regeneration, as well as inhibiting cancer development.

Therefore, studies on inhibitors capable of inhibiting the activity of 15-PGDH have been actively carried out. In particular, it is disclosed that cyclooxygenase inhibitors, flavonoids, phytophenolic compounds, and peroxisome proliferator-activated receptor γ (PPAR γ) have an inhibitory effect of 15-PGDH.

In addition to the above-mentioned compounds, the inventors of the present disclosure studied a new compound capable of inhibiting 15-PGDH, and found thiazolidinedione derivatives having a high 15-PGDH inhibitory effect, and further found that these derivatives efficiently regulate intracellular prostaglandin $E_2$ and have cell regeneration effects and expected the possibility of the treatment of various diseases caused by the lack of intracellular prostaglandin $E_2$, thereby completing the present disclosure.

DETAILED DESCRIPTION OF THE DISCLOSURE

Technical Problem

An aspect provides a compound represented by any one of Formulae 1a and 1b or a pharmaceutically acceptable salt thereof.

Another aspect provides a pharmaceutical composition for cell regeneration including the compound or a pharmaceutically acceptable salt thereof as an active ingredient.

Another aspect provides a pharmaceutical composition for increasing prostaglandin $E_2$ including the compound or a pharmaceutically acceptable salt thereof as an active ingredient.

Another aspect provides a pharmaceutical composition for preventing alopecia or promoting hair growth, the pharmaceutical composition including the compound or a pharmaceutically acceptable salt thereof as an active ingredient.

Another aspect provides a pharmaceutical composition for the prevention or treatment of cardiovascular disease, the pharmaceutical composition including the compound or a pharmaceutically acceptable salt thereof as an active ingredient.

Another aspect provides a pharmaceutical composition for the prevention or treatment of gastrointestinal disease, the pharmaceutical composition including the compound or a pharmaceutically acceptable salt thereof as an active ingredient.

Another aspect provides a pharmaceutical composition for the prevention or treatment of kidney disease, the pharmaceutical composition including the compound or a pharmaceutically acceptable salt thereof as an active ingredient.

Another aspect provides a pharmaceutical composition for promoting bone formation, the pharmaceutical composition including the compound or a pharmaceutically acceptable salt thereof as an active ingredient.

Another aspect provides a pharmaceutical composition for the treatment of burns or wounds, the pharmaceutical composition including the compound or a pharmaceutically acceptable salt thereof as an active ingredient.

Another aspect provides a pharmaceutical composition for the prevention or treatment of atopy, the pharmaceutical composition including the compound or a pharmaceutically acceptable salt thereof as an active ingredient.

Another aspect provides a method of preventing alopecia or promoting hair growth in a subject, treating cardiovascular disease, gastrointestinal disease, kidney disease, cell regeneration, atopy, or burns or wounds, or promoting cell regeneration or bone formation.

Technical Solution

An aspect provides a compound represented by any one of Formulae 1a and 1b or a pharmaceutically acceptable salt thereof.

Formula 1a

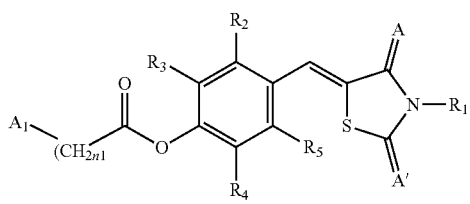

Formula 1b

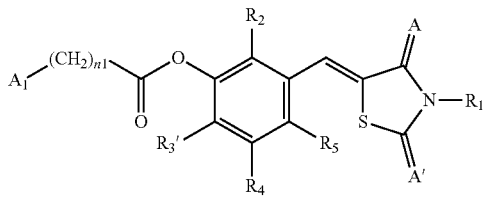

In Formulae 1a and 1b, A and A' are each independently O or S, $A_1$ may be each independently selected from hydrogen, deuterium, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, and a substituted or unsubstituted $C_1$-$C_{60}$ heteroaryl group.

$R_1$ may be selected from hydrogen, deuterium, a substituted or unsubstituted $C_1$-$C_{10}$ alkyl group, and a substituted or unsubstituted $C_1$-$C_{10}$ alkoxy group, $R_2$, $R_3$, $R_3'$, $R_4$. and $R_5$ may be each independently selected from hydrogen, deuterium, —F, —Cl, —Br, —I, —OH, a cyano group, a nitro group, an amino group, an amidino group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group, n1 may be each independently an integer from 0 to 10, and at least one substituent of the substituted $C_1$-$C_{10}$ alkyl group, the substituted $C_2$-$C_{10}$ alkenyl group, the substituted $C_2$-$C_{10}$ alkynyl group, the substituted $C_1$-$C_{10}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, and the substituted $C_1$-$C_{60}$ heteroaryl group may be selected from deuterium, —F, —Cl, —Br, —I, —OH, a cyano group, a nitro group, an amino group, an amidino group, and a $C_1$-$C_{10}$ alkyl group.

Regarding the compound or a pharmaceutically acceptable salt thereof, in Formulae 1a and 1b, A and A' may each be O, $R_1$ may be H or deuterium, $R_2$, $R_3$, and $R_3'$ may be each independently selected from hydrogen, deuterium, —F, —Cl, —Br, —I, and a substituted or unsubstituted $C_1$-$C_{10}$ alkoxy group, $R_4$ and $R_5$ may be each independently selected from hydrogen and deuterium, n1 may be each independently an integer from 0 to 10, 0 to 6, or 0 to 4, and $A_1$ may be selected from hydrogen, deuterium, a substituted or unsubstituted $C_3$-$C_{10}$ cycloalkyl group, and a substituted or unsubstituted $C_6$-$C_{20}$ aryl group. Regarding the compound or a pharmaceutically acceptable salt thereof, the substituted or unsubstituted $C_1$-$C_{10}$ alkoxy group may be an unsubstituted $C_1$-$C_6$ alkoxy group, for example, methoxy or ethoxy, the substituted or unsubstituted $C_3$-$C_{10}$ cycloalkyl group may be an unsubstituted $C_3$-$C_{10}$ cycloalkyl group, and the substituted or unsubstituted $C_6$-$C_{20}$ aryl group may be an unsubstituted $C_6$-$C_{12}$ aryl group, for example, a phenyl group.

Regarding the compound or a pharmaceutically acceptable salt thereof, $A_1$ in Formulae 1a and 1b may be a group represented by one of Formulae 2-1 to 2-5.

Formula 2-1

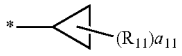

Formula 2-2

Formula 2-3

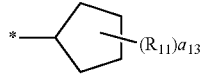

Formula 2-4

Formula 2-5

In Formulae 2-1 to 2-5, $R_{11}$ may be selected from hydrogen, deuterium, —F, —Cl, —Br, —I, and a substituted or unsubstituted $C_1$-$C_{10}$ alkyl group, a11 may be an integer from 0 to 2,
a12 may be an integer from 0 to 3,
a13 may be an integer from 0 to 4,
a14 may be an integer from 0 to 5.

Here, $a_{11}$ represents the number of $R_{11}$. When $a_{11}$ is 2 or more, two or more $R_{11}(s)$ may be the same or different from each other. The meaning of a12 to a14 may be understood from the description provided in connection with a11 and the structure of Formulae 2-1 to 2-5.

For example, $a_{11}$ to $a_{14}$ in Formulae 2-1 to 2-5 may be each independently 0 or 1. for example, $R_{11}$ in Formulae 2-1 to 2-5 may be hydrogen or deuterium. * indicates a binding site to a neighboring atom.

Regarding the compound or a pharmaceutically acceptable salt thereof, $A_1$ in Formulae 1a and 1b may be a group represented by one of Formulae 2-1 to 2-5.

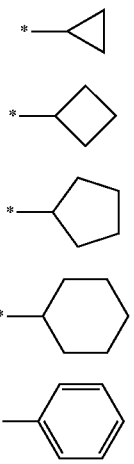

Formula 2-6

Formula 2-7

Formula 2-8

Formula 2-9

Formula 2-10

* in Formulae 2-6 to 2-10 indicates a binding site to a neighboring atom.

The compound or a pharmaceutically acceptable salt thereof may be represented by one of Formulae 3-1 to 3-5:

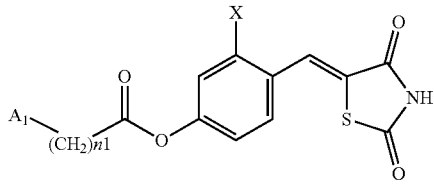

Formula 3-1

Formula 3-2

Formula 3-3

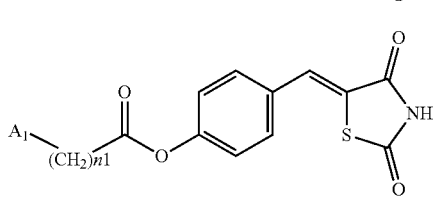

Formula 3-4

Formula 3-5

Regarding Formulae 3-1 to 3-5, $A_1$, n1, and $R_3$ are the same as explained in connection with Formulae 1a and 1b, X may be —F, —Cl, —Br, or —I, and $R_3$ may be a substituted or unsubstituted $C_1$-$C_{10}$ alkoxy group. X may be, for example, —Cl or —Br, and $R_3$ may be an unsubstituted $C_1$-$C_{10}$ alkoxy group, for example, an unsubstituted $C_1$-$C_6$ alkoxy group, or an unsubstituted $C_1$-$C_4$ alkoxy group.

The compound represented by one of Formulae 3-1 to 3-4 may be any one of Formulae 3-6 to 3-11.

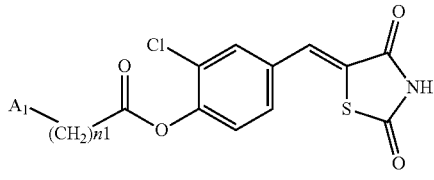

Formula 3-6

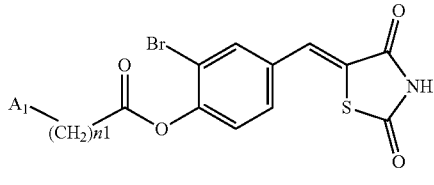

Formula 3-7

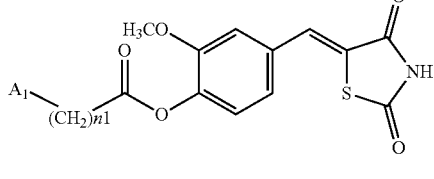

Formula 3-8

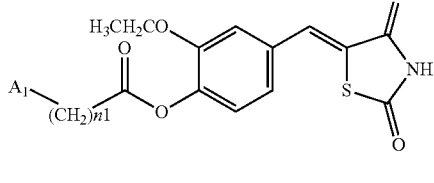

Formula 3-9

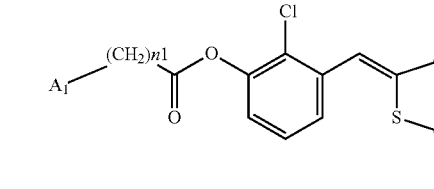

Formula 3-10

Formula 3-11

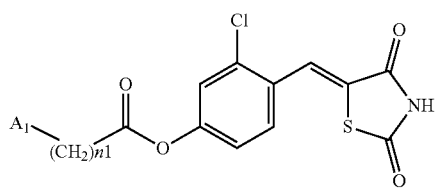

$A_1$, n1, and $R_3$ in Formulae 3-6 to 3-11 are the same as explained in connection with Formulae 1a and 1b.

Regarding the compound or a pharmaceutically acceptable salt thereof, $A_1$ in Formulae 3-1 to 3-5 may be selected from groups represented by Formulae 2-1 to 2-5:

Formula 2-1

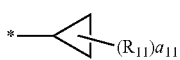

Formula 2-2

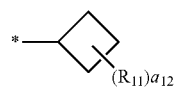

Formula 2-3

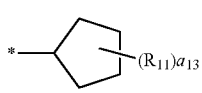

Formula 2-4

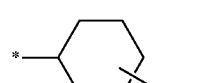

Formula 2-5

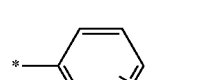

In Formulae 2-1 to 2-5, $R_{11}$ may be selected from hydrogen, deuterium, —F, —Cl, —Br, —I, and a substituted or unsubstituted $C_1$-$C_{10}$ alkyl group, a11 may be an integer from 0 to 2,
a12 may be an integer from 0 to 3,
a13 may be an integer from 0 to 4,
a14 may be an integer from 0 to 5.

Here, $a_{11}$ represents the number of $R_{11}$. When $a_{11}$ is 2 or more, two or more $R_{11}$(s) may be the same or different from each other. The meaning of $a_{12}$ to $a_{14}$ may be understood from the description provided in connection with a11 and the structure of Formulae 2-1 to 2-5.

For example, $a_{11}$ to $a_{14}$ in Formulae 2-1 to 2-5 may be each independently 0 or 1. For example, $R_{11}$ in Formulae 2-1 to 2-5 may be hydrogen or deuterium. * indicates a binding site to a neighboring atom.

$A_1$ in Formulae 3-1 to 3-5 may be selected from groups represented by Formulae 2-6 to 2-9.

Formula 2-6

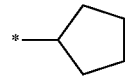

Formula 2-7

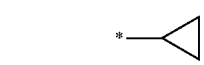

Formula 2-8

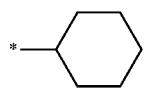

Formula 2-9

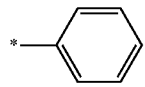

Formula 2-10

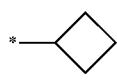

* in Formulae 2-6 to 2-10 indicates a binding site to a neighboring atom.

In some embodiments, the compound or a pharmaceutically acceptable salt thereof may be selected from Compounds 1 to 105 illustrated below.

1

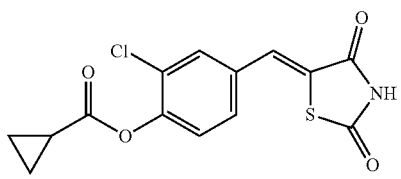

2

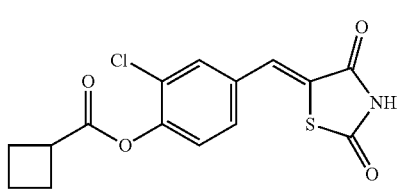

3

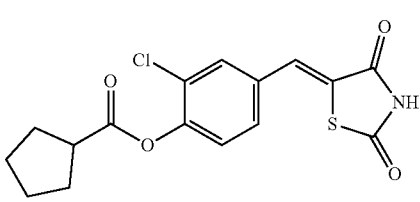

4

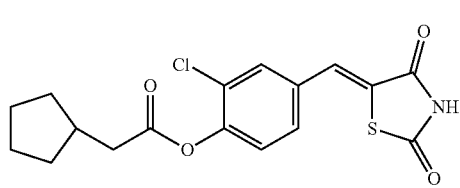

5

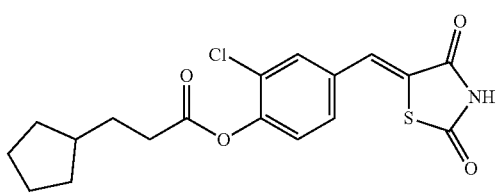

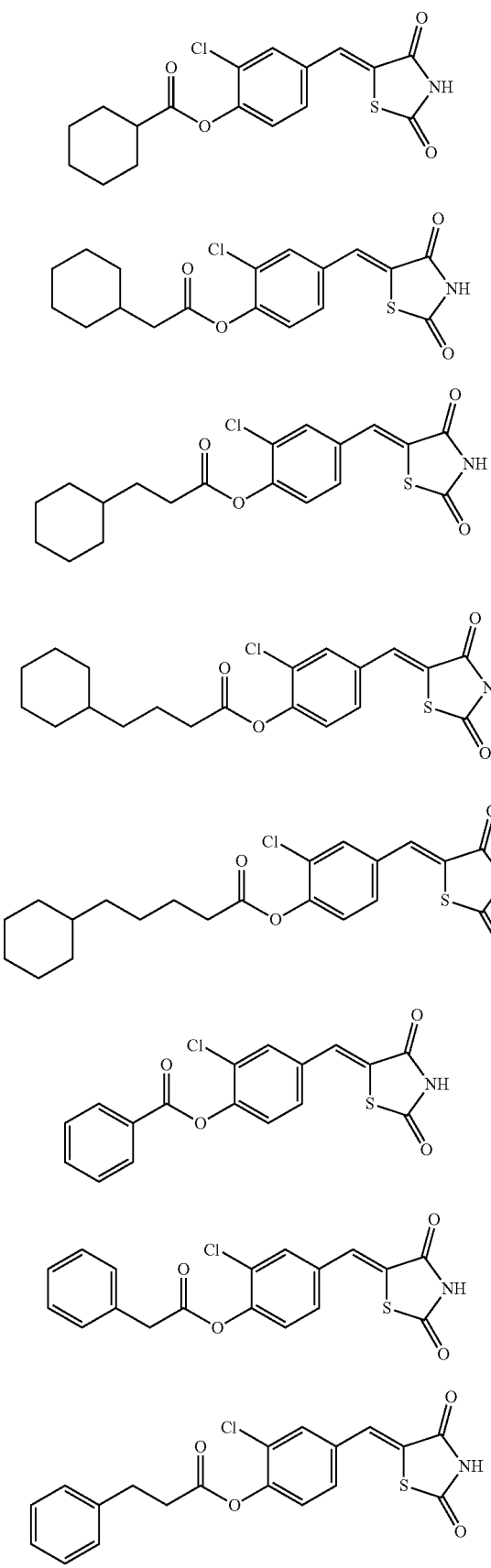
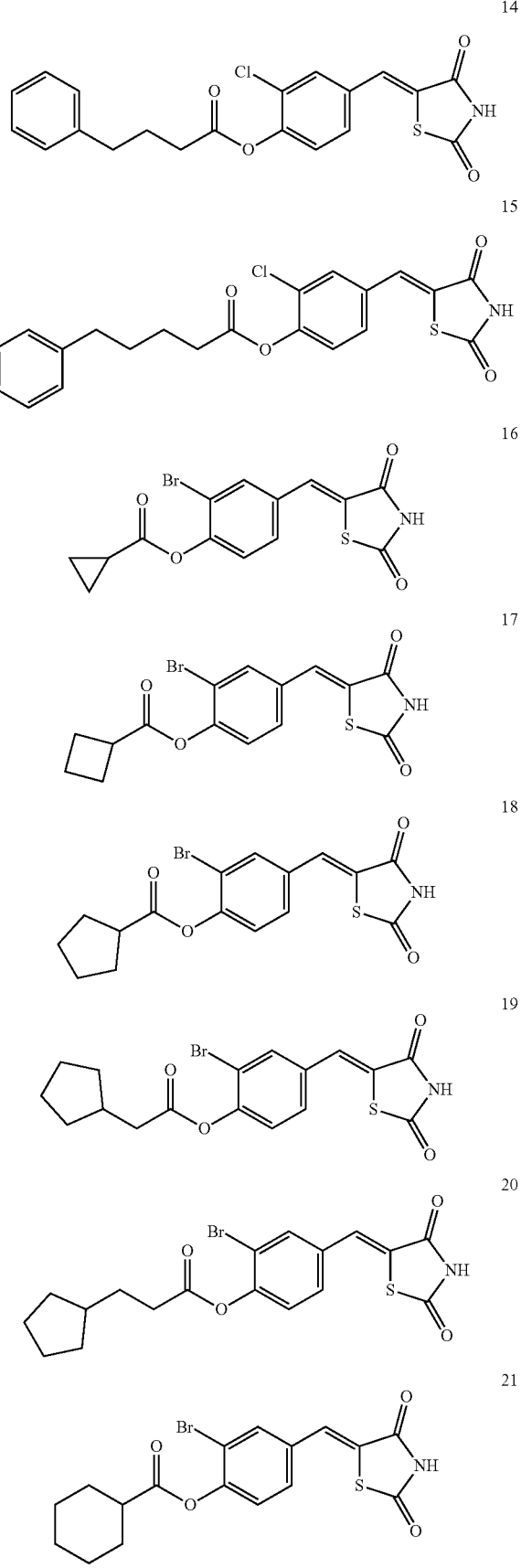

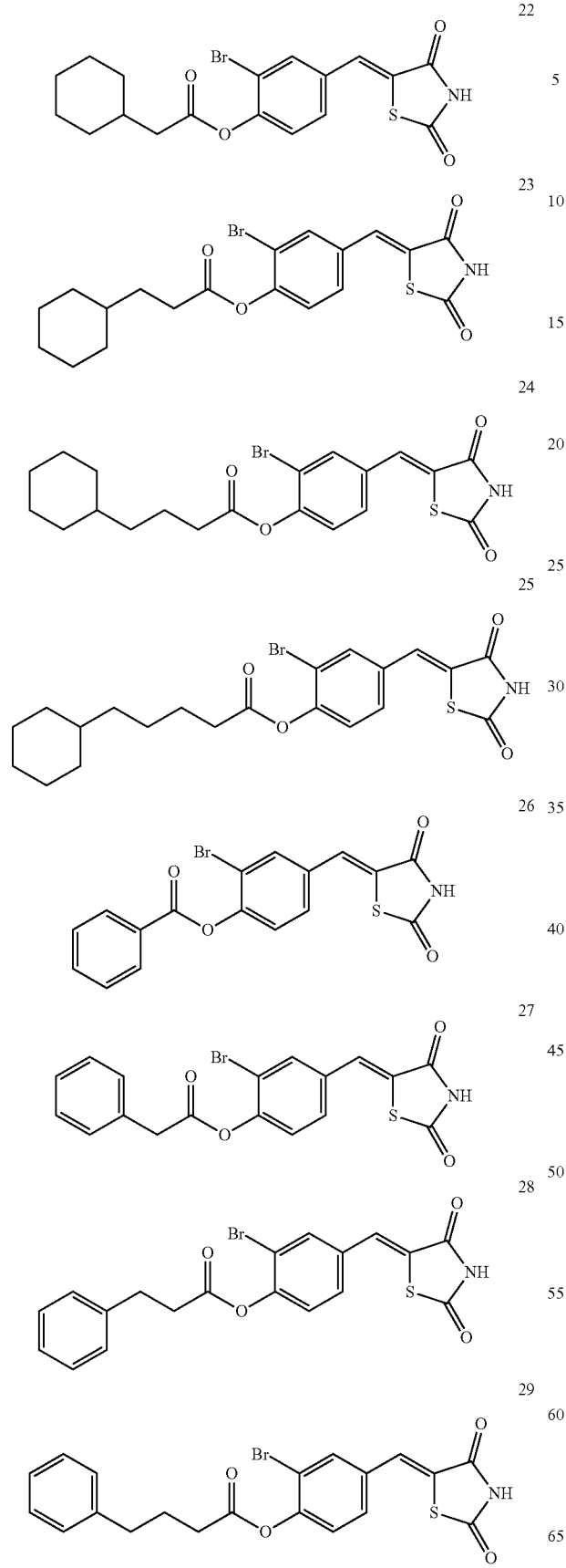
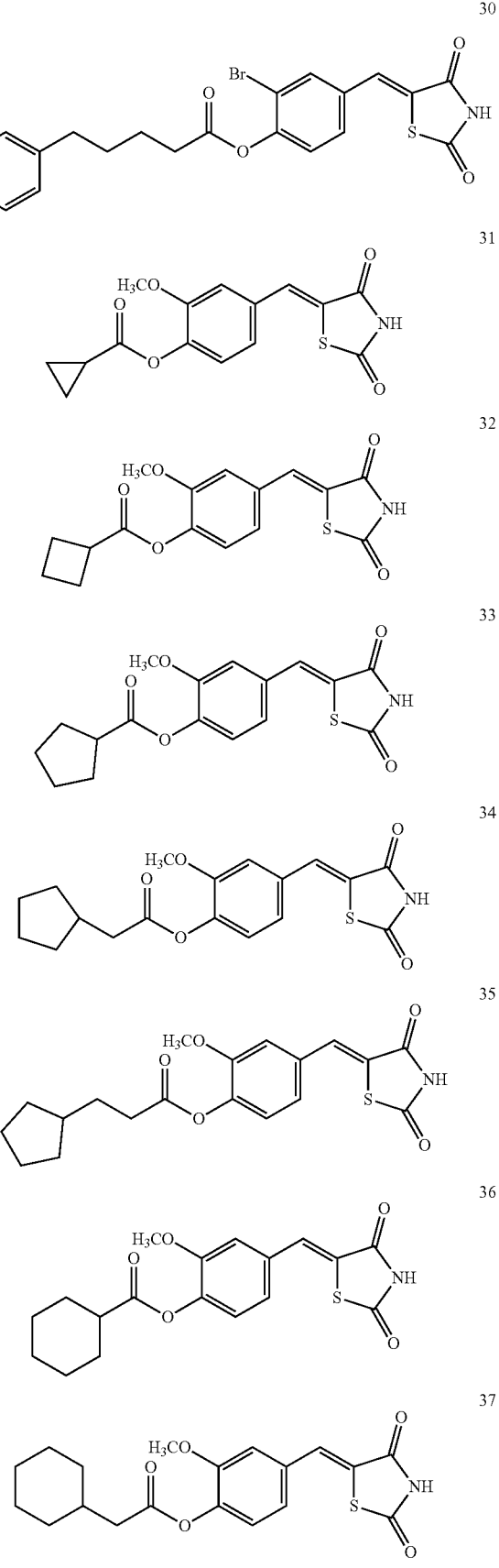

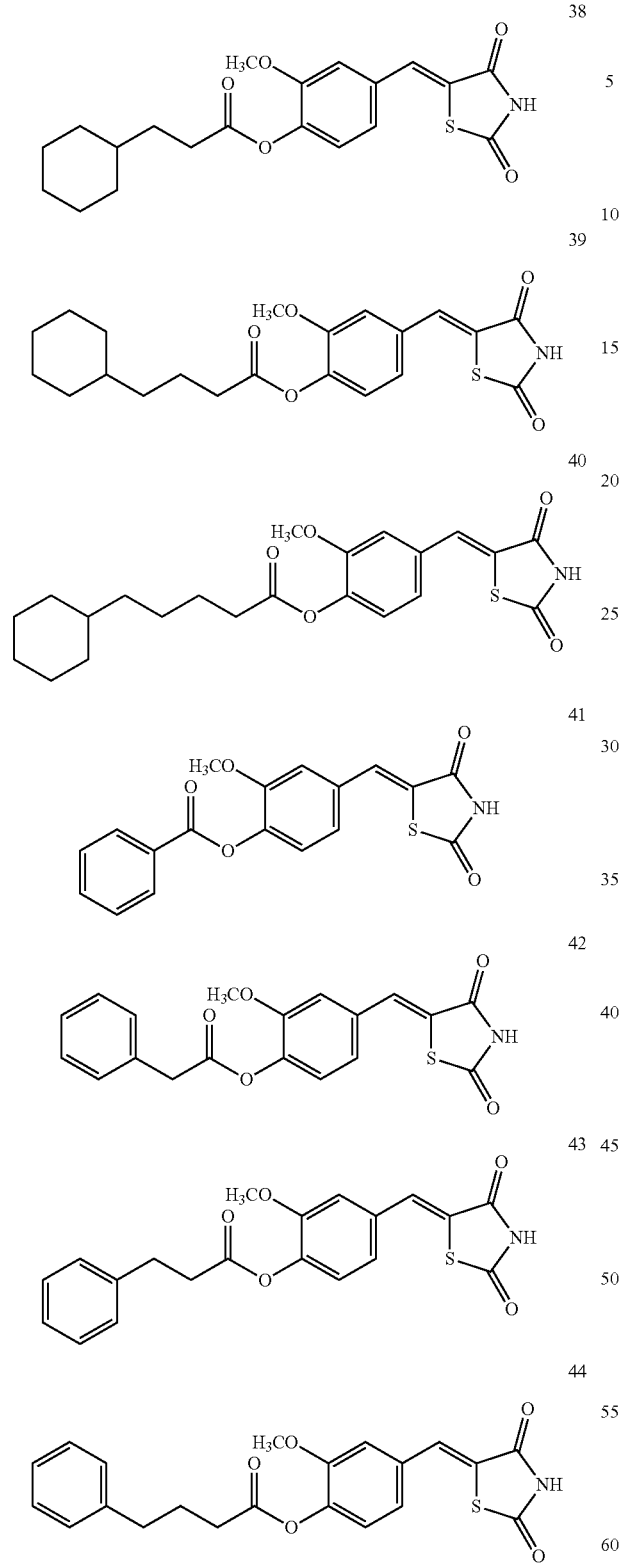
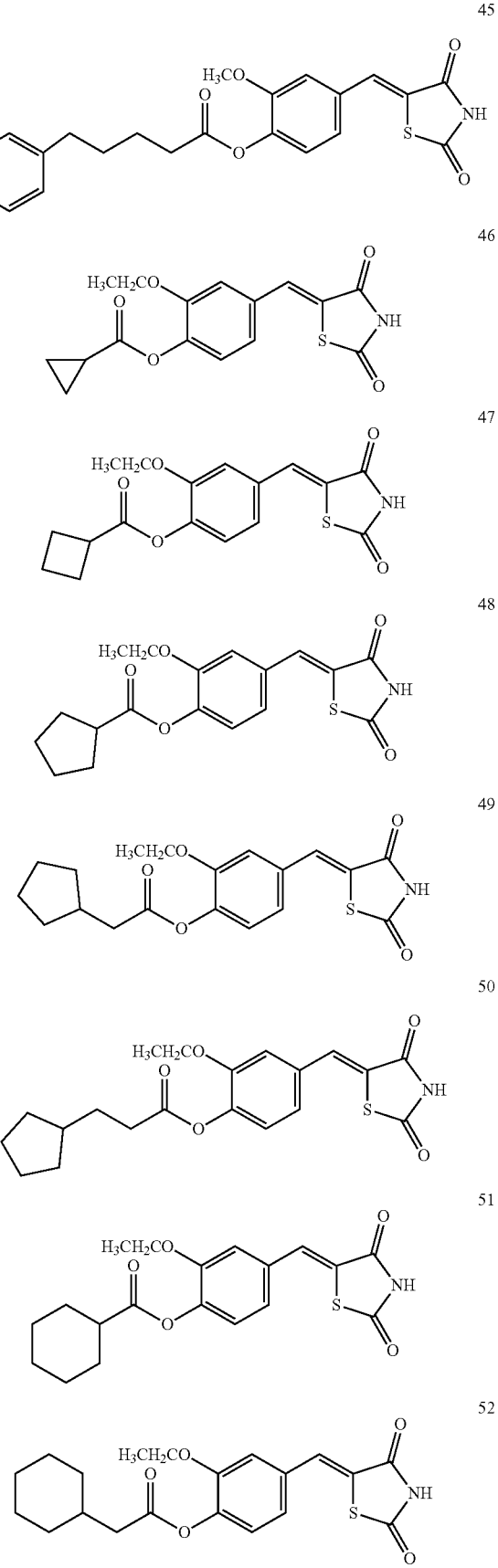

53
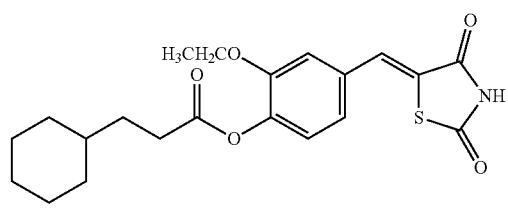
54
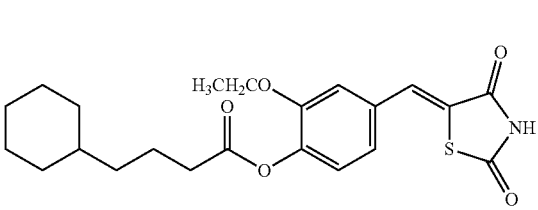
55
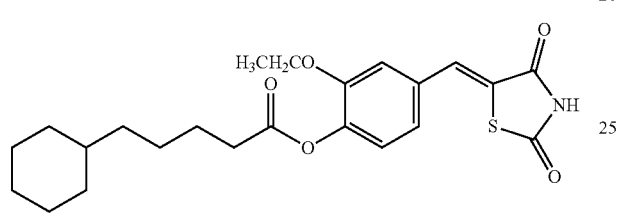
56
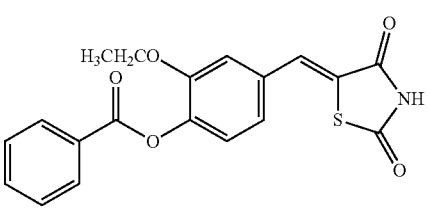
57
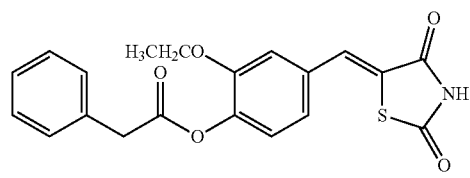
58
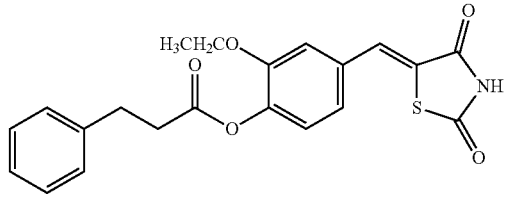
59
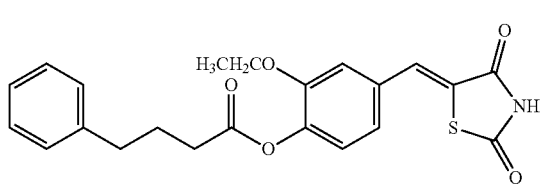
60
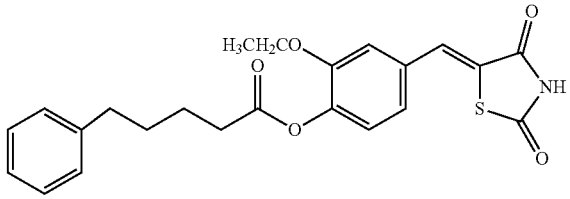
61
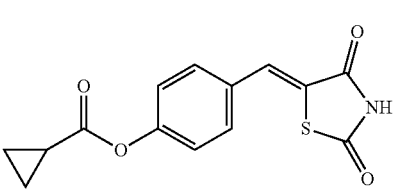
62
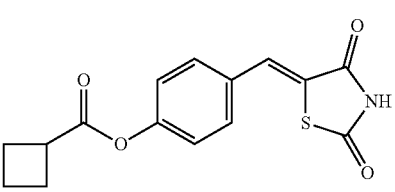
63
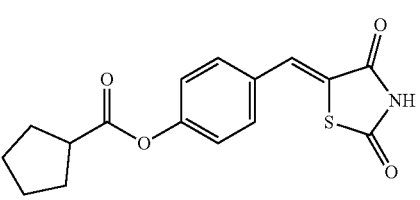
64
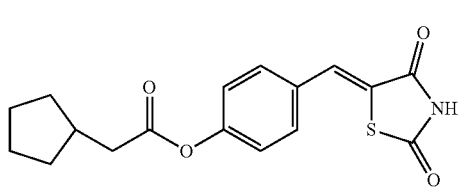
65
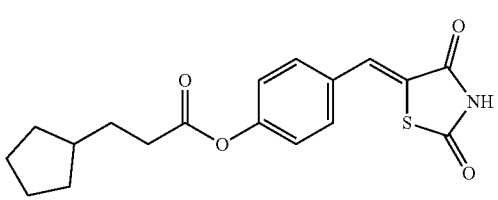
66
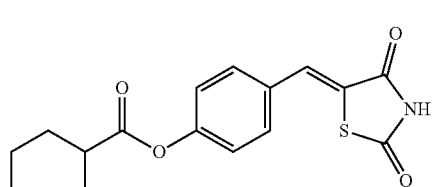
67
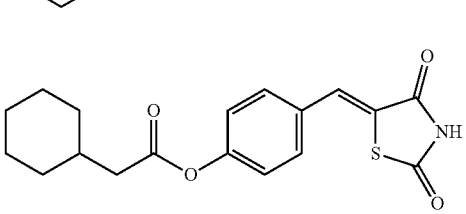

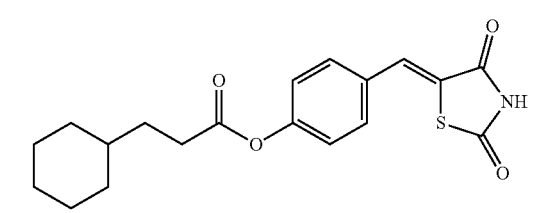
68
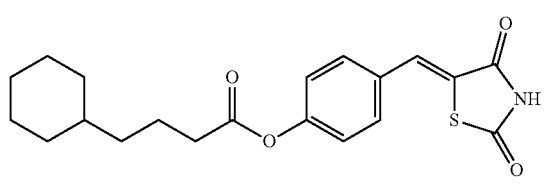
69
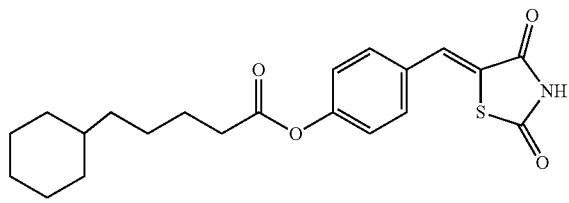
70
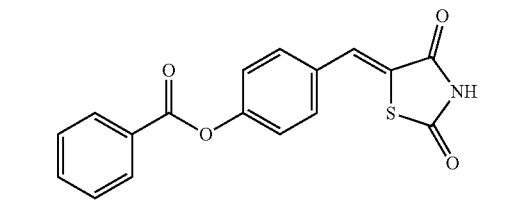
71
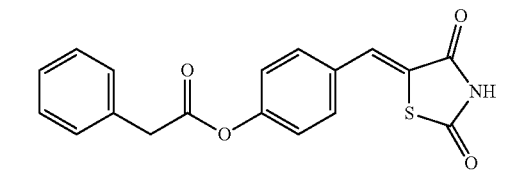
72
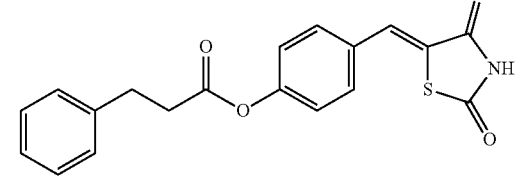
73
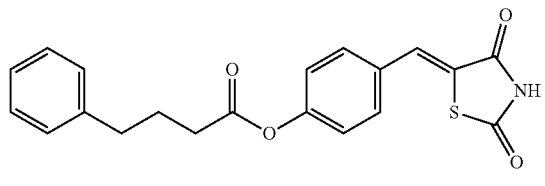
74
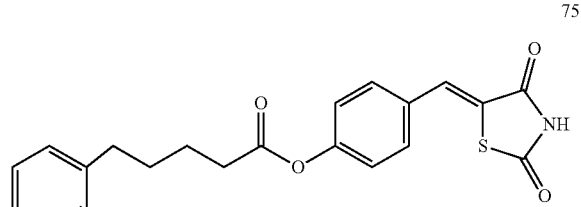
75
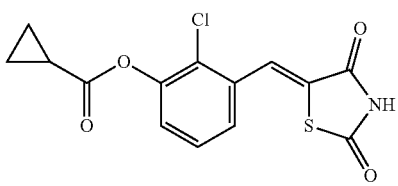
76
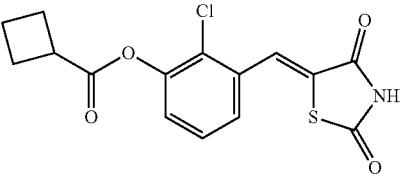
77
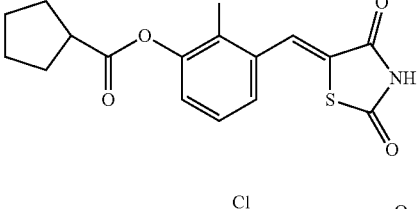
78
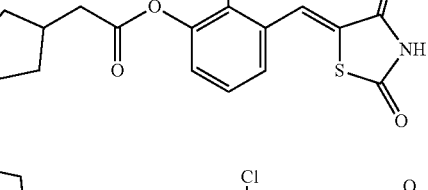
79
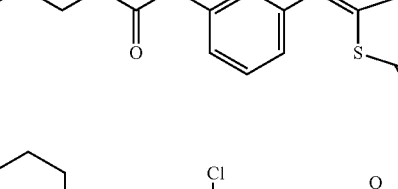
80
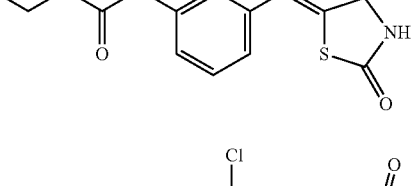
81
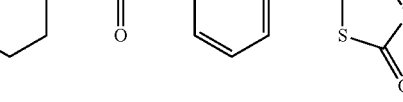
82

83
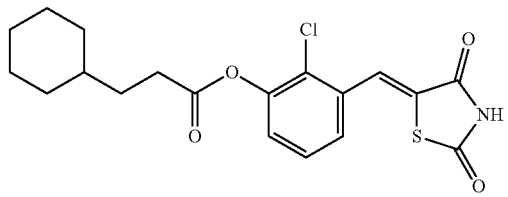
84
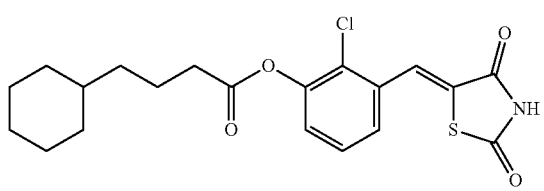
85
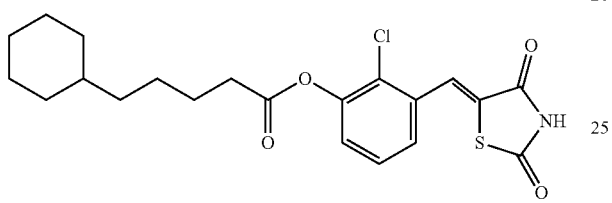
86
87
88
89
90
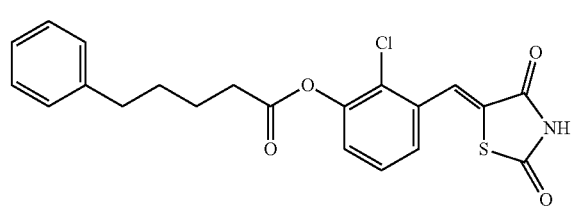
91
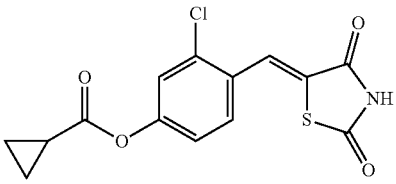
92
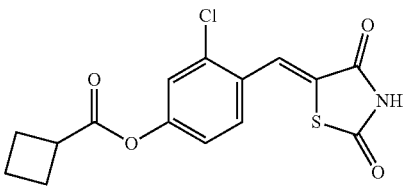
93
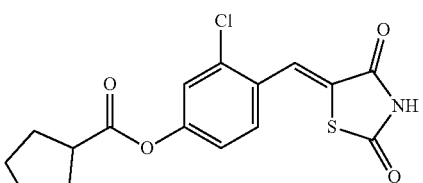
94
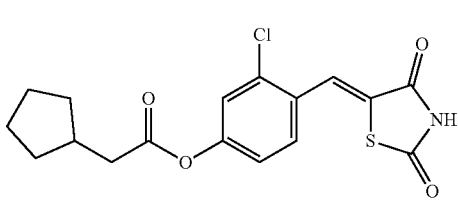
95
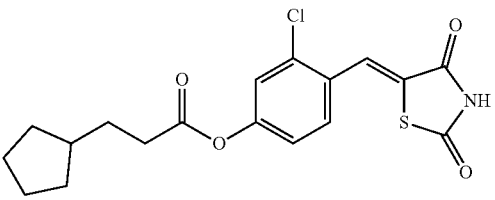
96
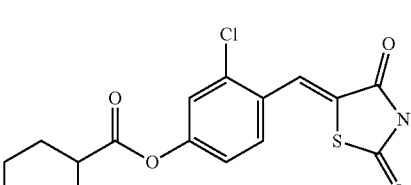
97
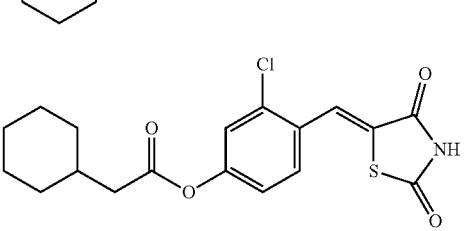

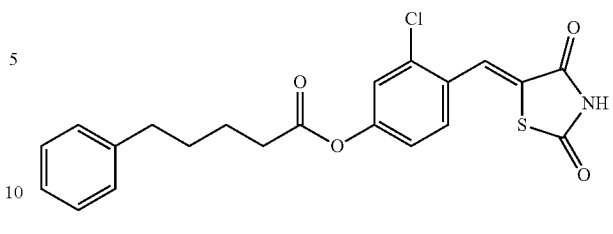

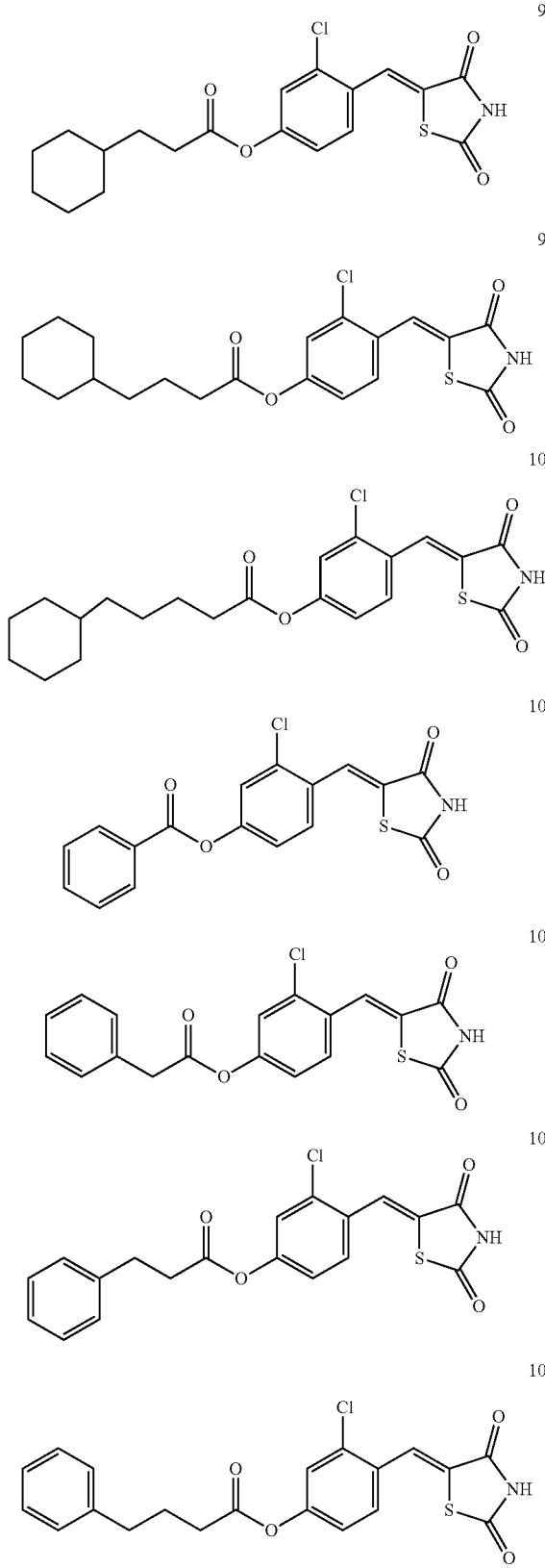

The term "C1-C10 alkyl group" used herein refers to a linear or branched, monovalent C1-C10 aliphatic hydrocarbon. Examples thereof are a methyl group, an ethyl group, a propyl group, an isobutyl group, a sec-butyl group, a ter-butyl group, a pentyl group, a hexyl group, or the like.

The term "C1-C10 alkoxy group" used herein refers to a monovalent group represented by —OA101 (wherein A101 is the C1-C10 alkyl group), and examples thereof are a methoxy group, an ethoxy group, a propoxy group, etc.

The term "C2-C10 alkenyl group" used herein refers to a hydrocarbon group having at least one carbon double bond in the middle or at the terminus of the C2-C10 alkyl group, and examples thereof are an ethenyl group, a propenyl group, and a butenyl group.

The term "C2-C10 alkynyl group" used herein refers to a hydrocarbon group having at least one carbon triple bond in the middle or at the terminus of the C2-C10 alkyl group, and examples thereof are an ethynyl group, a propynyl group, etc.

The term "C3-C10 cycloalkyl group" used herein refers to a monovalent saturated hydrocarbon monocyclic group having 3 to 10 carbon atoms, and examples thereof are a cyclopropyl group, a cyclobutyl group, a cyclopentyl group, a cyclohexyl group, a cycloheptyl group, etc.

The term "C1-C10 heterocydoalkyl group" used herein refers to a monovalent saturated monocyclic group having at least one heteroatom selected from N, O, P, and S as a ring-forming atom and 1 to 10 carbon atoms, and examples thereof are a tetrahydrofuranyl group, and a tetrahydrothiophenyl group.

The term "C3-C10 cycloalkenyl group" refers to a monocyclic group having 3 to 10 carbon atoms, and has at least one double bond in its ring and non-aromaticity, and examples thereof are a cyclopentenyl group, a cyclohexenyl group, a cycloheptenyl group, etc.

The term "C1-C10 heterocycloalkenyl group" used herein refers to a monovalent monocyclic group that has at least one heteroatom selected from N, O, P, and S as a ring-forming atom, 1 to 10 carbon atoms, and at least one carbon-carbon double bond in its ring. Examples of the C1-C10 heterocycloalkenyl group are a 2,3-dihydrofuranyl group, a 2,3-dihydrothiophenyl group, etc.

The term "C6-C60 aryl group" used herein refers to a monovalent group having a carbocylic aromatic system having 6 to 60 carbon atoms. Examples of the C6-C60 aryl group are a phenyl group, a naphthyl group, an anthracenyl group, a phenanthrenyl group, a pyrenyl group, a chrysenyl group, etc. When the C6-C60 aryl group includes two or more rings, these rings may be fused with each other.

The term "C1-C60 heteroaryl group" used herein refers to a monovalent group that has at least one hetero atom selected from N, O, P and S as a ring-forming element and a carbocylic aromatic system having 1 to 60 carbon atoms, and examples of the C1-C60 heteroaryl group are a pyridinyl group, a pyrimidinyl group, a pyrazinyl group, a pyridazinyl group, a triazinyl group, a quinolinyl group, and an isoquinolinyl group, etc. When the C1-C60 heteroaryl group includes two or more rings, these rings may be fused with each other.

At least one substituent of the substituted C1-C10 alkyl group, the substituted C2-C10 alkenyl group, the substituted C2-C10 alkynyl group, the substituted C1-C10 alkoxy group, the substituted C3-C10 cycloalkyl group, the substituted C1-C10 heterocycloalkyl group, the substituted C3-C10 cycloalkenyl group, the substituted C1-C10 heterocycloalkenyl group, the substituted C6-C60 aryl group, and the substituted C1-C60 heteroaryl group may be selected from deuterium, —F, —Cl, —Br, —I, —OH, a cyano group, a nitro group, an amino group, an amidino group, and a C1-C10 alkyl group.

In one or more embodiments of the present disclosure, a salt may be prepared in situ during the final isolation, purification and synthesis of the compound according to one embodiment of the present disclosure, or separately prepared by reacting with an inorganic base or an organic base. When the compound according to the present disclosure contains an acidic group, a base and a salt may be formed. Examples of the salt are, but not limited to, salts with alkali metals such as lithium salts, sodium salts or potassium salts; salts with alkali metals such as lithium salts, sodium salts or potassium salts; salts with other metals such as magnesium salts; organic base salts such as salts with dicyclohexylamine; and salts with basic amino acids such as lysine or arginine. When the compound according to the present disclosure contains a basic group in its molecule, an acid-added salt may be formed, and examples thereof are, but are not limited to, salts with inorganic acids, for example, hydrohalic acids (e.g. hydrofluoric acid, hydrobromic acid, hydroiodic acid, or hydro chloric acid), nitric acid, carbonic acid, sulfuric acid, or phosphoric acid; salts with lower alkyl sulfonic acids such as methanesulfonic acid, trifluoromethanesulfonic acid or ethanesulfonic acid; salts with benzenesulfonic acid or p-toluenesulfonic acid; salts with organic carboxylic acids such as acetic acid, fumaric acid, tartaric acid, oxalic acid, maleic acid, malic acid, succinic acid or citric acid; and salts with amino acids such as glutamic acid or aspartic acid.

In one or more embodiments, the compound according to the present disclosure may include a derivative, such as the hydrate or solvate of the compound (J. M. Keith, 2004, Trahedron Letters, 45(13), 2739-2742).

The compound according to one embodiment of the present disclosure may be naturally isolated or prepared by chemical synthesis methods known in the art. In general, to obtain the compound, substituent compounds are reacted with an appropriate reaction solvent to obtain intermediate product, which is then reacted with an appropriate reaction solvent.

The reaction solvent that is available in the preparation process is not particularly limited as long as it does not participate in the reaction. Examples of such a reaction solvent are ethers such as diethyl ether, tetrahydrofuran, and dioxane; halogenated hydrocarbons such as dichloromethane, and chloroform; amines such as pyridine, piperidine, and triethylamine; alkyl ketones such as acetone, methyl ethyl ketone, and methyl isobutyl; alcohols such as methanol, ethanol and propanol; an aprotic polar solvent such as N, N-dimethylformamide, N, N-dimethylacetamide, acetonitrile, dimethylsulfoxide, and hexamethylphosphoric triamide. From among non-reactive organic solvents used in organic synthesis, solvents which are capable of isolating water produced during the reaction by a dean-stark trap may be used. Examples of such solvents include, but are not limited to, benzene, toluene, xylene, and the like. The separation and purification of the reaction product is carried out through, for example, a concentration process and an extraction process, which are usually performed in organic synthesis. According to purpose, separation and purification may be carried out by purification by column chromatography on silica gel.

Methods of preparing the compound according to an embodiment of the present disclosure may be modified, and in this case, intermediate products obtainable at any of its steps may be used as a starting material for other steps, and the starting material may be formed in the reaction system under reaction conditions, or reaction components may be used in the form of their salts or optically in the form of an enantiomer.

Also, the present disclosure includes isomers, such as substantially pure geometric (cis or trans) isomers, optical isomers (enantiomers) or racemate isomers, which are selected depending on a substitute used to prepare the compound according to the present disclosure, an intermediate product, and a preparation method.

The compound or a pharmaceutically acceptable salt thereof according to the present disclosure has an activity of suppressing or inhibiting 15-hydroxy prostaglandin dehydrogenase (15-PGDH).

In one experimental example of the present disclosure, it was confirmed whether the compound or a pharmaceutically acceptable salt thereof suppresses or inhibits the 15-PGDH. To confirm the suppressing or inhibiting activity, the amount of NADH produced was measured after the compound or a pharmaceutically acceptable salt thereof was brought into contact with cells. When the activity of 15-PGDH is high, $NAD^+$ is reduced and NADH is produced, and thus, prostaglandin is oxidized to produce an inactive 15-keto prostaglandin. This is why the activity of 15-PGDH is able to be confirmed by measuring the amount of NADH.

As a result, it was confirmed that the compound according to the present disclosure or a pharmaceutically acceptable salt thereof has the activity of inhibiting 15-PGDH (see Table 1 and Table 2 of Example)

Therefore, the inventors of the present application confirmed that the compound according to the present disclosure or a pharmaceutically acceptable salt thereof is an inhibitor of 15-PGDH. Thus, the compound according to the present disclosure or a pharmaceutically acceptable salt thereof may be used for the prevention or treatment of diseases which may be caused by 15-PGDH. For example, the compound according to the present disclosure or a pharmaceutically acceptable salt thereof may be used for the prevention or treatment of pathologic conditions or symptoms of disease that is caused by the reduction in the amount of prostaglandin $E_2$ or disease that is treated by an increase in prostaglandin E2.

Prostaglandin is known to play an important role in the growth of hair. Further, it is disclosed that, to maintain or increase the density of hair, prostaglandins in various types ($A_2$, $F_{2a}$, $E_2$) need to be stored in various regions including the hair follicle or skin environments adjacent thereto (Colombe L et al., 2007, Exp. Dermatol, 16(9), 762-9). However, it is known that enzymes specifically involved in the degradation of prostaglandin are present in the dermal papilla of hair, a crucial area for hair survival, and 15-PGDH inactivates prostaglandins, for example, $PGF_{2a}$ and $PGE_2$, damaging the scalp and causing alopecia (Michelet J F et al., 2008, Exp. Dermatol, 17(10), 821-8).

Thus, since the compound according to the present disclosure or a pharmaceutically acceptable salt thereof has the activity of suppressing or inhibiting the 15-hydroxy prostaglandin dehydrogenase (15-PGDH) which degrades prostaglandin, alopecia may be prevented and hair growth may be promoted.

Accordingly, another aspect provides a pharmaceutical composition for preventing alopecia or promoting hair growth, the pharmaceutical composition including the compound or a pharmaceutically acceptable salt thereof as an active ingredient.

Regarding the method, the term "alopecia" refers to the entire hair follicle state having a loss of partial or entire permanent hair, and the subject of alopecia and hair growth includes human keratin fibers, for example, hair, eyebrows, eyelashes, beard, mustache, etc. of human beings. The alopecia includes all forms of alopecia, such as circular alopecia, frontal alopecia, and whole body alopecia, and the pharmaceutical composition for preventing the alopecia or promoting hair growth may be applied directly to or spread directly on the hair or skin, or may be applied by washing or shampooing.

Another aspect provides a pharmaceutical composition for the prevention or treatment of cardiovascular disease, the pharmaceutical composition including the compound or a pharmaceutically acceptable salt thereof as an active ingredient.

Prostaglandins, including prostaglandin homologues generated in vivo, are known to maintain a proper action of the blood vessel wall, for example, in the relaxation of blood vessels to enable the flow of blood, prevent aggregation of platelets, and contribute to the control of proliferation of smooth muscle cell surrounding the blood vessel wall (Yan, Chen, et al., 2006, J. Physiol. Clin., Invest). In addition, when the production of prostaglandin is suppressed or prostaglandin loses its activity, the degeneration of the inner wall of the blood vessel wall, the aggregation of platelets and the disruption of the cell action of the smooth muscle may occur, and thus, cardiovascular diseases may develop. In the case of hypertension, the production of prostaglandin is been reduced (Tan et al., 2008, Cardiovasc Res., 78(1), 130-8).

Therefore, since the novel derivative compounds according to the present disclosure have an activity of suppressing or inhibiting 15-PGDH that degrades prostaglandins, prostaglandin ($PGE_2$) may be stored inside cells and activated to prevent or treat cardiovascular diseases.

The cardiovascular disease includes a disease that is caused by degeneration of the inner wall of the blood vessel wall, the aggregation of platelets, or abnormalities in the regulation of cell action of smooth muscle, and a disease that is caused by hypercholesterolemia due to abnormally high levels of low density lipoprotein cholesterol (LDL-cholesterol), cholesterol, and triglyceride in the blood. Examples of such cardiovascular diseases are arteriosclerosis, hypertension, angina pectoris, hyperlipidemia, myocardial infarction, and heart failure.

Thus, the cardiovascular disease may be selected from hypertension, arteriosclerosis, angina pectoris, hyperlipidemia, myocardial infarction, and heart failure.

Another aspect provides a pharmaceutical composition for the prevention or treatment of gastrointestinal disease, the pharmaceutical composition including the compound or a pharmaceutically acceptable salt thereof as an active ingredient.

Regarding the method, the gastrointestinal disease may be gastritis or gastric ulcer.

Gastritis and gastric ulcers, which are typical diseases of gastrointestinal diseases, refer to a condition in which gastric mucosa is digested by gastric acid to form ulcers. The gastric wall is generally composed of a mucosal layer, a submucosal layer, a muscle layer, and a serosa. Gastritis is a condition in which the mucous membrane is damaged, and a gastric ulcer is a condition in which the submucosal layer or muscular layer is damaged. However, the cause of gastritis and gastric ulcer is not well known, although their frequency of occurrence is high. It is known to be caused only by the imbalance of attack factors and defensive factors, that is, more attack factors or less defensive factors. The increase of attack factors may be due to increased secretion of acids and pepsin, and the decrease of defense factors may be due to deficiency in structure and morphology of gastric mucosa, decrease of mucus secretion, decrease of bicarbonate secretion, and decrease of prostaglandin production. On the other hand, a therapeutic agent for gastritis and gastric ulcer that are currently in use include defensive factors, such as antacids that neutralize already produced gastric acid without affecting the secretion of gastric acid, drugs inhibiting the secretion of gastric acid, secretagogue of prostaglandin, and agents for coating gastric wall. The role of prostaglandin in maintaining the protective and protective action of the gastric mucosa is known to be great (Wallace J L., 2008, Physiol Rev., 88(4), 1547-65; S. J. Konturek et al., 2005, Journal of Physiology and Pharmacology, 56(5), 5~31).

Therefore, since the compound according to the present disclosure or a pharmaceutically acceptable salt thereof is effective for the prevention or treatment of gastritis and gastric ulcer due to the activity of suppressing or inhibiting the 15-PGDH degrading prostaglandin which protects the gastric mucosa. The inner wall of gastrointestines including, in addition to the stomach, esophagus, duodenum, small instestine, and large intestine, is also surrounded by the mucosa. Accordingly, it may be expected to prevent or treat gastrointestinal inflammation or ulcer by the mechanism. Since the inflammation or ulcer caused by mucosal injury may cause functional dyspepsia, vomiting, stools, stomach cramps, abdominal pain, diarrhea or constipation, the compound or a pharmaceutically acceptable salt thereof is effective for the prevention or treatment of gastrointestinal disease including the gastritis and gastric ulcer.

Another aspect provides a pharmaceutical composition for the prevention or treatment of kidney disease, the pharmaceutical composition including the compound or a pharmaceutically acceptable salt thereof as an active ingredient. The kidney disease may include diabetic nephropathy, hypertensive nephropathy, glomerulonephritis, pyelonephritis, interstitial nephritis, lupus nephritis, polycystic kidney disease, or renal failure. Symptoms of kidney disease may include kidney tissue destruction, imbalance of the circulation of salt and water, edema due to abnormal nutrient uptake or excretion, hematuria, proteinuria, glomerulosclerosis, hypertension, hypotension, arrhythmia, and interstitial fibrosis.

In the kidney, prostaglandin is known to regulate renal blood flow and regulate urine formation by both renal and vascular effects. According to clinical studies, prostaglandin 1 ($PGE_1$) improves creatinine clearance of patients with chronic kidney disease, prevents graft rejection and cyclosporine toxicity in renal transplant patients, and reduces excretion rates of urinary albumin and the level of N-acetyl-β-D-glucosaminidase of diabetic nephropathy patient, and methods of preventing renal dysfunction by intravenous administration of prostaglandin compounds such as PGE$_1$, PGE$_2$. and PGI$_2$ have been disclosed (see Porter, Am., 1989, J. Cardiol., 64: 22E-26E, U.S. Pat. No. 5,807,895). In addition, prostaglandin acts as a vasodilator extending the blood vessels in the kidney, and when the production of prostaglandin is suppressed in the kidney, kidney damage may occur (see Hao, C M, 2008, Annu Rev Physiol, 70, 357-77).

Therefore, the compound according to the present disclosure or a pharmaceutically acceptable salt thereof which suppresses or inhibits prostaglandin degrading 15-PGDH may be used to prevent or treat kidney disease caused by renal dysfunction.

The term "renal dysfunction" refers to a condition in which normal creatinine is less than the purification amount, a condition in which normal free water is less than the purification amount, a condition in which the normal levels of urea or nitrogen or potassium or creatinine in blood exceeds the normal, a condition in which a renal enzyme, such as gamma glutamyl synthase enzyme, alanine phosphatidase, N-acetyl-β-D-glucosaminidase or β-2-microglobulin, has a modulated activity, or a condition in which macroalbuminuria exceeds normal levels.

As described above, the compound according to the present disclosure or a pharmaceutically acceptable salt thereof is an inhibitor of 15-PGDH, and inhibits the degradation of prostaglandin, thereby preventing alopecia and promoting hair growth, is effective for the treatment or prevention of cardiovascular diseases, gastrointestinal diseases, and kidney diseases, and is, as a vasodilator, effective for the circulatory disorder, such as chronic obstructive pulmonary disease, Burgers disease, Raynaud's disease, and bronchitis.

Meanwhile, prostaglandin, including PGE$_1$, PGE$_2$. and PGF$_{2a}$, has been shown to stimulate bone resorption and bone formation to promote the action of increasing bone volume and bone strength (see H. Kawaguchi et al., Clinical Orthop. Rel. Res., 313, 1995, 36~46; J. Keller et al., Eur. J. Exp. Musculoskeletal Res., January, 1992, 8692). On the other hand, 15-PGDH inhibits the activity of prostaglandin as described above.

Thus, when the activity of 15-PGDH is suppressed, the action of prostaglandin suppressed by 15-PGDH, that is, bone resorption and bone formation may be promoted.

Accordingly, the compound according to the present disclosure or a pharmaceutically acceptable salt thereof may inhibit the activity of 15-PGDH, and thus may have an effect of promoting bone resorption and bone formation.

Accordingly, another aspect provides a pharmaceutical composition for promoting bone formation, the pharmaceutical composition including the compound or a pharmaceutically acceptable salt thereof as an active ingredient.

Another aspect provides a pharmaceutical composition for cell regeneration including the compound or a pharmaceutically acceptable salt thereof as an active ingredient.

The term 'cell regeneration' refers to the recovery of damaged cells up to such a level that the cells have their normal functions, or the repair of damaged cells to such a level that the number of cells reaches its normal level. Accordingly, the pharmaceutical composition for cell regeneration has the effect of promoting the recovery of damaged tissue. The damage of cells may be caused by physical or chemical stimulation to the cell or tissue or by an intracellular mental cause, autoimmunity, aging, ultraviolet irradiation, or the like, and the cell may be a cell constituting all the organs constituting the subject. Accordingly, the pharmaceutical composition for cell regeneration is effective for promoting the regeneration of the cell or tissue damaged by those causes. In one embodiment, the pharmaceutical composition for cell regeneration is effective for a disease that requires promotion of cell regeneration, and examples of such disease are corneal injury, cataract, dementia, neurodegenerative disease, interstitial lung disease, chronic obstructive pulmonary disease, emphysema, cirrhosis, cirrhosis, renal failure, periodontal disease, arthritis, necrotizing skin disease, skin aging, and tumor, but are not limited thereto.

In another embodiment, the pharmaceutical composition for cell regeneration may be a pharmaceutical composition for the treatment of wounds or burns.

The compound according to the present disclosure or a pharmaceutically acceptable salt thereof is effective in inhibiting 15-PGDH, and thus has the effect of treating wounds or burns. Among prostaglandins, PGE$_2$ is known to act as a mediator to treat wounds or burns. Therefore, inhibition of 15-PGDH, which inhibits the activity of PGE$_2$, which is responsible for treating wounds or burns, may result in the therapeutic effect obtained from PGE$_2$ when a wound or burn occurs in the skin.

Cell regeneration in the liver, fin, and fetus is almost complete without leaving scarring. PGE$_2$ is directly involved in this process, that is, PGE$_2$ activates the Wnt signaling pathway and promotes the differentiation of hematopoietic stem cell. Therefore, when the concentration of intracellular PGE$_2$ is increased by inhibiting 15-PGDH activity, the cell regeneration effect may be obtained.

Another aspect provides a pharmaceutical composition for the treatment of atopy, the pharmaceutical composition including the compound or a pharmaceutically acceptable salt thereof as an active ingredient.

Atopy is a chronic inflammatory disease of the skin accompanied by skin damage, dysfunction of the epithelial layer and severe pruritus. PGE$_2$ induced by mesenchymal stem cells is known to involve in the suppression of allergic reactions. For example, PGE$_2$ inhibits degranulation of mast cells which is one of the causes of allergic inflammatory diseases including atopy, and plays an important role in lymphocyte cytokine secretion and T regulatory cell expansion (Kim H S, et al., Stem Cells, 2015 April, 33 (4), 1254-66, Cho S K et al., PLoS ONE 10 (7), e0131813). Therefore, when 15-PGDH activity is inhibited to increase the concentration of intracellular PGE$_2$ in blood flow, it may be involved in the immunosuppression reaction and thus the effects of the prevention or treatment of atopy may be obtained.

An inhibitor of 15-PGDH described above refers to a compound capable of inhibiting or reducing the activity of 15-PGDH enzyme in human, or inhibiting, reducing, or decelerating the reaction catalyzed by the enzyme, and such a compound is the compound according to the present disclosure or a pharmatically acceptable salt thereof.

The pharmaceutical composition including, as an active ingredient, the compound or a pharmaceutically acceptable salt thereof according to the present disclosure may be prepared by mixing the active ingredient with a pharmaceutically acceptable carrier or excipient or by diluting the active ingredient with a diluent according to a conventional method. The pharmaceutical composition may additionally include fillers, anti-coagulants, lubricants, humectants, fragrances, emulsifiers, preservatives, etc.

The pharmaceutical composition according to the present disclosure may be formulated, by using a known method, in such a way that after the pharmaceutical composition is administered to mammals, the active ingredient is rapidly, sustainedly, or delayedly released.

The pharmaceutical composition according to the present disclosure may be prepared in various parenteral or oral administration forms by using known methods, In the case of a solid preparation for oral administration, an excipient, if needed, a binder, a disintegrant, a lubricant, a coloring agent, a flavoring agent and/or thickening agent are added, and the obtained mixture may be prepared in the form of a tablet, a sugar coated tablet, a granule, a powder, or a capsule. As the additive, any one that is conventionally used in the art may be used. Examples of the excipient are lactose, sucrose, sodium chloride, glucose, starch, calcium carbonate, Kaolin, microcrystalline cellulose, and silicate. Examples of the binder are water, ethanol, propanol, sweet syrup, sucrose solution, starch solution, gelatin solution, carboxymethylcellulose, hydroxypropylcellulose, hydroxypropyl starch, methylcellulose, ethylcellulose, shellac, calcium phosphate, and polypyrrolidone. Examples of the disintegrant are dried starch, sodium arginate, agar powder, sodium bicarbonate, calcium carbonate, sodium lauryl sulfate, stearic acid monoclyceride, and lactose. Examples of the lubricant are refined talc, stearates, sodium borate, and polyethylene glycol. Examples of the flavoring agent are sucrose, bitter orange peel, citric acid, and tartaric acid.

When a liquid preparation for oral administration is prepared, a flavoring agent, a buffer, a stabilizer, and a thickening agent may be added to the compound according to the present disclosure, and the liquid preparation may be prepared in the form of a solution, a syrup, or an elixir agent by using a conventional method. Examples of the buffer are sodium citrate, and examples of the stablizer are tragacanth, acacia, and gelatin. To prepare an injectable preparation, a pH adjusting agent, a buffering agent, a stabilizer, a relaxing agent, a local anesthetic agent and the like may be added to the compound according to the present disclosure, and the resulting mixture may be used as a subcutaneous injection, an intramuscular injection, or an intravenous injection. Examples of the pH adjusting agent and the buffering agent include sodium citrate, sodium acetate, and sodium phosphate. Examples of the stabilizer are sodium pyrosulfite, EDTA, thioglycolic acid and thiolactic acid. Examples of the local anesthetic agent are procaine hydrochloride and lidocaine hydrochloride, and examples of the relaxing agent are sodium chloride and glucoside.

As for the preparation of suppositories, pharmaceutically acceptable carriers known in the art, such as polyethylene glycol, lanolin, cacao butter or fatty acid triglyceride, and, optionally, a surfactant such as Tween may be added to the compound according to the present disclosure. Suppositories may be prepared according to a conventional method.

As for the preparation of an ointment, a base, a stabilizer, a moisturizing agent, a preservative, and the like, which are conventionally used for producing an ointment, is added to the compound according to the present disclosure, and a conventional method of preparing an ointment may be used. Examples of the base are liquid paraffin, white wasserin, pewter, octyldodecyl alcohol, and paraffin. Examples of the preservative are methyl para-oxybenzoate, ethyl para-oxybenzoate, and propyl paraoxybenzoate.

The pharmaceutical composition formulated by using various methods as described above may be administered in a pharmaceutically effective amount through various routes including oral, transdermal, subcutaneous, intravenous, or muscular route.

The pharmaceutically effective amount as used herein refers to the amount of the compound sufficient to ameliorate or treat alopecia, cardiovascular diseases, gastrointestinal diseases, kidney diseases, wounds and burns, and may vary depending on disease and severity thereof, the age, body weight, body conditions, and gender of the patient, route of administration, duration of treatment, and the like. The pharmaceutically effective amount may be provided in an effective dosage of, for example, about 1 mg to about 1000 mg for oral administration, about 0.1 mg to about 500 mg for injection, and about 5 mg to about 1000 mg for suppository. The daily dosage of the formulation varies depending on the condition, body weight, age, and gender of the patient, and may not be fixed at certain levels. A typical daily dose for an adult may be in the range of about 0.1 mg to about 5000 mg, for example, about 1 mg to about 1000 mg. The daily administration may be performed once or repeatedly performed several times.

Another aspect provides a method of preventing alopecia or promoting hair growth in a subject, treating cardiovascular diseases, gastrointestinal diseases, kidney diseases, atopy, burns or wounds, or promoting bone formation or cell regeneration, the method including administering the compound or a pharmaceutically acceptable salt thereof to the subject. In one embodiment, the method may be used to promote cell regeneration in disease, such as corneal injury, cataract, dementia, neurodegenerative disease, interstitial lung disease, chronic obstructive pulmonary disease, emphysema, cirrhosis, cirrhosis, renal failure, periodontal disease, arthritis, necrotizing skin disease, skin aging, or tumor.

The subject may be a mammal. The mammal may be a human, a horse, cow, a pig, a cat, a dog, or sheep. The administration may be provided in an effective amount that is sufficient to prevent alopecia or promote hair growth in a subject, treat cardiovascular disease, gastrointestinal disease, kidney disease, or wounds, or promote bone formation or cell regeneration.

Advantageous Effects of the Disclosure

The novel thiazolidinedione derivative according to the present disclosure is excellent in inhibiting 15-hydroxyprostaglandin dehydrogenase. Accordingly, the novel thiazolidinedione derivative is effective for the prevention and treatment of cardiovascular diseases, gastrointestinal diseases and kidney diseases, which may be caused by 15-PGDH, the prevention of alopecia and the promotion of hair growth, the promotion of bone formation or cell regeneration, and the treatment of wounds.

DESCRIPTION OF THE DRAWINGS

FIG. 4 shows images showing the wound treatment effect of Compound 59 used at various concentrations, and FIG. 5 shows images showing the wound treatment effect of Compound 89 used at various concentrations.

MODE OF THE DISCLOSURE

Figure 1:
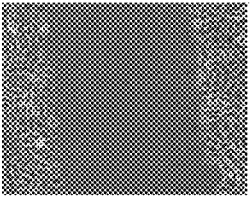
FIG. 1 shows images showing the wound treatment effect when Compounds 14 and 29 are used at a concentration of 5 µM.

Hereinafter, the present disclosure will be described in more detail through Examples. However, these Examples are intended to illustrate the present disclosure, and the scope of the present disclosure is not limited to these Examples.

Example 1

I. Preparation of Compounds

All the compounds used for the synthesis were obtained from Sigma-Aldrich inc., TCI inc., Junsei inc., and Merck inc. In the case of water-sensitive compounds, the reaction was carried out at an atmosphere of $N_2$.

For each compound, $^1H$ Nuclear magnetic resonance (NMR) was measured by using YH300(Oxford Inc.), and at 300 MHz and 296 K. In this case, $CDCl_3$ or TMS of DMSO was used as a reference sample. The chemical shift of the NMR was expressed in the unit of ppm, and the coupling constant of J-coupling was measured in the unit of Hz (Hertz).

Example 1. Preparation of Compound 1 ((Z)-2-chloro-4-((2,4-dioxothiazolidin-5-ylidene)methyl) phenyl cyclopropanecarboxylate)

(1) Preparation of Reaction Intermediate

First, Compounds 1a to 15a (5-(3-chloro-4-hydroxybenzylidene)-thiazolidine-2,4-dione), which are reactants used for synthesizing Compounds 1 to 15, were synthesized according to the following scheme.

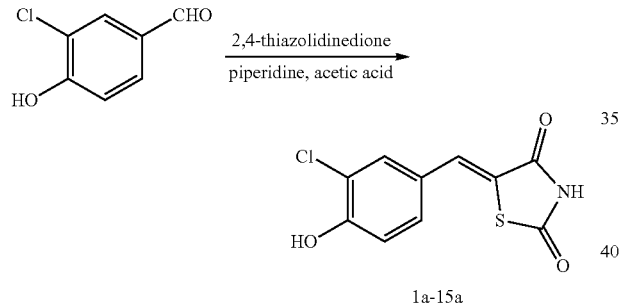

1a-15a 1 g (6.38 mmol) of 3-chloro-4-hydroxybenzaldehyde and 0.748 g (6.38 mmol) of 2,4-thiazolidinedione were placed in a round flask equipped with a Dean-Stark trap, and then dissolved in 20 ml of toluene, which is a reaction solvent, and then, 0.315 ml (3.19 mmol) of piperidine and 0.183 ml (3.19 mmol) of acetic acid were added thereto, followed by the reaction at a temperature of 80° C. for 18 hours or more. The completion of the reaction was confirmed by thin layer chromatography (TLC), and the resulting precipitate was recrystallized and then filtered under reduced pressure to obtain a pure solid.

Yield: 89.2%

1H NMR (300 MHz, DMSO-d6) δ 12.50 (s, 1H), δ 11.15 (s, 1H), δ 7.68 (s, 1H), δ 7.63 (d, J=2.19 Hz, 1H), δ 7.41 (dd, J=8.43 and 2.19 Hz, 1H), δ 7.12 (d, J=8.43 Hz, 1H)

(2) Preparation of Compound 1

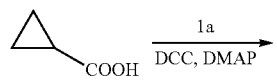

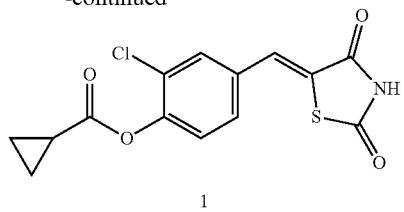

1

1 g (3.91 mmol) of 1a was added to a round-bottomed flask, and then, 0.311 g (3.91 mmol) of cyclopropanecarboxylic acid, and 0.04 g (0.33 mmol) of 4-(dimethylamino) pyridine (DMAP) were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 82.3%

1H NMR (300 MHz, DMSO-d6) δ 12.72 (s, 1H), δ 7.85 (d, J=1.83 Hz, 1H), δ 7.80 (s, 1H), δ 7.60 (dd, J=8.43 and 1.83 Hz, 1H), δ 7.50 (d, J=8.43 Hz, 1H), δ 2.02 (m, 1H), δ 1.16 (m, 4H)

Example 2. Preparation of Compound 2 ((Z)-2-chloro-4-((2,4-dioxothiazolidin-5-ylidene)methyl) phenyl cyclobutanecarboxylate)

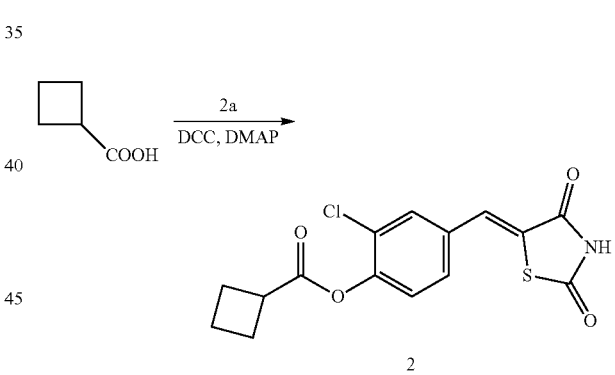

2

1 g (3.91 mmol) of 2a was added to a round-bottomed flask, and then, 0.374 g (3.91 mmol) of cyclobutanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 83.2%

1H NMR (300 MHz, DMSO-d6) δ 12.71 (s, 1H), δ 7.83 (d, J=1.83 Hz, 1H), δ 7.79 (s, 1H), δ 7.60 (dd, J=8.4 and 1.83 Hz, 1H), δ 7.49 (d, J=8.4 Hz, 1H), δ 3.58 (m, 1H), δ 2.42 (m, 4H), δ 2.09 (m, 2H)

Example 3. Preparation of Compound 3 ((Z)-2-chloro-4-((2,4-dioxothiazolidin-5-ylidene)methyl) phenyl cyclopentanecarboxylate)

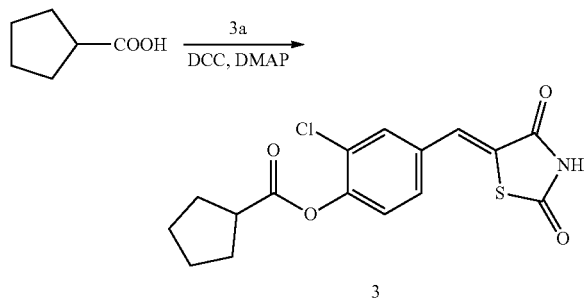

1 g (3.91 mmol) of 3a was added to a round-bottomed flask, and then, 0.425 g (3.91 mmol) of cyclopentanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.5%

1H NMR (300 MHz, DMSO-d6) δ 12.73 (s, 1H), δ 7.85 (d, J=1.83 Hz, 1H), δ 7.80 (s, 1H), δ 7.61 (dd, J=8.43 and 1.83 Hz, 1H), δ 7.50 (d, J=8.43 Hz, 1H), δ 3.18 (m, 1H), δ 2.08 (m, 4H), δ 1.70 (m, 4H)

Example 4. Preparation of Compound 4 ((Z)-2-chloro-4-((2,4-dioxothiazolidin-5-ylidene)methyl) phenyl 2-cyclopentylacetate)

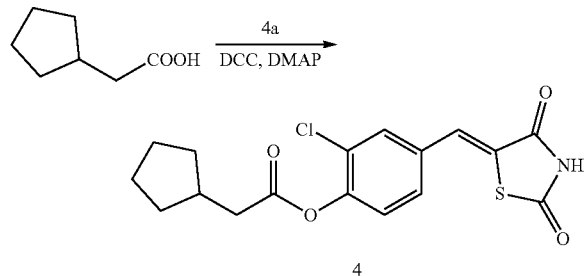

1 g (3.91 mmol) of 4a was added to a round-bottomed flask, and then, 0.491 g (3.91 mmol) of cyclopentylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.1%

1H NMR (300 MHz, DMSO-d6) δ 12.72 (s, 1H), δ 7.85 (d, J=1.83 Hz, 1H), δ 7.80 (s, 1H), δ 7.61 (dd, J=8.43 and 1.83 Hz, 1H), δ 7.48 (d, J=8.43 Hz, 1H), δ 2.68 (d, J=7.32 Hz, 2H), δ 2.33 (m, J=7.32 Hz, 1H), δ 1.90 (m, 2H), δ1.66 (m, 4H), δ 1.30 (m, 2H)

Example 5. Preparation of Compound 5 ((Z)-2-chloro-4-((2,4-dioxothiazolidin-5-ylidene)methyl) phenyl 3-cyclopentylpropanoate)

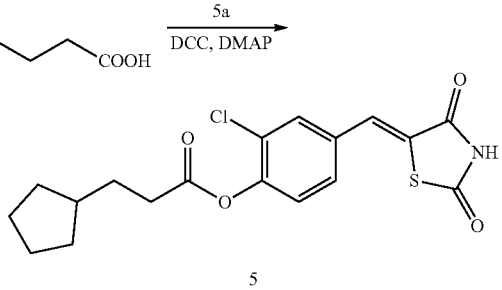

1 g (3.91 mmol) of 5a was added to a round-bottomed flask, and then, 0.558 g (3.91 mmol) of 3-cyclopentylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.3%

1H NMR (300 MHz, DMSO-d6) δ 12.73 (s, 1H), δ 7.85 (d, J=1.83 Hz, 1H), δ 7.80 (s, 1H), δ 7.61 (dd, J=8.4 and 1.83 Hz, 1H), δ 7.49 (d, J=8.4 Hz, 1H), δ 2.07 (t, J=7.32 Hz, 2H), δ1.90 (m, 4H), δ 1.62 (m, 4H), δ 1.19 (m, J=7.32 Hz, 3H)

Example 6. Preparation of Compound 6 ((Z)-2-chloro-4-((2,4-dioxothiazolidin-5-ylidene)methyl) phenyl cyclohexanecarboxylate)

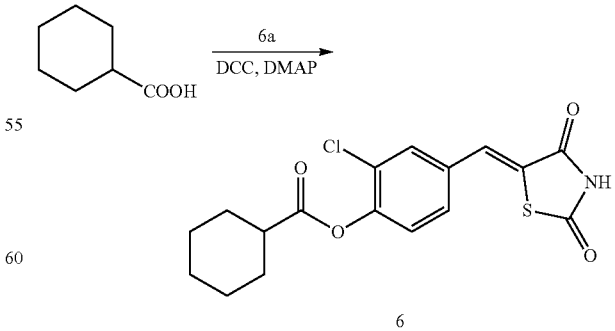

1 g (3.91 mmol) of 6a was added to a round-bottomed flask, and then, 0.501 g (3.91 mmol) of cyclohexanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 92.5%

1H NMR (300 MHz, DMSO-d6) δ 12.74 (s, 1H), δ 7.84 (d, J=1.83 Hz, 1H), δ 7.79 (s, 1H), δ 7.61 (dd, J=8.43 and 1.83 Hz, 1H), δ 7.47 (d, J=8.43 Hz, 1H), δ 2.73 (m, 1H), δ 2.08 (m, 2H), δ 1.76 (m, 2H), δ 1.65 (m, 2H), δ 1.41 (m, 4H)

Example 7. Preparation of Compound 7 ((Z)-2-chloro-4-((2,4-dioxothiazolidin-5-ylidene)methyl)phenyl 2-cyclohexylacetate)

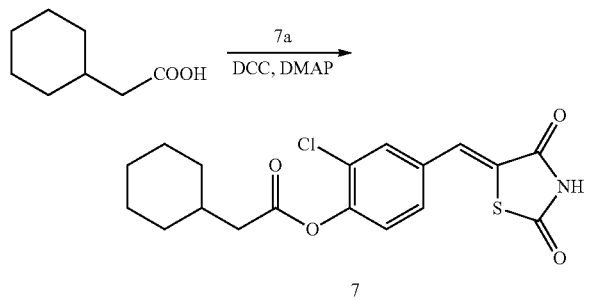

1 g (3.91 mmol) of 7a was added to a round-bottomed flask, and then, 0.556 g (3.91 mmol) of cyclohexylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 86.3%

1H NMR (300 MHz, DMSO-d6) δ 12.72 (s, 1H), δ 7.86 (d, J=1.83 Hz, 1H), δ 7.80 (s, 1H), δ 7.61 (dd, J=8.4 and 1.83 Hz, 1H), δ 7.48 (d, J=8.4 Hz, 1H), δ 2.51 (t, 2H), δ 1.86 (m, 1H), δ 1.71 (m, 4H), δ 1.32 (m, 6H)

Example 8. Preparation of Compound 8 ((Z)-2-chloro-4-((2,4-dioxothiazolidin-5-ylidene)methyl)phenyl 3-cyclohexylpropanoate)

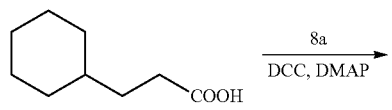

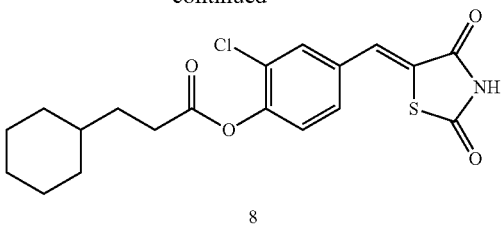

1 g (3.91 mmol) of 8a was added to a round-bottomed flask, and then, 0.611 g (3.91 mmol) of 3-cyclohexylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 93.4%

1H NMR (300 MHz, DMSO-d6) δ 12.72 (s, 1H), δ 7.85 (d, J=1.83 Hz, 1H), δ 7.79 (s, 1H), δ 7.61 (dd, J=8.43 and 1.83 Hz, 1H), δ 7.48 (d, J=8.43 Hz, 1H), δ 2.69 (t, 2H), δ1.75 (m, 8H), δ 1.33 (m, 3H), δ 0.95 (m, 2H)

Example 9. Preparation of Compound 9 ((Z)-2-chloro-4-((2,4-dioxothiazolidin-5-ylidene)methyl)phenyl 4-cyclohexylbutanoate)

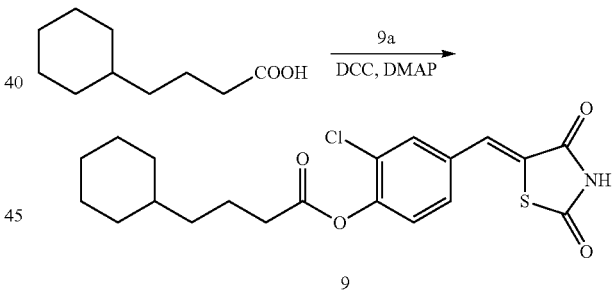

1 g (3.91 mmol) of 9a was added to a round-bottomed flask, and then, 0.666 g (3.91 mmol) of 4-cydohexylbutyric acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89%

1H NMR (300 MHz, DMSO-d6) δ 12.71 (s, 1H), δ 7.85 (d, J=1.83 Hz, 1H), δ 7.80 (s, 1H), δ 7.61 (dd, J=8.43 and 1.83 Hz, 1H), δ 7.48 (d, J=8.43 Hz, 1H), δ 2.66 (t, 2H), δ 1.70 (m, 7H), δ 1.30 (m, 6H), δ 0.92 (m, 2H)

Example 10. Preparation of Compound 10 ((Z)-2-chloro-4-((2,4-dioxothiazolidin-5-ylidene)methyl)phenyl 5-cyclohexylpentanoate)

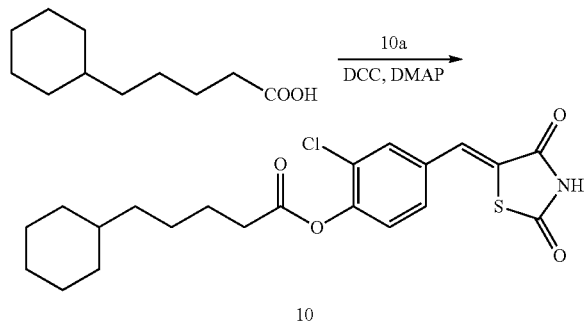

1 g (3.91 mmol) of 10a was added to a round-bottomed flask, and then, 0.751 g (3.91 mmol) of 5-cyclohexylpentanoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 91.2%

1H NMR (300 MHz, DMSO-d6) δ 12.71 (s, 1H), δ 7.84 (d, J=1.83 Hz, 1H), δ 7.80 (s, 1H), δ 7.61 (dd, J=8.43 and 1.83 Hz, 1H), δ 7.48 (d, J=8.43 Hz, 1H), δ 2.67 (t, J=7.32 Hz, 2H), δ1.69 (m, J=7.32 Hz, 7H), δ 1.43 (m, J=7.32 Hz, 2H), δ1.21 (m, J=7.32 Hz, 6H), δ 0.90 (m, 2H)

Example 11. Preparation of Compound 11 ((Z)-2-chloro-4-((2,4-dioxothiazolidin-5-ylidene)methyl)phenyl benzoate)

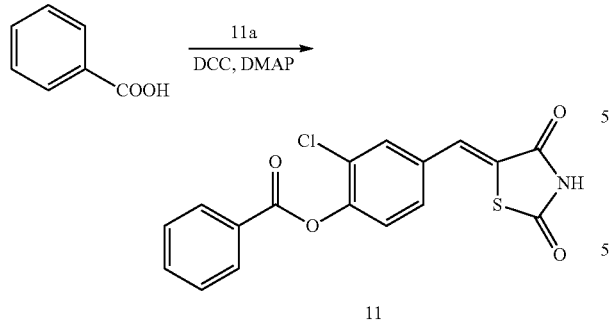

1 g (3.91 mmol) of 11a was added to a round-bottomed flask, and then, 0.478 g (3.91 mmol) of benzoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 71.3%

1H NMR (300 MHz, DMSO-d6) δ 12.72 (s, 1H), δ 8.18 (dd, J=7.32 and 1.47 Hz, 2H), δ 7.92 (d, J=1.47 Hz, 1H), δ 7.84 (t, J=7.32 Hz, 2H), δ7.67 (m, 4H)

Example 12. Preparation of Compound 12 ((Z)-2-chloro-4-((2,4-dioxothiazolidin-5-ylidene)methyl)phenyl 2-phenylacetate)

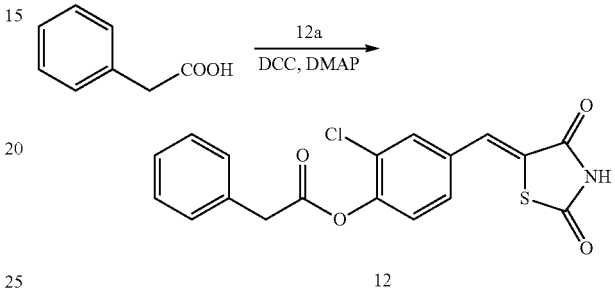

1 g (3.91 mmol) of 12a was added to a round-bottomed flask, and then, 0.533 g (3.91 mmol) of phenylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 90.3%

1H NMR (300 MHz, DMSO-d6) δ 12.72 (s, 1H), δ 7.85 (d, J=2.19 Hz, 1H), δ 7.79 (s, 1H), δ 7.61 (dd, J=8.4 and 2.19 Hz, 1H), δ 7.50 (d, J=8.4 Hz, 1H), δ 7.41 (t, 4H), δ 7.35 (m, 1H), δ 7.06 (s, 2H)

Example 13. Preparation of Compound 13 ((Z)-2-chloro-4-((2,4-dioxothiazolidin-5-ylidene)methyl)phenyl 3-phenylpropanoate)

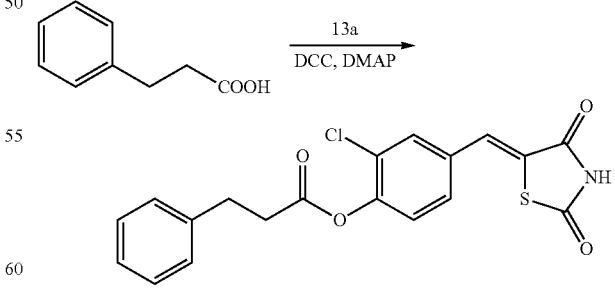

1 g (3.91 mmol) of 13a was added to a round-bottomed flask, and then, 0.587 g (3.91 mmol) of 3-phenylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 92.4%

1H NMR (300 MHz, DMSO-d6) δ 12.72 (s, 1H), δ 7.84 (d, J=2.19 Hz, 1H), δ 7.79 (s, 1H), δ 7.60 (dd, J=8.43 and 2.19 Hz, 1H), δ 7.41 (d, J=8.43 Hz, 1H), δ 7.32 (m, 4H), δ 7.25 (m, 1H), δ 3.00 (s, 4H)

Example 14. Preparation of Compound 14 ((Z)-2-chloro-4-((2,4-dioxothiazolidin-5-ylidene)methyl)phenyl 4-phenylbutanoate)

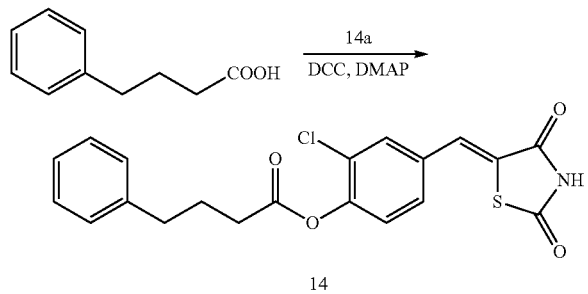

1 g (3.91 mmol) of 14a was added to a round-bottomed flask, and then, 0.642 g (3.91 mmol) of 4-phenylbutyric acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 87%

1H NMR (300 MHz, DMSO-d6) δ 12.72 (s, 1H), δ 7.86 (d, J=1.83 Hz, 1H), δ 7.80 (s, 1H), δ 7.61 (dd, J=8.43 and 1.83 Hz, 1H), δ 7.5 (d, J=8.43 Hz, 1H), δ 7.33 (m, 5H), δ 2.72 (m, J=7.68 Hz, 4H), δ 2.02 (m, 2H)

Example 15. Preparation of Compound 15 ((Z)-2-chloro-4-((2,4-dioxothiazolidin-5-ylidene)methyl)phenyl 5-phenylpentanoate)

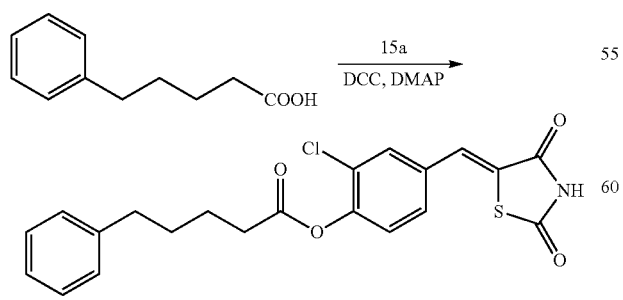

1 g (3.91 mmol) of 15a was added to a round-bottomed flask, and then, 0.697 g (3.91 mmol) of 5-phenylpentanoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.2%

1H NMR (300 MHz, DMSO-d6) δ 12.73 (s, 1H), δ 7.84 (d, J=1.83 Hz, 1H), δ 7.79 (s, 1H), δ 7.60 (dd, J=8.4 and 1.83 Hz, 1H), δ 7.47 (d, J=8.4 Hz, 1H), δ 7.30 (t, J=7.32 Hz, 2H), δ7.21 (m, J=7.32 Hz, 3H), δ 2.74 (t, 4H), δ 1.70 (m, 4H)

Example 16. Preparation of Compound 16 ((Z)-2-bromo-4-((2,4-dioxothiazolidin-5-ylidene)methyl)phenyl cyclopropanecarboxylate)

(1) Synthesis of Reaction Intermediate

First, Compounds 16a to 30a (5-(3-bromo-4-hydroxybenzylidene)-thiazolidine-2,4-dione), which are reactants used for synthesizing Compounds 16 to 30, were synthesized according to the following scheme.

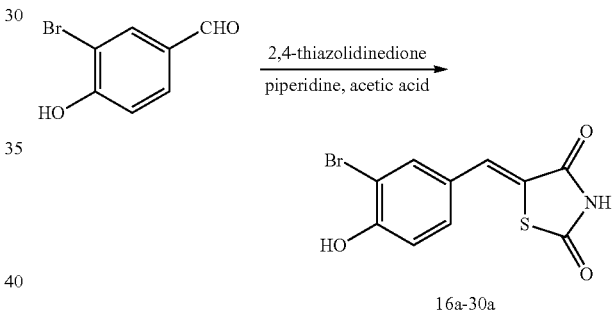

1 g (4.97 mmol) of 3-bromo-4-hydroxybenzaldehyde and 0.583 g (4.97 mmol) of 2,4-thiazolidinedione were placed in a round flask equipped with a Dean-Stark trap, and then dissolved in 20 ml of toluene, which is a reaction solvent, and then, 0.246 ml (2.49 mmol) of piperidine and 0.142 ml (2.49 mmol) of acetic acid were added thereto, followed by the reaction at a temperature of 80° C. for 18 hours or more. The completion of the reaction was confirmed by TLC, and the resulting precipitate was recrystallized and then filtered under reduced pressure to obtain a pure solid.

Yield: 94.1%

1H NMR (300 MHz, DMSO-d6) δ 12.54 (s, 1H), δ 11.16 (s, 1H), δ 7.78 (d, J=2.19 Hz, 1H), δ 7.69 (s, 1H), δ 7.45 (dd, J=8.79 and 2.19 Hz, 1H), δ 7.10 (d, J=8.79 Hz, 1H)

(2) Preparation of Compound 16 ((Z)-2-bromo-4-((2,4-dioxothiazolidin-5-ylidene)methyl)phenyl cyclopropanecarboxylate)

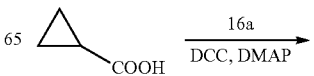

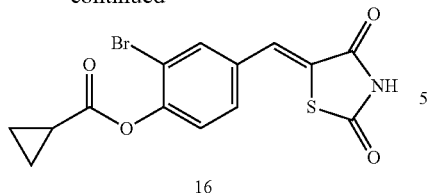

16

1 g (3.33 mmol) of 16a was added to a round-bottomed flask, and then, 0.265 g (3.33 mmol) of cyclopropanecarboxylic acid and 0.034 g (0.28 mmol) of DMAP were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 83.1%

1H NMR (300 MHz, DMSO-d6) δ 12.71 (s, 1H), δ 7.97 (d, J=1.83 Hz, 1H), δ 7.79 (s, 1H), δ 7.63 (dd, J=8.43 and 1.83 Hz, 1H), δ 7.48 (d, J=8.43 Hz, 1H), δ 2.01 (m, 1H), δ 1.16 (m, 4H)

Example 17. Preparation of Compound 17 ((Z)-2-bromo-4-((2,4-dioxothiazolidin-5-ylidene)methyl)phenyl cyclobutanecarboxylate)

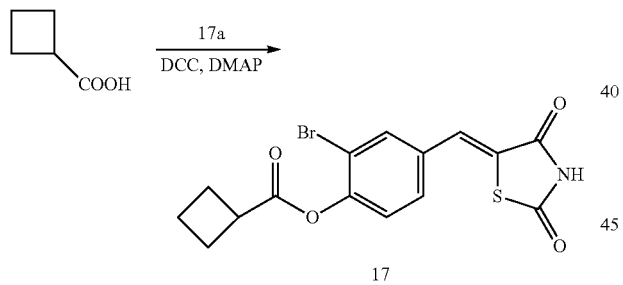

17

1 g (3.33 mmol) of 17a was added to a round-bottomed flask, and then, 0.319 g (3.33 mmol) of cyclobutanecarboxylic acid and 0.034 g (0.28 mmol) of DMAP were added thereto, and then, the result was dissolved in dichloromethane (20 ml), followed by stirring in an ice bath. After 5 minutes, 0.632 g (3.07 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.3%

1H NMR (300 MHz, DMSO-d6) δ 12.69 (s, 1H), δ 7.98 (d, J=1.83 Hz, 1H), δ 7.80 (s, 1H), δ 7.64 (dd, J=8.4 and 1.83 Hz, 1H), δ 7.47 (d, J=8.4 Hz, 1H), δ 3.58 (m, 1H), δ 2.42 (m, 4H), δ 2.10 (m, 2H)

Example 18. Preparation of Compound 18 ((Z)-2-bromo-4-((2,4-dioxothiazolidin-5-ylidene)methyl)phenyl cyclopentanecarboxylate)

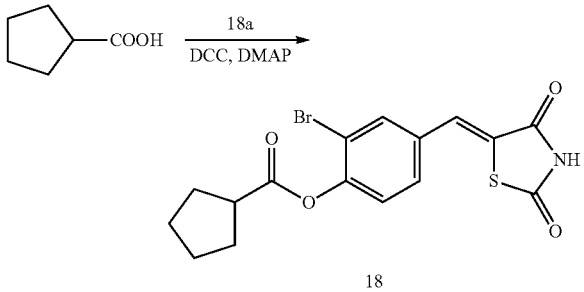

18

1 g (3.33 mmol) of 18a was added to a round-bottomed flask, and then, 0.362 g (3.33 mmol) of cyclopentanecarboxylic acid and 0.034 g (0.28 mmol) of DMAP were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 84.5%

1H NMR (300 MHz, DMSO-d6) δ 12.73 (s, 1H), δ 7.98 (d, J=1.83 Hz, 1H), δ 7.80 (s, 1H), δ 7.64 (dd, J=8.43 and 1.83 Hz, 1H), δ 7.47 (d, J=8.43 Hz, 1H), δ 3.17 (m, J=6.96 Hz, 1H), δ 2.06 (m, J=6.96 Hz, 4H), δ 1.68 (m, J=6.96 Hz, 4H)

Example 19. Preparation of Compound 19 ((Z)-2-bromo-4-((2,4-dioxothiazolidin-5-ylidene)methyl)phenyl 2-cyclopentylacetate)

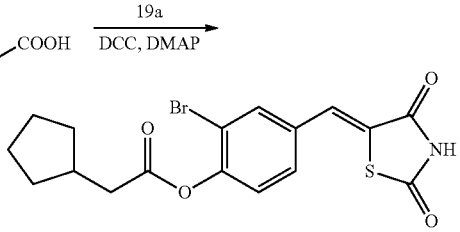

19

1 g (3.33 mmol) of 19a was added to a round-bottomed flask, and then, 0.419 g (3.33 mmol) of cyclopentylacetic acid and 0.034 g (0.28 mmol) of DMAP were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 91.2%

1H NMR (300 MHz, DMSO-d6) δ 12.73 (s, 1H), δ 7.99 (d, J=2.19 Hz, 1H), δ 7.80 (s, 1H), δ 7.64 (dd, J=8.43 and 2.19 Hz, 1H), δ 7.45 (d, J=8.43 Hz, 1H), δ 2.67 (d, J=7.32 Hz, 2H), δ 2.34 (m, J=7.32 Hz, 1H), δ 1.91 (m, J=6.96 Hz, 2H), δ1.66 (m, J=6.96 Hz, 4H), δ 1.30 (m, J=6.96 Hz, 2H)

Example 20. Preparation of Compound 20 ((Z)-2-bromo-4-((2,4-dioxothiazolidin-5-ylidene)methyl) phenyl 3-cyclopentylpropanoate)

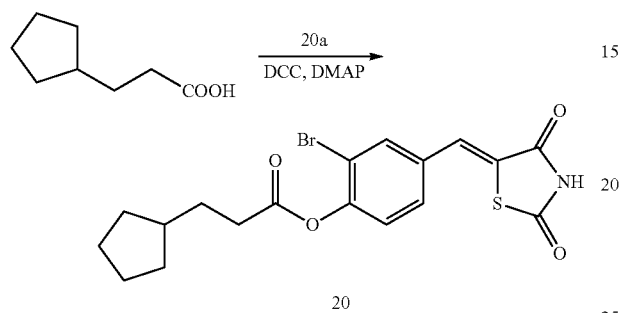

1 g (3.33 mmol) of 20a was added to a round-bottomed flask, and then, 0.476 g (3.33 mmol) of 3-cyclopentylpropionic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 93.4%

1H NMR (300 MHz, DMSO-d6) δ 12.72 (s, 1H), δ 7.98 (d, J=2.19 Hz, 1H), δ 7.80 (s, 1H), δ 7.64 (dd, J=8.43 and 2.19 Hz, 1H), δ 7.46 (d, J=8.43 Hz, 1H), δ 2.68 (t, J=7.32 Hz, 2H), δ 1.90 (m, 9H), 1.15 (m, J=7.32 Hz, 2H)

Example 21. Preparation of Compound 21 ((Z)-2-bromo-4-((2,4-dioxothiazolidin-5-ylidene)methyl) phenyl cyclohexanecarboxylate)

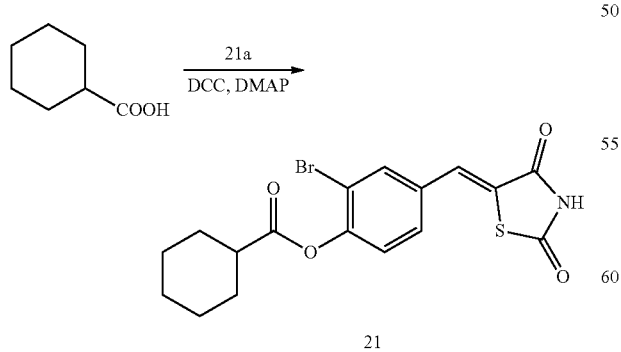

1 g (3.33 mmol) of 21a was added to a round-bottomed flask, and then, 0.427 g (3.33 mmol) of cyclohexanecarboxylic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 83.6%

1H NMR (300 MHz, DMSO-d6) δ 12.72 (s, 1H), δ 7.98 (d, J=2.19 Hz, 1H), δ 7.80 (s, 1H), δ 7.64 (dd, J=8.4 and 2.19 Hz, 1H), δ 7.45 (d, J=8.4 Hz, 1H), δ 2.72 (m, 1H), δ 2.08 (m, 2H), δ1.78 (m, 8H)

Example 22. Preparation of Compound 22 ((Z)-2-bromo-4-((2,4-dioxothiazolidin-5-ylidene)methyl) phenyl 2-cyclohexylacetate)

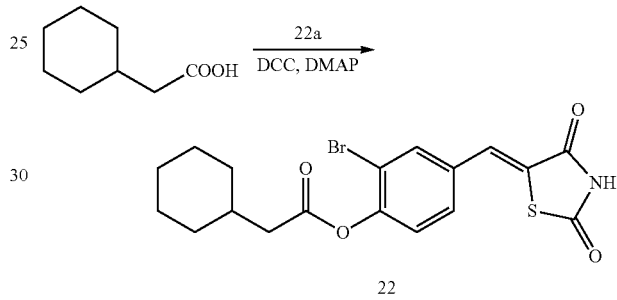

1 g (3.33 mmol) of 22a was added to a round-bottomed flask, and then, 0.474 g (3.33 mmol) of cyclohexylacetic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 88.3%

1H NMR (300 MHz, DMSO-d6) δ 12.72 (s, 1H), δ 7.99 (d, J=2.19 Hz, 1H), δ 7.80 (s, 1H), δ 7.64 (dd, J=8.43 and 2.19 Hz, 1H), δ 7.45 (d, J=8.43 Hz, 1H), δ 2.54 (m, 1H), δ 1.90 (m, 2H), δ1.71 (m, 4H), δ 1.32 (m, 6H)

Example 23. Preparation of Compound 23 ((Z)-2-bromo-4-((2,4-dioxothiazolidin-5-ylidene)methyl) phenyl 3-cyclohexylpropanoate)

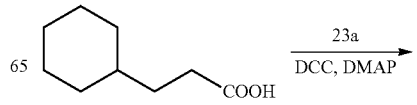

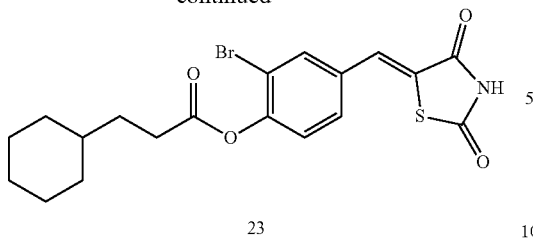

1 g (3.33 mmol) of 23a was added to a round-bottomed flask, and then, 0.521 g (3.33 mmol) of 3-cyclohexylpropionic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 91.1%

1H NMR (300 MHz, DMSO-d6) δ 12.71 (s, 1H), δ 7.98 (d, J=2.19 Hz, 1H), δ 7.80 (s, 1H), δ 7.64 (dd, J=8.4 and 2.19 Hz, 1H), δ 7.45 (d, J=8.4 Hz, 1H), δ 2.68 (m, 2H), δ 1.75 (m, 7H), δ 1.38 (m, 4H), δ 0.96 (m, 2H)

Example 24. Preparation of Compound 24 ((Z)-2-bromo-4-((2,4-dioxothiazolidin-5-ylidene)methyl)phenyl 4-cyclohexylbutanoate)

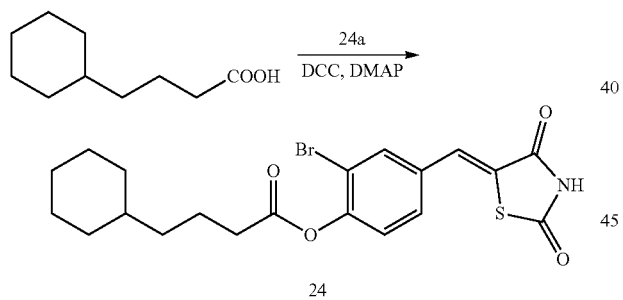

1 g (3.33 mmol) of 24a was added to a round-bottomed flask, and then, 0.567 g (3.33 mmol) of 4-cyclohexylbutyric acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 92.3%

1H NMR (300 MHz, DMSO-d6) δ 12.71 (s, 1H), δ 7.98 (d, J=2.19 Hz, 1H), δ 7.80 (s, 1H), δ 7.65 (dd, J=8.43 and 2.19 Hz, 1H), δ 7.46 (d, J=8.43 Hz, 1H), δ 2.65 (t, 2H), δ 1.71 (m, 7H), δ 1.31 (m, 6H), δ 0.92 (m, 2H)

Example 25. Preparation of Compound 25 ((Z)-2-bromo-4-((2,4-dioxothiazolidin-5-ylidene)methyl)phenyl 5-cyclohexylpentanoate)

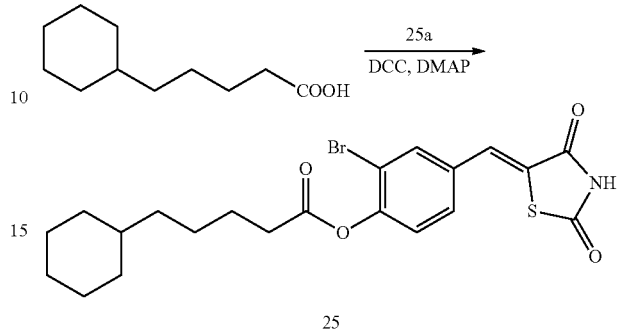

1 g (3.33 mmol) of 25a was added to a round-bottomed flask, and then, 0.64 g (3.33 mmol) of 5-cyclohexylpentanoic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.7%

1H NMR (300 MHz, DMSO-d6) δ 12.70 (s, 1H), δ 7.97 (d, J=1.83 Hz, 1H), δ 7.79 (s, 1H), δ 7.64 (dd, J=8.43 and 1.83 Hz, 1H), δ 7.45 (d, J=8.43 Hz, 1H), δ 2.66 (t, J=7.32 Hz, 2H), δ1.69 (m, 7H), δ 1.43 (m, J=7.32 Hz, 2H), δ1.21 (m, 6H), δ 0.90 (m, 2H)

Example 26. Preparation of Compound 26 ((Z)-2-bromo-4-((2,4-dioxothiazolidin-5-ylidene)methyl)phenylbenzoate)

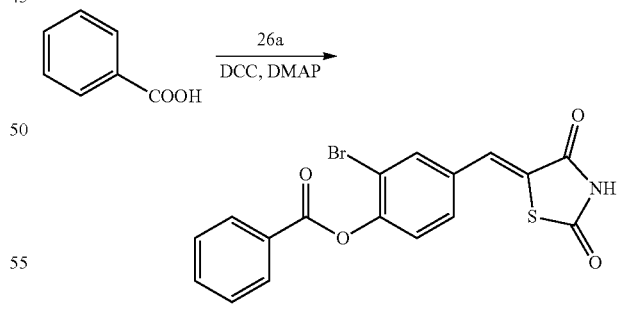

1 g (3.33 mmol) of 26a was added to a round-bottomed flask, and then, 0.407 g (3.33 mmol) of benzoic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 70.5%

1H NMR (300 MHz, DMSO-d6) δ 12.72 (s, 1H), δ 8.18 (d, J=7.32 Hz, 2H), δ 8.04 (d, J=1.83 Hz, 1H), δ 7.83 (t, J=7.32 Hz, 2H), δ 7.71 (m, J=7.32 Hz, 4H)

Example 27. Preparation of Compound 27 ((Z)-2-bromo-4-((2,4-dioxothiazolidin-5-ylidene)methyl)phenyl 2-phenylacetate)

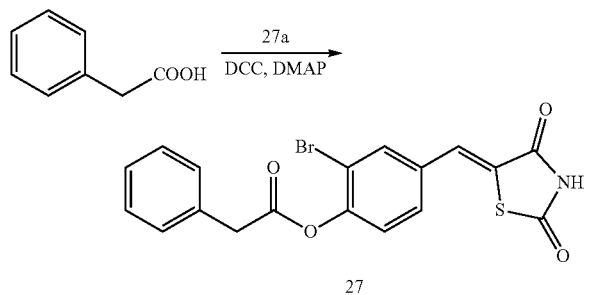

1 g (3.33 mmol) of 27a was added to a round-bottomed flask, and then, 0.454 g (3.33 mmol) of phenylacetic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N,N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.5%

1H NMR (300 MHz, DMSO-d6) δ 12.71 (s, 1H), δ 7.97 (d, J=2.19 Hz, 1H), δ 7.79 (s, 1H), δ 7.66 (dd, J=8.43 and 2.19 Hz, 1H), δ 7.48 (d, J=8.43 Hz, 1H), δ 7.42 (m, 5H), δ 4.06 (s, 2H)

Example 28. Preparation of Compound 28 ((Z)-2-bromo-4-((2,4-dioxothiazolidin-5-ylidene)methyl)phenyl 3-phenylpropanoate)

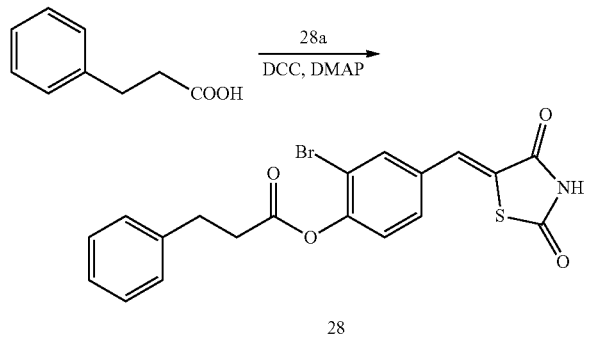

1 g (3.33 mmol) of 28a was added to a round-bottomed flask, and then, 0.5 g (3.33 mmol) of 3-phenylpropionic acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N,N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 88.9%

1H NMR (300 MHz, DMSO-d6) δ 12.72 (s, 1H), δ 7.98 (d, J=2.19 Hz, 1H), δ 7.79 (s, 1H), δ 7.64 (dd, J=8.43 and 2.19 Hz, 1H), δ 7.39 (d, J=8.43 Hz, 1H), δ 7.32 (m, 4H), δ 7.26 (m, 1H), δ 3.00 (s, 4H)

Example 29. Preparation of Compound 29 ((Z)-2-bromo-4-((2,4-dioxothiazolidin-5-ylidene)methyl)phenyl 4-phenylbutanoate)

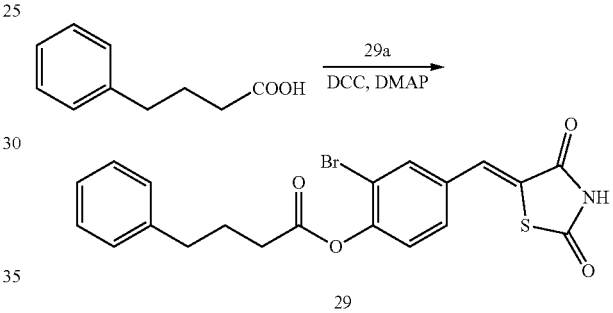

1 g (3.33 mmol) of 29a was added to a round-bottomed flask, and then, 0.547 g (3.33 mmol) of 4-phenylbutyric acid and 0.034 g (0.28 mmol) of 4-(dimethylamino)pyridine (DMAP) were added thereto, and then, the result was dissolved in dichloromethane (20 ml), followed by stirring in an ice bath. After 5 minutes, 0.632 g (3.07 mmol) of N,N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 82.6%

1H NMR (300 MHz, DMSO-d6) δ 12.70 (s, 1H), δ 7.98 (d, J=1.83 Hz, 1H), δ 7.80 (s, 1H), δ 7.64 (dd, J=8.43 and 1.83 Hz, 1H), δ 7.46 (d, J=8.43 Hz, 1H), δ 7.33 (m, 5H), δ 2.73 (m, J=7.32 Hz, 4H), δ 2.03 (m, J=7.32 Hz, 2H)

Example 30. Preparation of Compound 30 ((Z)-2-bromo-4-((2,4-dioxothiazolidin-5-ylidene)methyl)phenyl 5-phenylpentanoate)

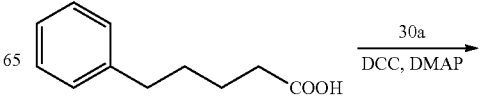

-continued

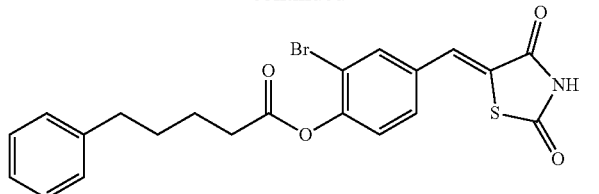

30

1 g (3.33 mmol) of 30a was added to a round-bottomed flask, and then, 0.594 g (3.33 mmol) of 5-phenylpentanoic acid and 0.04 g (0.33 mmol) of DMAP (4-(dimethylamino) pyridine) were added thereto, and then, the result was dissolved in dichloromethane (20 ml), followed by stirring in an ice bath. After 5 minutes, 0.632 g (3.07 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 78.3%

1H NMR (300 MHz, DMSO-d6) δ 12.71 (s, 1H), δ 7.97 (d, J=2.19 Hz, 1H), δ 7.79 (s, 1H), δ 7.64 (dd, J=8.43 and 2.19 Hz, 1H), δ 7.45 (d, J=8.43 Hz, 1H), δ 7.31 (m, 5H), δ 2.68 (m, 4H), δ 1.71 (m, 4H)

Example 31. Preparation of Compound 31 ((Z)-4-((2,4-dioxothiazolidin-5-ylidene)methyl)-2-methoxyphenyl cyclopropanecarboxylate)

(1) Preparation of Reaction Intermediate

First, Compounds 31a to 45a (5-(4-hydroxy-3-methoxy-benzylidene)-thiazolidine-2,4-dione), which are reactants used for synthesizing Compounds 31 to 45, were synthesized according to the following scheme.

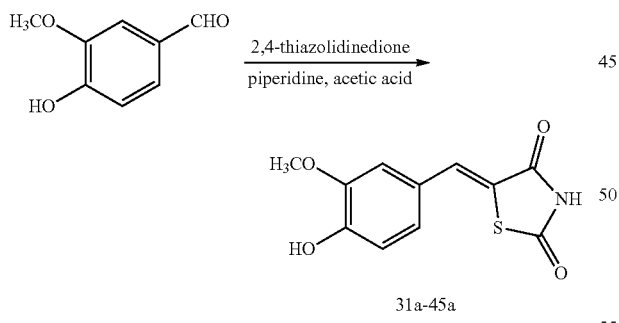

31a-45a 1 g (6.57 mmol) of 3-methoxy-4-hydroxybenzaldehyde and 0.77 g (6.57 mmol) of 2,4-thiazolidinedione were placed in a round flask equipped with a Dean-Stark trap, and then dissolved in 20 ml of toluene, which is a reaction solvent, and then, 0.325 ml (3.29 mmol) of piperidine and 0.188 ml (3.29 mmol) of acetic acid were added thereto, followed by the reaction at a temperature of 80° C. for 18 hours or more. The completion of the reaction was confirmed by TLC, and the resulting precipitate was recrystallized and then filtered under reduced pressure to obtain a pure solid.

Yield: 94.3%

1H NMR (300 MHz, DMSO-d6) δ 12.47 (s, 1H), δ 9.96 (s, 1H), δ 7.71 (s, 1H), δ 7.17 (d, J=1.83 Hz, 1H), δ 7.08 (dd, J=8.04 and 1.83 Hz, 1H), δ 6.93 (d, J=8.04 Hz, 1H), δ 3.86 (s, 3H)

(2) Preparation of Compound 31 ((Z)-4-((2,4-dioxothiazolidin-5-ylidene)methyl)-2-methoxyphenyl cyclopropanecarboxylate)

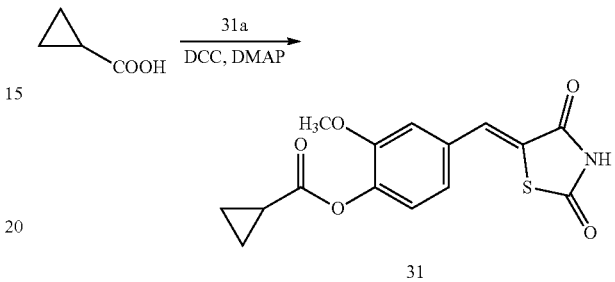

31

1 g (3.98 mmol) of 31a was added to a round-bottomed flask, and then, 0.317 g (3.98 mmol) of cyclopropanecarboxylic acid, and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 76.2%

1H NMR (300 MHz, DMSO-d6) δ 12.65 (s, 1H), δ 7.80 (s, 1H), δ 7.37 (d, J=1.83 Hz, 1H), δ 7.28 (d, J=8.04 Hz, 1H), δ 7.19 (dd, J=8.04 and 1.83 Hz, 1H), δ 3.82 (s, 3H), δ 1.95 (m, J=3.3 Hz, 1H), δ 1.15 (m, J=3.3 Hz, 4H)

Example 32. Preparation of Compound 32 ((Z)-4-((2,4-dioxothiazolidin-5-ylidene)methyl)-2-methoxyphenyl cyclobutanecarboxylate)

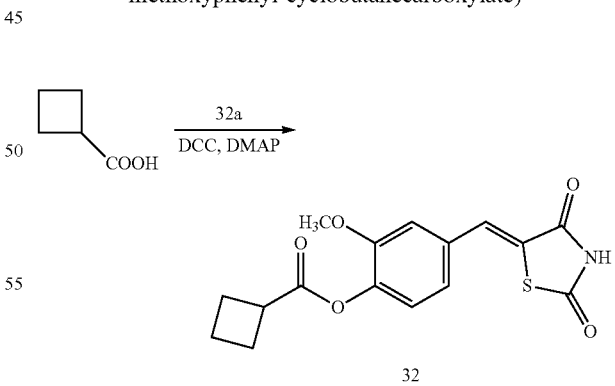

32

1 g (3.98 mmol) of 32a was added to a round-bottomed flask, and then, 0.381 g (3.98 mmol) of cyclobutanecarboxylic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.6%

1H NMR (300 MHz, DMSO-d6) δ 12.66 (s, 1H), δ 7.81 (s, 1H), δ 7.37 (d, J=1.83 Hz, 1H), δ 7.27 (d, J=8.43 Hz, 1H), δ 7.19 (dd, J=8.43 and 1.83 Hz, 1H), δ 3.81 (s, 3H), δ 3.51 (m, 1H), δ 2.35 (m, 4H), δ 2.07 (m, 2H)

Example 33. Preparation of Compound 33 ((Z)-4-((2,4-dioxothiazolidin-5-ylidene)methyl)-2-methoxyphenyl cyclopentanecarboxylate)

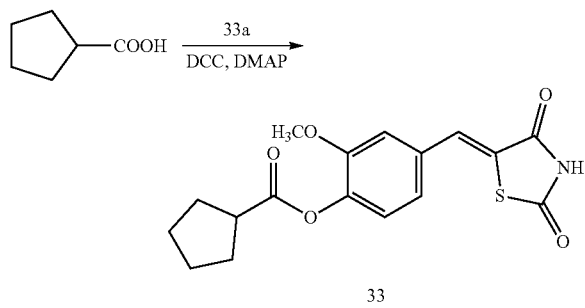

1 g (3.98 mmol) of 33a was added to a round-bottomed flask, and then, 0.433 g (3.98 mmol) of cyclopentanecarboxylic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 83.5%

1H NMR (300 MHz, DMSO-d6) δ 12.65 (s, 1H), δ 7.80 (s, 1H), δ 7.37 (d, J=1.83 Hz, 1H), δ 7.27 (d, J=8.43 Hz, 1H), δ 7.19 (dd, J=8.43 and 1.83 Hz, 1H), δ 3.81 (s, 3H), δ 3.10 (m, 1H), δ 1.99 (m, 4H), δ 1.69 (m, 4H)

Example 34. Preparation of Compound 34 ((Z)-4-((2,4-dioxothiazolidin-5-ylidene)methyl)-2-methoxyphenyl 2-cyclopentylacetate)

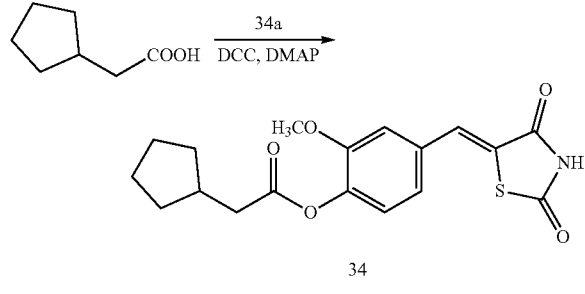

1 g (3.98 mmol) of 34a was added to a round-bottomed flask, and then, 0.5 g (3.98 mmol) of cyclopentylacetic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.7%

1H NMR (300 MHz, DMSO-d6) δ 12.65 (s, 1H), δ 7.80 (s, 1H), δ 7.37 (d, J=1.83 Hz, 1H), δ 7.26 (d, J=8.07 Hz, 1H), δ 7.19 (dd, J=8.07 and 1.83 Hz, 1H), δ 3.81 (s, 3H), δ 2.59 (d, J=7.32 Hz, 2H), δ 2.32 (m, J=7.32 Hz, 1H), δ 1.88 (m, J=6.96 Hz, 2H), δ 1.67 (m, 4H), δ 1.28 (m, J=6.96 Hz, 2H)

Example 35. Preparation of Compound 35 ((Z)-4-((2,4-dioxothiazolidin-5-ylidene)methyl)-2-methoxyphenyl 3-cyclopentylpropanoate)

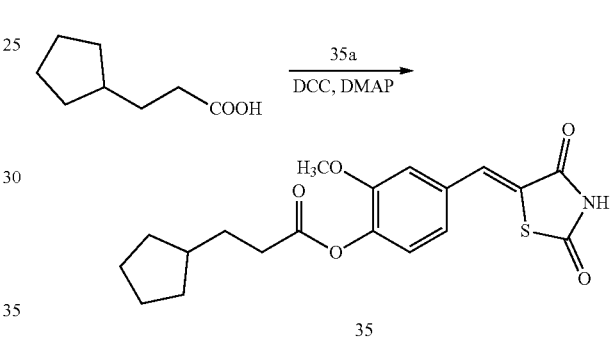

1 g (3.98 mmol) of 35a was added to a round-bottomed flask, and then, 0.568 g (3.98 mmol) of 3-cyclopentylpropionic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 88.8%

1H NMR (300 MHz, DMSO-d6) δ 12.66 (s, 1H), δ 7.80 (s, 1H), δ 7.37 (d, J=1.47 Hz, 1H), δ 7.26 (d, J=8.4 Hz, 1H), δ 7.19 (dd, J=8.4 and 1.47 Hz, 1H), δ 3.81 (s, 3H), δ 2.60 (d, J=7.32 Hz, 2H), δ1.89 (m, J=7.32 Hz, 3H), δ 1.68 (m, J=7.32 Hz, 6H), δ 1.15 (m, J=7.32 Hz, 2H)

Example 36. Preparation of Compound 36 ((Z)-4-((2,4-dioxothiazolidin-5-ylidene)methyl)-2-methoxyphenyl cyclohexanecarboxylate)

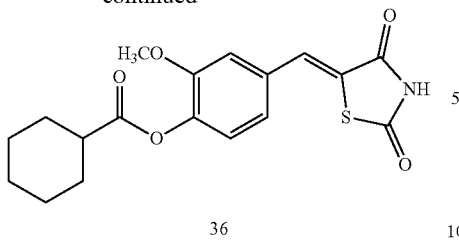

36

1 g (3.98 mmol) of 36a was added to a round-bottomed flask, and then, 0.510 g (3.98 mmol) of cyclohexanecarboxylic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 85.3%

1H NMR (300 MHz, DMSO-d6) δ 12.64 (s, 1H), δ 7.80 (s, 1H), δ 7.37 (d, J=1.83 Hz, 1H), δ 7.25 (d, J=8.07 Hz, 1H), δ 7.19 (dd, J=8.07 and 1.83 Hz, 1H), δ 3.81 (s, 3H), δ 1.98 (m, 2H), δ 1.71 (m, 2H), δ1.64 (m, 1H), δ 1.51 (m, 2H), δ 1.36 (m, 4H)

Example 37. Preparation of Compound 37 ((Z)-4-((2,4-dioxothiazolidin-5-ylidene)methyl)-2-methoxyphenyl 2-cyclohexylacetate)

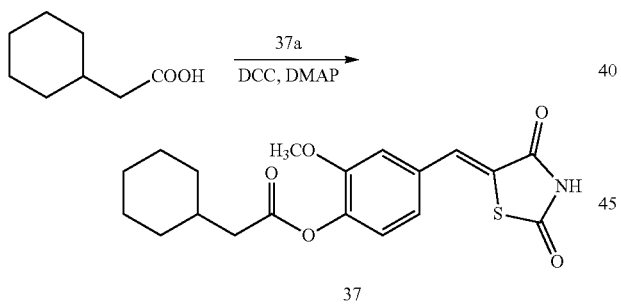

37

1 g (3.98 mmol) of 37a was added to a round-bottomed flask, and then, 0.566 g (3.98 mmol) of cyclohexylacetic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 90.2%

1H NMR (300 MHz, DMSO-d6) δ 12.66 (s, 1H), δ 7.80 (s, 1H), δ 7.37 (d, J=1.83 Hz, 1H), δ 7.25 (d, J=8.04 Hz, 1H), δ 7.19 (dd, J=8.04 and 1.83 Hz, 1H), δ 3.80 (s, 3H), δ 2.46 (d, 2H), δ1.85 (m, 6H), δ 1.32 (m, 5H)

Example 38. Preparation of Compound 38 ((Z)-4-((2,4-dioxothiazolidin-5-ylidene)methyl)-2-methoxyphenyl 3-cyclohexylpropanoate)

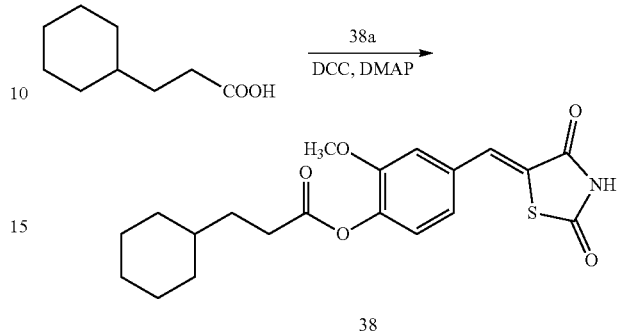

38

1 g (3.98 mmol) of 38a was added to a round-bottomed flask, and then, 0.622 g (3.98 mmol) of 3-cyclohexylpropionic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 93.8%

1H NMR (300 MHz, DMSO-d6) δ 12.64 (s, 1H), δ 7.80 (s, 1H), δ 7.37 (d, J=1.47 Hz, 1H), δ 7.26 (d, J=8.43 Hz, 1H), δ 7.19 (dd, J=8.43 and 1.47 Hz, 1H), δ 3.81 (s, 3H), δ 2.60 (t, 2H), δ1.74 (m, 7H), δ 1.33 (m, 4H), δ 0.95 (m, 2H)

Example 39. Preparation of Compound 39 ((Z)-4-((2,4-dioxothiazolidin-5-ylidene)methyl)-2-methoxyphenyl 4-cyclohexylbutanoate)

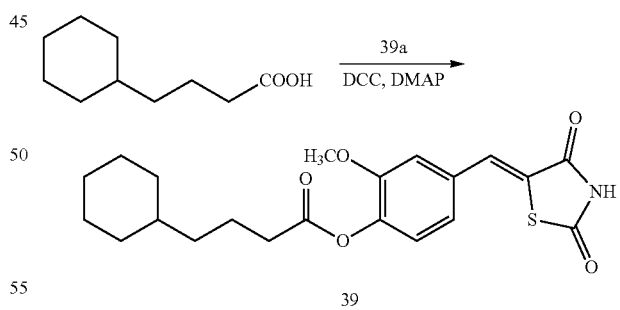

39

1 g (3.98 mmol) of 39a was added to a round-bottomed flask, and then, 0.678 g (3.98 mmol) of 4-cyclohexylbutyric acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 90.7%

1H NMR (300 MHz, DMSO-d6) δ 12.28 (s, 1H), δ 7.43 (s, 1H), δ 7.00 (d, J=1.83 Hz, 1H), δ 6.89 (d, J=8.4 Hz, 1H), δ 6.82 (dd, J=8.4 and 1.83 Hz, 1H), δ 3.44 (s, 3H), δ 2.14 (t, 2H), δ1.34 (m, 7H), δ 0.90 (m, 6H), δ 0.55 (m, 2H)

Example 40. Preparation of Compound 40 ((Z)-4-((2,4-dioxothiazolidin-5-ylidene)methyl)-2-methoxyphenyl 5-cyclohexylpentanoate)

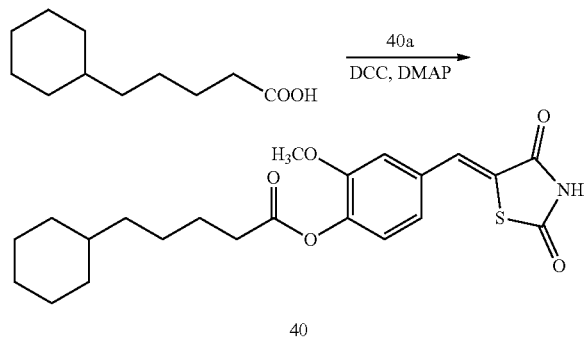

1 g (3.98 mmol) of 40a was added to a round-bottomed flask, and then, 0.764 g (3.98 mmol) of 5-cyclohexylpentanoic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 79.9%

1H NMR (300 MHz, DMSO-d6) δ 12.64 (s, 1H), δ 7.80 (s, 1H), δ 7.37 (d, J=1.83 Hz, 1H), δ 7.25 (d, J=8.07 Hz, 1H), δ 7.19 (dd, J=8.07 and 1.83 Hz, 1H), δ 3.81 (s, 3H), δ 2.59 (t, 2H), δ1.70 (m, 7H), δ 1.42 (m, 2H), δ1.21 (m, 6H), δ 0.90 (m, 2H)

Example 41. Preparation of Compound 41 ((Z)-4-((2,4-dioxothiazolidin-5-ylidene)methyl)-2-methoxyphenyl benzoate)

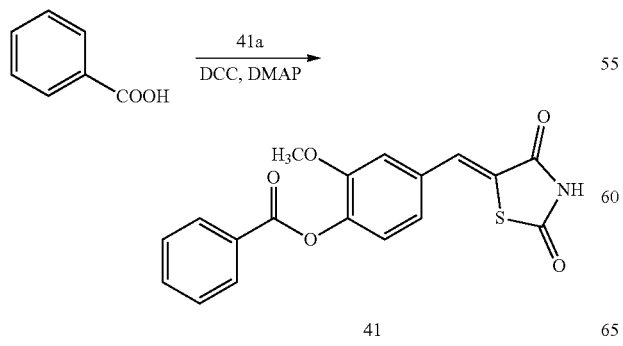

1 g (3.98 mmol) of 41a was added to a round-bottomed flask, and then, 0.486 g (3.98 mmol) of benzoic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 73.7%

1H NMR (300 MHz, DMSO-d6) δ 12.65 (s, 1H), δ 8.13 (d, J=7.32 Hz, 2H), δ 7.84 (s, 1H), δ 7.79 (t, J=7.32 Hz, 1H), δ 7.64 (t, J=7.32 Hz, 2H), δ7.44 (m, 2H), δ 7.26 (d, 1H), δ 3.82 (s, 3H)

Example 42. Preparation of Compound 42 ((Z)-4-((2,4-dioxothiazolidin-5-ylidene)methyl)-2-methoxyphenyl 2-phenylacetate)

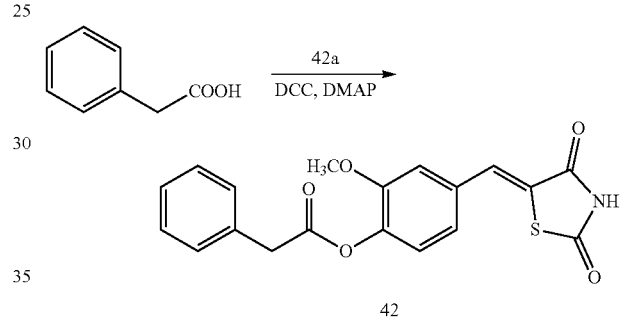

1 g (3.98 mmol) of 42a was added to a round-bottomed flask, and then, 0.542 g (3.98 mmol) of phenylacetic acid and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 81.2%

1H NMR (300 MHz, DMSO-d6) δ 12.65 (s, 1H), δ 7.80 (s, 1H), δ 7.38 (d, J=4.38 Hz, 5H), δ 7.34 (m, J=4.38 Hz, 2H), δ7.19 (d, 1H), δ 3.98 (s, 2H), δ3.79 (s, 3H)

Example 43. Preparation of Compound 43 ((Z)-4-((2,4-dioxothiazolidin-5-ylidene)methyl)-2-methoxyphenyl 3-phenylpropanoate)

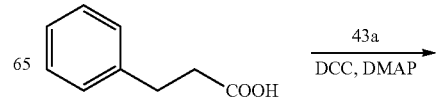

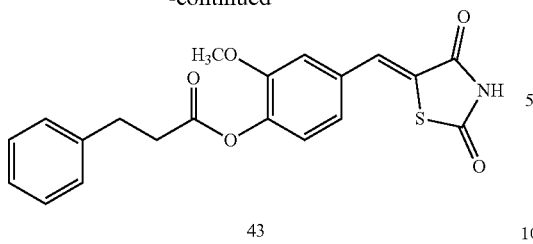

43

1 g (3.98 mmol) of 43a was added to a round-bottomed flask, and then, 0.598 g (3.98 mmol) of 3-phenylpropionic acid and 0.04 g (0.33 mmol) of DMAP (4-(dimethylamino) pyridine) were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 85.6%

1H NMR (300 MHz, DMSO-d6) δ 12.65 (s, 1H), δ 7.80 (s, 1H), δ 7.37 (m, 5H), δ 7.26 (m, 3H), δ 3.83 (s, 3H), δ 3.00 (m, 4H)

Example 44. Preparation of Compound 44 ((Z)-4-((2,4-dioxothiazolidin-5-ylidene)methyl)-2-methoxyphenyl 4-phenylbutanoate)

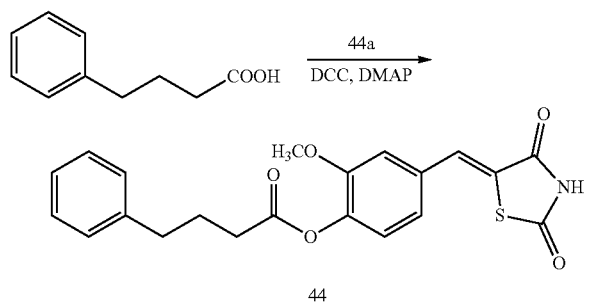

44

1 g (3.98 mmol) of 44a was added to a round-bottomed flask, and then, 0.654 g (3.98 mmol) of 4-phenylbutyric acid and 0.04 g (0.33 mmol) of DMAP were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 92.5%

1H NMR (300 MHz, DMSO-d6) δ 12.66 (s, 1H), δ 7.81 (s, 1H), δ 7.38 (d, 1H), δ 7.33 (m, 7H), δ 3.82 (s, 3H), δ 2.68 (t, J=7.32 Hz, 2H), δ 2.58 (t, J=7.32 Hz, 2H), δ 1.98 (m, J=7.32 Hz, 2H)

Example 45. Preparation of Compound 45 ((Z)-4-((2,4-dioxothiazolidin-5-ylidene)methyl)-2-methoxyphenyl 5-phenylpentanoate)

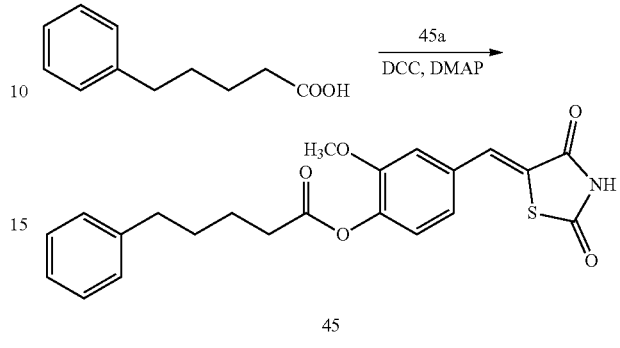

45

1 g (3.98 mmol) of 45a was added to a round-bottomed flask, and then, 0.709 g (3.98 mmol) of 5-phenylpentanoic acid and 0.04 g (0.33 mmol) of DMAP were added thereto, and then, the result was dissolved in dichloromethane (20 ml), followed by stirring in an ice bath. After 5 minutes, 0.755 g (3.66 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 80.9%

1H NMR (300 MHz, DMSO-d6) δ 12.66 (s, 1H), δ 7.80 (s, 1H), δ 7.37 (d, 1H), δ 7.31 (m, 7H), δ 3.78 (s, 3H), δ 2.62 (m, 4H), δ 1.67 (m, 4H)

Example 46. Preparation of Compound 46 ((Z)-4-((2,4-dioxothiazolidin-5-ylidene)methyl)-2-ethoxyphenyl cyclopropanecarboxylate)

(1) Preparation of Reaction Intermediate

First, Compounds 46a to 60a (5-(3-ethoxy-4-hydroxybenzylidene)-thiazolidine-2,4-dione), which are reactants used for synthesizing Compounds 46 to 60, were synthesized according to the following scheme.

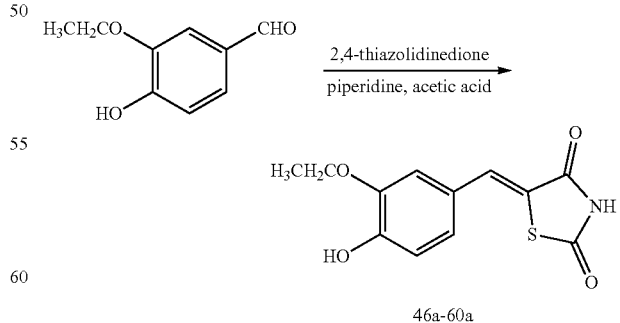

46a-60a 1 g (6.02 mmol) of 3-ethoxy-4-hydroxybenzaldehyde and 0.705 g (6.02 mmol) of 2,4-thiazolidinedione were placed in a round flask equipped with a Dean-Stark trap, and then dissolved in 20 ml of toluene, which is a reaction solvent, and then, 0.297 ml (3.00 mmol) of piperidine and 0.172 ml (3.00 mmol) of acetic acid were added thereto, followed by the reaction at a temperature of 80° C. for 18 hours or more. The completion of the reaction was confirmed by TLC, and the resulting precipitate was recrystallized and then filtered under reduced pressure to obtain a pure solid.

Yield: 90.4%

1H NMR (300 MHz, DMSO-d6) δ 12.46 (s, 1H), δ 9.88 (s, 1H), δ 7.69 (s, 1H), δ 7.15 (d, J=1.83 Hz, 1H), δ 7.07 (dd, J=8.43 and 1.83 Hz, 1H), δ 6.94 (d, J=8.43 Hz, 1H), δ 4.10 (m, J=6.96 Hz, 2H), δ 1.37 (t, J=6.96 Hz, 3H)

(2) Preparation of Compound 46 ((Z)-4-((2,4-dioxothiazolidin-5-ylidene)methyl)-2-ethoxyphenyl cyclopropanecarboxylate)

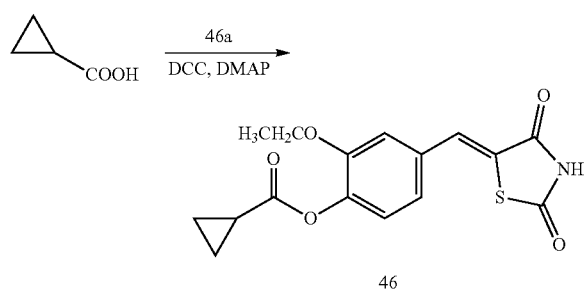

1 g (3.77 mmol) of 46a was added to a round-bottomed flask, and then, 0.3 g (3.77 mmol) of cyclopropanecarboxylic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 83.2%

1H NMR (300 MHz, DMSO-d6) δ 12.64 (s, 1H), δ 7.78 (s, 1H), δ 7.33 (d, J=1.83 Hz, 1H), δ 7.27 (d, J=8.43 Hz, 1H), δ 7.17 (dd, J=8.43 and 1.83 Hz, 1H), δ 4.10 (m, J=6.96 Hz, 2H), δ 1.92 (m, 1H), δ 1.32 (t, J=6.96 Hz, 3H), δ 1.07 (m, 4H)

Example 47. Preparation of Compound 47 ((Z)-4-((2,4-dioxothiazolidin-5-ylidene)methyl)-2-ethoxyphenyl cyclobutanecarboxylate)

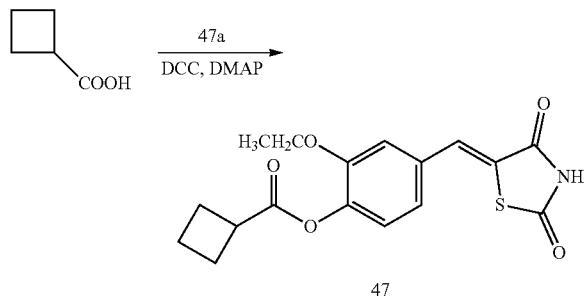

1 g (3.77 mmol) of 47a was added to a round-bottomed flask, and then, 0.360 g (3.77 mmol) of cyclobutanecarboxylic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.1%

1H NMR (300 MHz, DMSO-d6) δ 12.63 (s, 1H), δ 7.79 (s, 1H), δ 7.34 (d, J=1.83 Hz, 1H), δ 7.26 (d, J=8.07 Hz, 1H), δ 7.18 (dd, J=8.07 and 1.83 Hz, 1H), δ 4.11 (m, J=6.96 Hz, 2H), δ3.50 (m, J=8.4 Hz, 1H), δ 2.35 (m, 4H), δ 2.08 (m, J=8.4 Hz, 2H), δ1.35 (t, J=6.96 Hz, 3H)

Example 48. Preparation of Compound 48 ((Z)-4-((2,4-dioxothiazolidin-5-ylidene)methyl)-2-ethoxyphenyl cyclopentanecarboxylate)

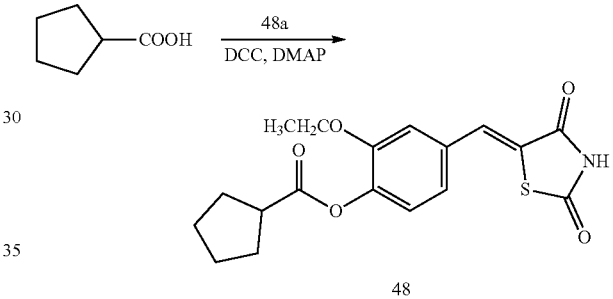

1 g (3.77 mmol) of 48a was added to a round-bottomed flask, and then, 0.410 g (3.77 mmol) of cyclopentanecarboxylic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 79.6%

1H NMR (300 MHz, DMSO-d6) δ 12.63 (s, 1H), δ 7.78 (s, 1H), δ 7.33 (d, J=1.83 Hz, 1H), δ 7.26 (d, J=8.04 Hz, 1H), δ 7.18 (dd, J=8.04 and 1.83 Hz, 1H), δ 4.09 (m, J=6.96 Hz, 2H), δ3.09 (m, 1H), δ 1.96 (m, 4H), δ 1.68 (m, 4H), δ 1.32 (t, J=6.96 Hz, 3H)

Example 49. Preparation of Compound 49 ((Z)-4-((2,4-dioxothiazolidin-5-ylidene)methyl)-2-ethoxyphenyl 2-cyclopentylacetate)

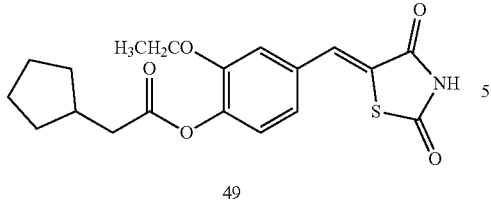

49

1 g (3.77 mmol) of 49a was added to a round-bottomed flask, and then, 0.474 g (3.77 mmol) of cyclopentylacetic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 76.6%

1H NMR (300 MHz, DMSO-d6) δ 12.65 (s, 1H), δ 7.79 (s, 1H), δ 7.34 (d, J=1.47 Hz, 1H), δ 7.24 (d, J=8.43 Hz, 1H), δ 7.17 (dd, J=8.43 and 1.47 Hz, 1H), δ 4.11 (m, J=6.96 Hz, 2H), δ 2.57 (d, J=7.32 Hz, 2H), δ 2.32 (m, J=7.32 Hz, 1H), δ 1.89 (m, 2H), δ1.67 (m, 4H), δ 1.32 (t, J=6.96 Hz, 3H), δ 1.24 (m, 2H)

Example 50. Preparation of Compound 50 ((Z)-4-((2,4-dioxothiazolidin-5-ylidene)methyl)-2-ethoxyphenyl 3-cyclopentylpropanoate)

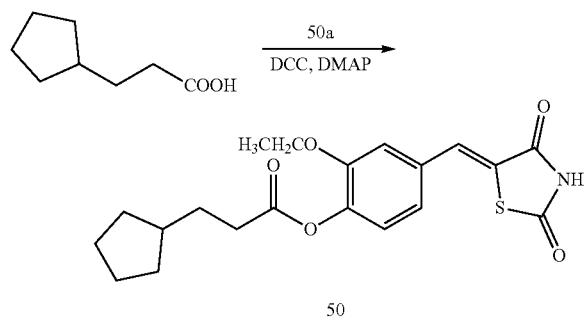

50

1 g (3.77 mmol) of 50a was added to a round-bottomed flask, and then, 0.538 g (3.77 mmol) of 3-cyclopentylpropionic acid and 0.038 g (0.32 mmol) of 4-(dimethylamino) pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 90.2%

1H NMR (300 MHz, DMSO-d6) δ 12.64 (s, 1H), δ 7.79 (s, 1H), δ 7.34 (d, J=1.83 Hz, 1H), δ 7.25 (d, J=8.4 Hz, 1H), δ 7.18 (dd, J=8.4 and 1.83 Hz, 1H), δ 4.11 (m, J=6.96 Hz, 2H), δ 2.59 (t, 2H), δ1.92 (m, 9H), δ 1.32 (t, J=6.96 Hz, 3H), δ 1.15 (m, 2H)

Example 51. Preparation of Compound 51 ((Z)-4-((2,4-dioxothiazolidin-5-ylidene)methyl)-2-ethoxyphenyl cyclohexanecarboxylate)

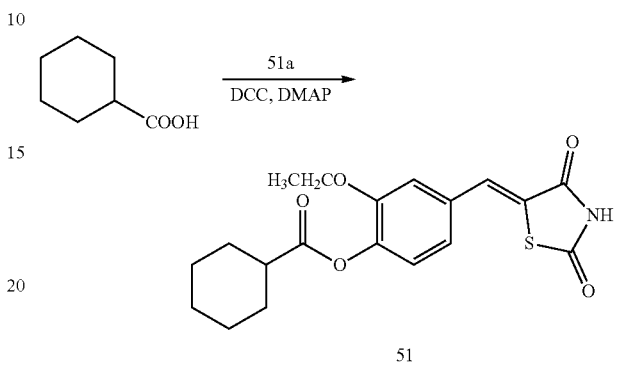

51

1 g (3.77 mmol) of 51a was added to a round-bottomed flask, and then, 0.483 g (3.77 mmol) of cyclohexanecarboxylic acid and 0.038 g (0.32 mmol) of 4-(dimethylamino) pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.6%

1H NMR (300 MHz, DMSO-d6) δ 12.64 (s, 1H), δ 7.79 (s, 1H), δ 7.33 (d, J=1.83 Hz, 1H), δ 7.24 (d, J=8.4 Hz, 1H), δ 7.18 (dd, J=8.4 and 1.83 Hz, 1H), δ 4.10 (m, J=6.96 Hz, 2H), δ 2.66 (m, 1H), δ 1.97 (m, 2H), δ 1.75 (m, 2H), δ1.62 (m, 3H), δ 1.41 (m, 3H), δ 1.32 (t, J=6.96 Hz, 3H)

Example 52. Preparation of Compound 52 ((Z)-4-((2,4-dioxothiazolidin-5-ylidene)methyl)-2-ethoxyphenyl 2-cyclohexylacetate)

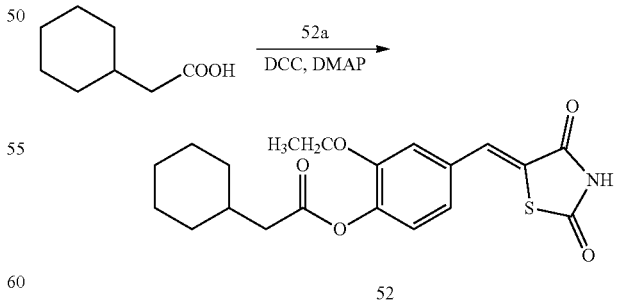

52

1 g (3.77 mmol) of 52a was added to a round-bottomed flask, and then, 0.536 g (3.77 mmol) of cydohexylacetic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.7%

1H NMR (300 MHz, DMSO-d6) δ 12.64 (s, 1H), δ 7.79 (s, 1H), δ 7.34 (d, J=1.44 Hz, 1H), δ 7.24 (d, J=8.43 Hz, 1H), δ 7.18 (dd, J=8.43 and 1.44 Hz, 1H), δ 4.11 (m, J=6.96 Hz, 2H), δ 2.45 (d, 2H), δ1.84 (m, 3H), δ 1.70 (m, 2H), δ1.32 (t, J=6.96 Hz, 3H), δ 1.23 (m, 6H)

Example 53. Preparation of Compound 53 ((Z)-4-((2,4-dioxothiazolidin-5-ylidene)methyl)-2-ethoxyphenyl 3-cyclohexylpropanoate)

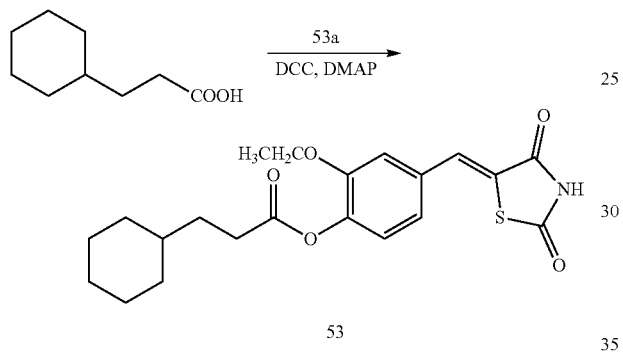

53

1 g (3.77 mmol) of 53a was added to a round-bottomed flask, and then, 0.589 g (3.77 mmol) of 3-cyclohexylpropionic acid and 0.038 g (0.32 mmol) of DMAP (4-(dimethylamino)pyridine) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 90.6%

1H NMR (300 MHz, DMSO-d6) δ 12.64 (s, 1H), δ 7.79 (s, 1H), δ 7.35 (d, J=1.83 Hz, 1H), δ 7.25 (d, J=8.43 Hz, 1H), δ 7.18 (dd, J=8.43 and 1.83 Hz, 1H), δ 4.11 (m, J=6.96 Hz, 2H), δ 2.60 (t, J=7.32 Hz, 2H), δ1.75 (m, 8H), δ 1.32 (t, J=6.96 Hz, 3H), δ 1.22 (m, 3H), δ 0.95 (m, 2H)

Example 54. Preparation of Compound 54 ((Z)-4-((2,4-dioxothiazolidin-5-ylidene)methyl)-2-ethoxyphenyl 4-cyclohexylbutanoate)

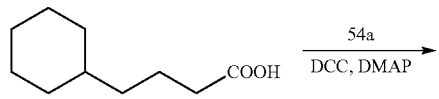

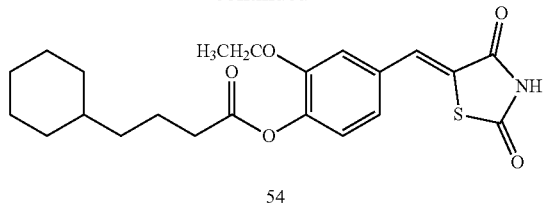

54

1 g (3.77 mmol) of 54a was added to a round-bottomed flask, and then, 0.642 g (3.77 mmol) of 4-cyclohexylbutyric acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 93.5%

1H NMR (300 MHz, DMSO-d6) δ 12.64 (s, 1H), δ 7.79 (s, 1H), δ 7.34 (d, J=1.83 Hz, 1H), δ 7.25 (d, J=8.43 Hz, 1H), δ 7.18 (dd, J=8.43 and 1.83 Hz, 1H), δ 4.11 (m, J=6.96 Hz, 2H), δ1.66 (m, 8H), δ 1.32 (t, J=6.96 Hz, 3H), δ 1.18 (m, 7H), δ 0.88 (m, 2H)

Example 55. Preparation of Compound 55 ((Z)-4-((2,4-dioxothiazolidin-5-ylidene)methyl)-2-ethoxyphenyl 5-cyclohexylpentanoate)

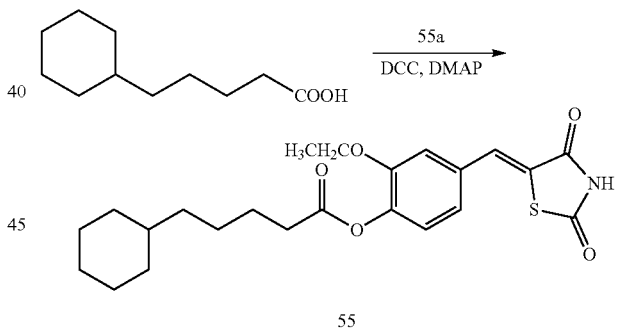

55

1 g (3.77 mmol) of 55a was added to a round-bottomed flask, and then, 0.724 g (3.77 mmol) of 5-cyclohexylpentanoic acid and 0.038 g (0.32 mmol) of DMAP (4-(dimethylamino)pyridine) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.5%

1H NMR (300 MHz, DMSO-d6) δ 12.64 (s, 1H), δ 7.79 (s, 1H), δ 7.34 (d, J=1.47 Hz, 1H), δ 7.24 (d, J=8.43 Hz, 1H), δ 7.18 (dd, J=8.43 and 1.47 Hz, 1H), δ 4.11 (m, J=6.96 Hz, 2H), δ 2.58 (t, J=6.96 Hz, 2H), δ1.69 (m, 8H), δ 1.42 (m, 2H), δ 1.32 (t, J=6.96 Hz, 3H), δ 1.21 (m, J=6.96 Hz, 5H), δ 0.89 (m, 2H)

Example 56. Preparation of Compound 56 ((Z)-4-((2,4-dioxothiazolidin-5-ylidene)methyl)-2-ethoxyphenyl benzoate)

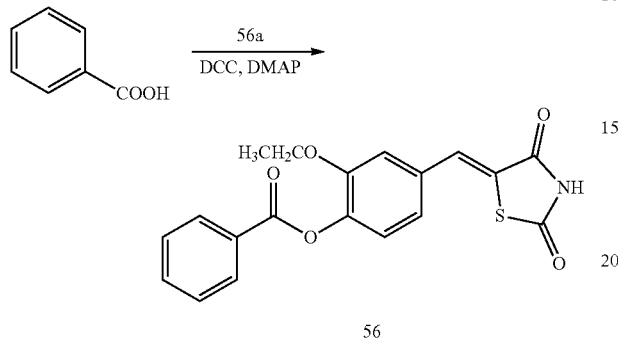

1 g (3.77 mmol) of 56a was added to a round-bottomed flask, and then 0.460 g (3.77 mmol) of benzoic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 73.6%

1H NMR (300 MHz, DMSO-d6) δ 12.66 (s, 1H), δ 8.13 (d, 2H), δ7.83 (s, 1H), δ 7.78 (t, J=7.32 Hz, 1H), δ 7.64 (t, J=7.32 Hz, 2H), δ7.43 (d, J=8.43 Hz, 1H), δ 7.40 (s, 1H), δ 7.24 (d, J=8.43 Hz, 1H), δ 4.14 (m, J=6.96 Hz, 2H), δ1.23 (t, J=6.96 Hz, 3H)

Example 57. Preparation of Compound 57 ((Z)-4-((2,4-dioxothiazolidin-5-ylidene)methyl)-2-ethoxyphenyl 2-phenylacetate)

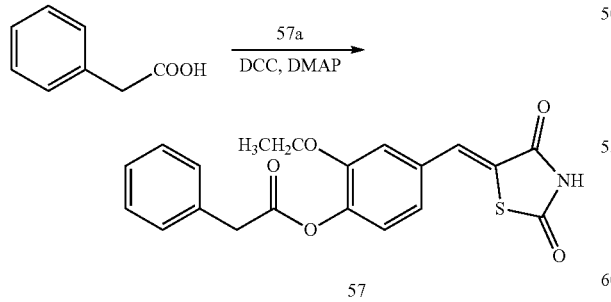

1 g (3.77 mmol) of 57a was added to a round-bottomed flask, and then, 0.513 g (3.77 mmol) of phenylacetic acid and 0.038 g (0.32 mmol) of DMAP (4-(dimethylamino)pyridine) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.7%

1H NMR (300 MHz, DMSO-d6) δ 12.65 (s, 1H), δ 7.78 (s, 1H), δ 7.39 (m, 7H), δ 7.18 (d, 1H), δ 4.07 (m, J=6.96 Hz, 2H), δ3.96 (s, 2H), δ1.25 (t, J=6.96 Hz, 3H)

Example 58. Preparation of Compound 58 ((Z)-4-((2,4-dioxothiazolidin-5-ylidene)methyl)-2-ethoxyphenyl 3-phenylpropanoate)

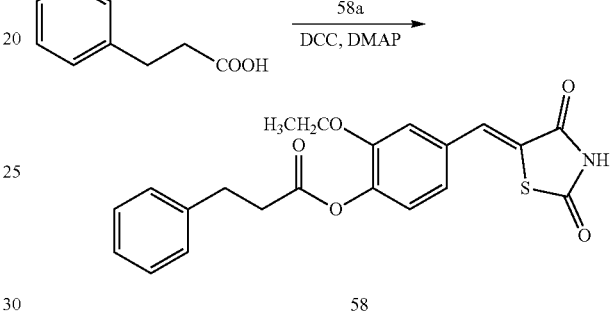

1 g (3.77 mmol) of 58a was added to a round-bottomed flask, and then, 0.566 g (3.77 mmol) of 3-phenylpropionic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.9%

1H NMR (300 MHz, DMSO-d6) δ 12.65 (s, 1H), δ 7.79 (s, 1H), δ 7.34 (m, 8H), δ 4.09 (m, J=6.96 Hz, 2H), δ 2.99 (m, 4H), δ 1.27 (t, J=6.96 Hz, 3H)

Example 59. Preparation of Compound 59 ((Z)-4-((2,4-dioxothiazolidin-5-ylidene)methyl)-2-ethoxyphenyl 4-phenylbutanoate)

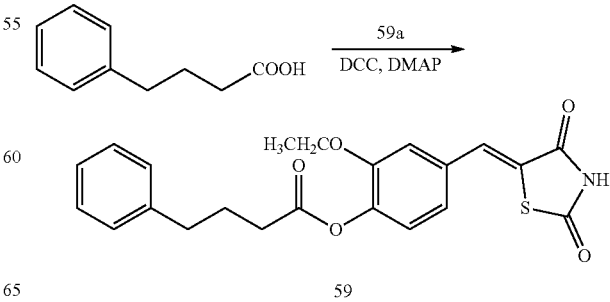

1 g (3.77 mmol) of 59a was added to a round-bottomed flask, and then, 0.619 g (3.77 mmol) of 4-phenylbutyric acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 84.4%

1H NMR (300 MHz, DMSO-d6) δ 12.65 (s, 1H), δ 7.79 (s, 1H), δ 7.35 (m, 8H), δ 4.12 (m, J=6.96 Hz, 2H), δ 2.72 (t, J=7.32 Hz, 2H), δ 2.60 (t, J=7.32 Hz, 2H), δ 1.99 (m, J=7.32 Hz, 2H), δ 1.30 (t, J=6.96 Hz, 3H)

Example 60. Preparation of Compound 60 ((Z)-4-((2,4-dioxothiazolidin-5-ylidene)methyl)-2-ethoxyphenyl 5-phenylpentanoate)

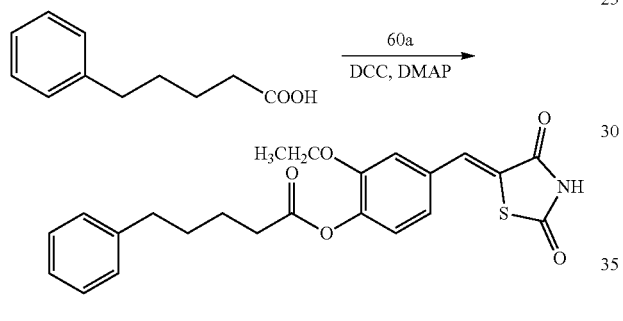

60

1 g (3.77 mmol) of 60a was added to a round-bottomed flask, and then, 0.672 g (3.77 mmol) of 5-phenylpentanoic acid and 0.038 g (0.32 mmol) of 4-(dimethylamino)pyridine (DMAP) were added thereto, and then, the result was dissolved in dichloromethane (20 ml), followed by stirring in an ice bath. After 5 minutes, 0.716 g (3.47 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.1%

1H NMR (300 MHz, DMSO-d6) δ 12.64 (s, 1H), δ 7.79 (s, 1H), δ 7.34 (m, 8H), δ 4.08 (m, J=6.96 Hz, 2H), δ 2.64 (m, J=6.96 Hz, 4H), δ 1.68 (m, J=6.96 Hz, 4H), δ 1.30 (t, J=6.96 Hz, 3H)

Example 61. Preparation of Compound 61 ((Z)-4-((2,4-dioxothiazolidin-5-ylidene)methyl)phenyl cyclopropanecarboxylate)

(1) Preparation of Reaction Intermediate

First, Compounds 61a to 75a (5-(4-hydroxy-benzylidene) thiazolidine-2,4-dione), which are reactants used for synthesizing Compounds 61 to 75, were synthesized according to the following scheme.

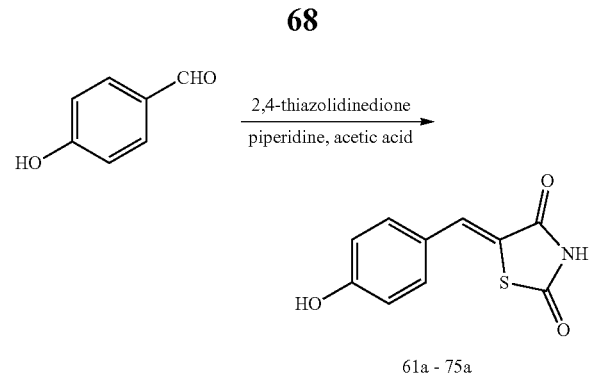

61a - 75a 1 g (8.19 mmol) of 4-hydroxy-benzaldehyde and 0.959 g (8.19 mmol) of 2,4-thiazolidinedione were placed in a round flask equipped with a Dean-Stark trap, and then dissolved in 20 ml of toluene, which is a reaction solvent, and then, 0.404 ml (4.09 mmol) of piperidine and 0.234 ml (4.09 mmol) of acetic acid were added thereto, followed by the reaction at a temperature of 80° for 18 hours or more. The completion of the reaction was confirmed by TLC, and the resulting precipitate was recrystallized and then filtered under reduced pressure to obtain a pure solid.

Yield: 95.5%

1H NMR (300 MHz, DMSO-d6) δ 12.46 (s, 1H), δ 10.32 (s, 1H), δ 7.69 (s, 1H), δ 7.46 (d, J=8.43 Hz, 2H), δ6.92 (d, J=8.43 Hz, 2H)

(2) Preparation of Compound 61 ((Z)-4-((2,4-dioxothiazolidin-5-ylidene)methyl)phenyl cyclopropanecarboxylate)

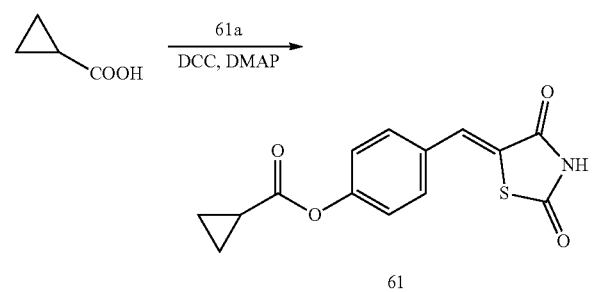

61

1 g (4.52 mmol) of 61a was added to a round-bottomed flask, and then, 0.36 g (4.52 mmol) of cyclopropanecarboxylic acid, and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 81.1%

1H NMR (300 MHz, DMSO-d6) δ 12.64 (s, 1H), δ 7.80 (s, 1H), δ 7.66 (d, J=8.43 Hz, 2H), δ 7.32 (d, J=8.43 Hz, 2H), δ1.95 (m, J=4.41 Hz, 1H), δ 1.15 (m, J=4.41 Hz, 4H)

Example 62. Preparation of Compound 62 ((Z)-4-((2,4-dioxothiazolidin-5-ylidene)methyl)phenyl cyclobutanecartboxylate)

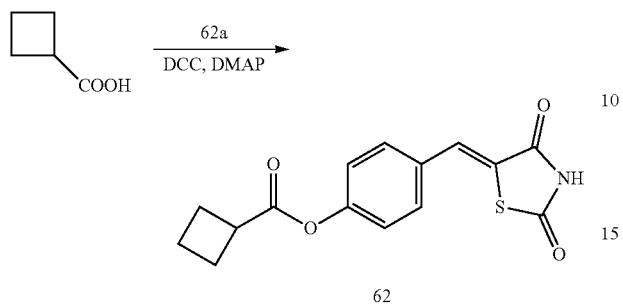

1 g (4.52 mmol) of 62a was added to a round-bottomed flask, and then, 0.432 g (4.52 mmol) of cyclobutanecarboxylic acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 83.6%

1H NMR (300 MHz, DMSO-d6) δ 12.65 (s, 1H), δ 7.80 (s, 1H), δ 7.69 (d, J=8.43 Hz, 2H), δ7.31 (d, J=8.43 Hz, 2H), δ3.52 (m, 1H), δ 2.39 (m, 4H), δ 2.07 (m, 1H), δ 1.94 (m, 1H)

Example 63. Preparation of Compound 63 ((Z)-4-((2,4-dioxothiazolidin-5-ylidene)methyl)phenyl cyclopentanecarboxylate)

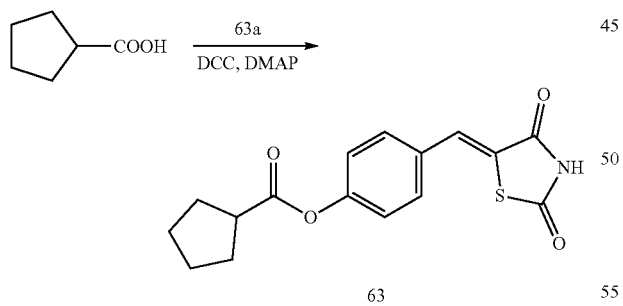

1 g (4.52 mmol) of 63a was added to a round-bottomed flask, and then, 0.491 g (4.52 mmol) of cyclopentanecarboxylic acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 91.1%

1H NMR (300 MHz, DMSO-d6) δ 12.65 (s, 1H), δ 7.81 (s, 1H), δ 7.66 (d, J=8.43 Hz, 2H), δ7.31 (d, J=8.43 Hz, 2H), δ3.11 (m, J=7.32 Hz, 1H), δ 2.00 (m, J=7.32 Hz, 4H), δ 1.67 (m, J=7.32 Hz, 4H)

Example 64. Preparation of Compound 64 ((Z)-4-((2,4-dioxothiazolidin-5-ylidene)methyl)phenyl 2-cyclopentylacetate)

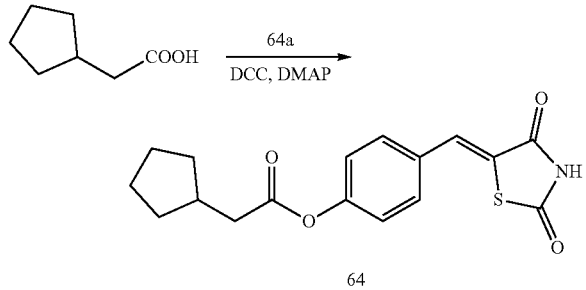

1 g (4.52 mmol) of 64a was added to a round-bottomed flask, and then, 0.568 g (4.52 mmol) of cyclopentylacetic acid and 0.568 g (4.52 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 78.9%

1H NMR (300 MHz, DMSO-d6) δ 12.64 (s, 1H), δ 7.80 (s, 1H), δ 7.70 (d, J=8.79 Hz, 2H), δ7.30 (d, J=8.79 Hz, 2H), δ 2.62 (d, J=7.32 Hz, 2H), δ 2.32 (m, J=7.32 Hz, 1H), δ 1.88 (m, J=6.96 Hz, 2H), δ 1.68 (m, J=6.96 Hz, 4H)

Example 65. Preparation of Compound 65 ((Z)-4-((2,4-dioxothiazolidin-5-ylidene)methyl)phenyl 3-cyclopentylpropanoate)

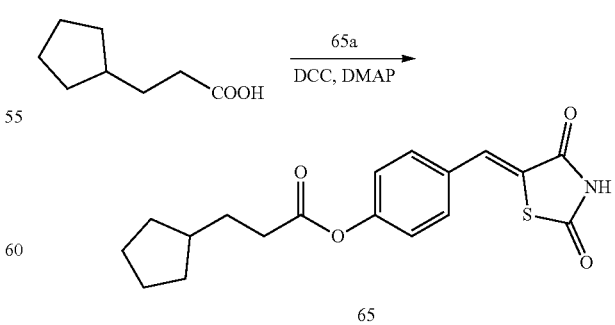

1 g (4.52 mmol) of 65a was added to a round-bottomed flask, and then, 0.645 g (4.52 mmol) of 3-cyclopentylpropionic acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 92.4%

1H NMR (300 MHz, DMSO-d6) δ 12.65 (s, 1H), δ 7.80 (s, 1H), δ 7.66 (d, J=8.4 Hz, 2H), δ7.31 (d, J=8.4 Hz, 2H), δ 2.63 (d, J=7.68 Hz, 2H), δ1.87 (m, 3H), δ 1.69 (m, 6H), δ 1.14 (m, J=7.68 Hz, 2H)

Example 66. Preparation of Compound 66 ((Z)-4-((2,4-dioxothiazolidin-5-ylidene)methyl)phenyl cyclohexanecarboxylate)

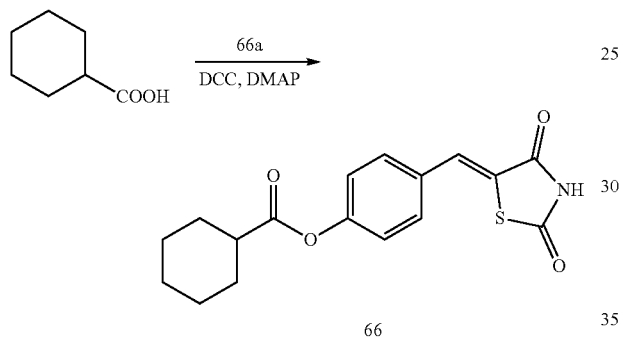

1 g (4.52 mmol) of 66a was added to a round-bottomed flask, and then, 0.579 g (4.52 mmol) of cyclohexanecarboxylic acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 86.6%

1H NMR (300 MHz, DMSO-d6) δ 12.63 (s, 1H), δ 7.80 (s, 1H), δ 7.66 (d, J=8.4 Hz, 2H), δ7.29 (d, J=8.4 Hz, 2H), δ 2.62 (m, 1H), δ 2.00 (m, 2H), δ1.73 (m, 2H), δ 1.64 (m, 3H), δ 1.36 (m, 3H)

Example 67. Preparation of Compound 67 ((Z)-4-((2,4-dioxothiazolidin-5-ylidene)methyl)phenyl 2-cyclohexylacetate)

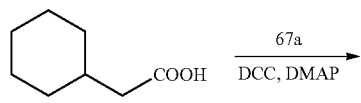

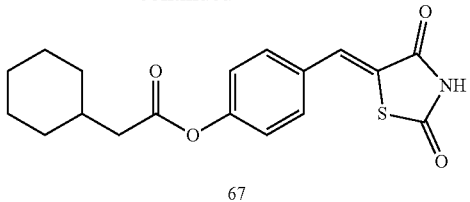

1 g (4.52 mmol) of 67a was added to a round-bottomed flask, and then, 0.643 g (4.52 mmol) of cyclohexylacetic acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 89.7%

1H NMR (300 MHz, DMSO-d6) δ 12.64 (s, 1H), δ 7.80 (s, 1H), δ 7.66 (d, J=8.79 Hz, 2H), δ 7.30 (d, J=8.79 Hz, 2H), δ 2.49 (d, 2H), δ1.87 (m, 6H), δ 1.32 (m, 5H)

Example 68. Preparation of Compound 68 ((Z)-4-((2,4-dioxothiazolidin-5-ylidene)methyl)phenyl 3-cyclohexylpropanoate)

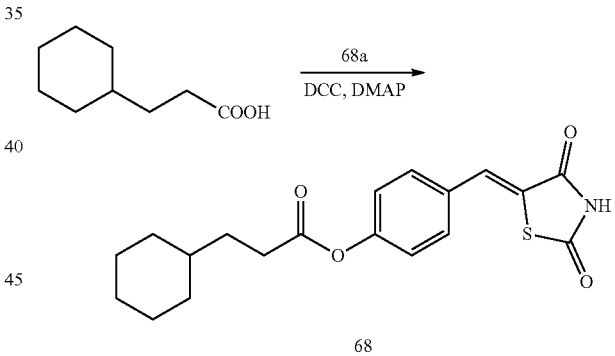

1 g (4.52 mmol) of 68a was added to a round-bottomed flask, and then, 0.706 g (4.52 mmol) of 3-cyclohexylpropionic acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 90.7%

1H NMR (300 MHz, DMSO-d6) δ 12.63 (s, 1H), δ 7.80 (s, 1H), δ 7.65 (d, J=8.79 Hz, 2H), δ7.29 (d, J=8.79 Hz, 2H), δ 2.62 (t, J=7.71 Hz, 2H), δ1.73 (m, J=7.71 Hz, 7H), δ 1.34 (m, J=7.71 Hz, 4H), δ 0.95 (m, 2H)

Example 69. Preparation of Compound 69 ((Z)-4-((2,4-dioxothiazolidin-5-ylidene)methyl)phenyl 4-cyclohexylbutanoate)

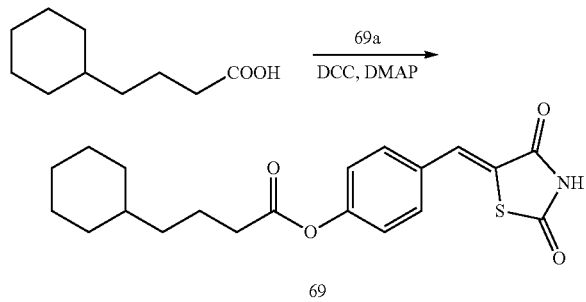

1 g (4.52 mmol) of 69a was added to a round-bottomed flask, and then, 0.77 g (4.52 mmol) of 4-cyclohexylbutyric acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N,N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 90.6%

1H NMR (300 MHz, DMSO-d6) δ 12.65 (s, 1H), δ 7.80 (s, 1H), δ 7.66 (d, J=8.4 Hz, 2H), δ7.30 (d, J=8.4 Hz, 2H), δ 2.60 (t, 2H), δ 1.71 (m, 7H), δ 1.26 (m, 6H), δ 0.92 (m, 2H)

Example 70. Preparation of Compound 70 ((Z)-4-((2,4-dioxothiazolidin-5-ylidene)methyl)phenyl 5-cyclohexylpentanoate)

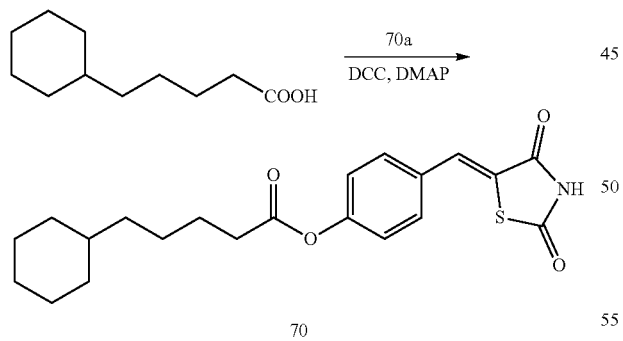

1 g (4.52 mmol) of 70a was added to a round-bottomed flask, and then, 0.868 g (4.52 mmol) of 5-cyclohexylpentanoic acid and 0.046 g (0.38 mmol) of DMAP (4-(dimethylamino)pyridine) were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 84.5%

1H NMR (300 MHz, DMSO-d6) δ 12.65 (s, 1H), δ 7.80 (s, 1H), δ 7.66 (d, J=8.43 Hz, 2H), δ7.30 (d, J=8.43 Hz, 2H), δ 2.62 (t, J=7.32 Hz, 2H), δ1.69 (m, J=7.32 Hz, 7H), δ 1.40 (m, 2H), δ1.21 (m, J=7.32 Hz, 6H), δ 0.89 (m, 2H)

Example 71. Preparation of Compound 71 ((Z)-4-((2,4-dioxothiazolidin-5-ylidene)methyl)phenyl benzoate)

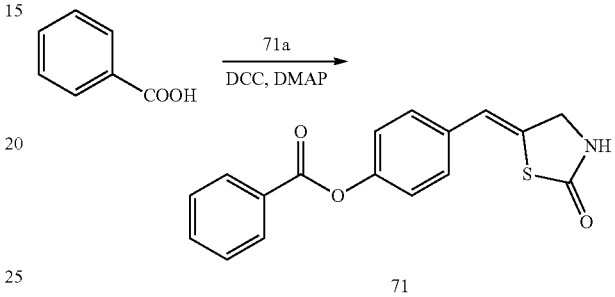

1 g (4.52 mmol) of 71a was added to a round-bottomed flask, and then, 0.552 g (4.52 mmol) of benzoic acid and 0.046 g (0.38 mmol) of DMAP were added thereto, and then, the result was dissolved in dichloromethane (20 ml), followed by stirring in an ice bath. After 5 minutes, 0.858 g (4.16 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 72.2%

1H NMR (300 MHz, DMSO-d6) δ 12.65 (s, 1H), δ 8.16 (d, J=7.32 Hz, 2H), δ 7.84 (s, 1H), δ 7.80 (m, J=7.32 Hz, 3H), δ 7.65 (t, J=7.32 Hz, 2H), δ7.50 (d, J=7.32 Hz, 2H)

Example 72. Preparation of Compound 72 ((Z)-4-((2,4-dioxothiazolidin-5-ylidene)methyl)phenyl 2-phenylacetate)

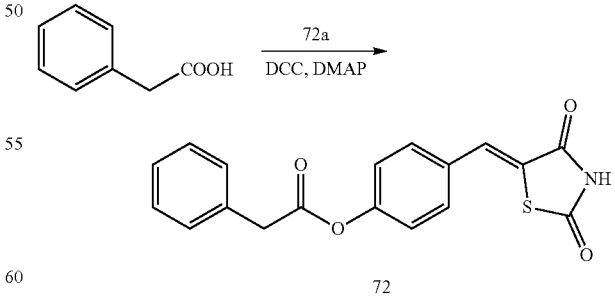

1 g (4.52 mmol) of 72a was added to a round-bottomed flask, and then, 0.615 g (4.52 mmol) of phenylacetic acid and 0.046 g (0.38 mmol) of DMAP were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 88.8%

1H NMR (300 MHz, DMSO-d6) δ 12.65 (s, 1H), δ 7.80 (s, 1H), δ 7.68 (d, 2H), δ 7.40 (m, 7H), δ 4.00 (s, 2H)

Example 73. Preparation of Compound 73 ((Z)-4-((2,4-dioxothiazolidin-5-ylidene)methyl)phenyl 3-phenylpropanoate)

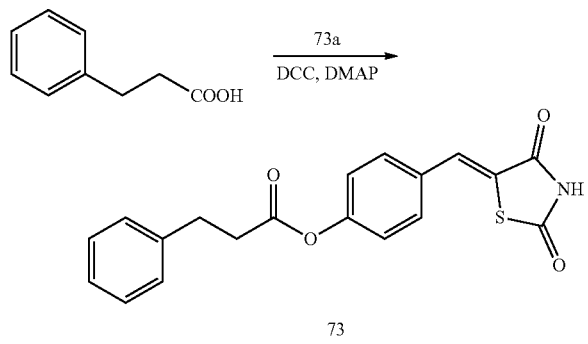

1 g (4.52 mmol) of 73a was added to a round-bottomed flask, and then, 0.679 g (4.52 mmol) of 3-phenylpropionic acid and 0.046 g (0.38 mmol) of DMAP were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 83.5%

1H NMR (300 MHz, DMSO-d6) δ 12.65 (s, 1H), δ 7.79 (s, 1H), δ 7.65 (d, J=8.43 Hz, 2H), δ7.35 (m, J=8.43 Hz, 4H), δ 7.26 (m, J=8.43 Hz, 3H), δ 2.99 (m, 4H)

Example 74. Preparation of Compound 74 ((Z)-4-((2,4-dioxothiazolidin-5-ylidene)methyl)phenyl 4-phenylbutanoate)

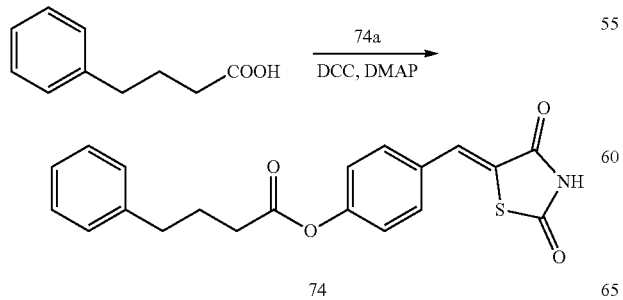

1 g (4.52 mmol) of 74a was added to a round-bottomed flask, and then, 0.742 g (4.52 mmol) of 4-phenylbutyric acid and 0.046 g (0.38 mmol) of DMAP were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 80.1%

1H NMR (300 MHz, DMSO-d6) δ 12.65 (s, 1H), δ 7.80 (s, 1H), δ 7.66 (d, 2H), δ 7.33 (m, 7H), δ 2.63 (t, 4H), δ 1.96 (m, 2H)

Example 75. Preparation of Compound 75 ((Z)-4-((2,4-dioxothiazolidin-5-ylidene)methyl)phenyl 5-phenylpentanoate)

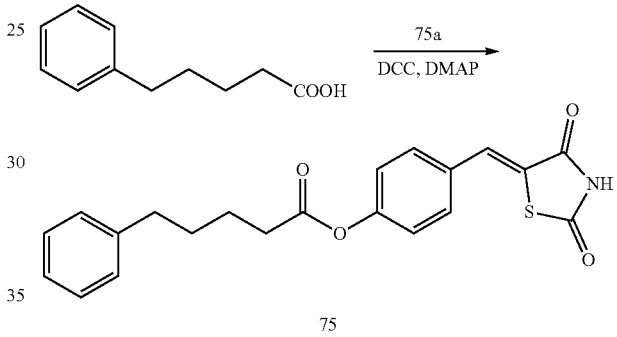

1 g (4.52 mmol) of 75a was added to a round-bottomed flask, and then, 0.806 g (4.52 mmol) of 5-phenylpentanoic acid and 0.046 g (0.38 mmol) of DMAP were added thereto, and then, the result was dissolved in dichloromethane (20 ml), followed by stirring in an ice bath. After 5 minutes, 0.858 g (4.16 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 77.8%

1H NMR (300 MHz, DMSO-d6) δ 12.62 (s, 1H), δ 7.80 (s, 1H), δ 7.66 (d, J=8.43 Hz, 2H), δ 7.30 (m, J=8.43 Hz, 7H), δ 2.63 (t, 4H), δ 1.68 (m, 4H)

Example 76. Preparation of Compound 76 ((Z)-2-chloro-3-((2,4-dioxothiazolidin-5-ylidene)methyl) phenyl cyclopropanecarboxylate)

(1) Preparation of Reaction Intermediate

First, Compounds 76a to 90a (5-(2-chloro-3-hydroxybenzylidene)-thiazolidine-2,4-dione), which are reactants used for synthesizing Compounds 76 to 90, were synthesized according to the following scheme.

77

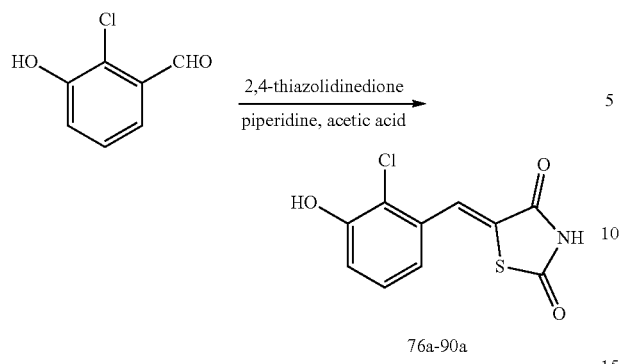

76a-90a 1 g (6.39 mmol) of 2-chloro-3-hydroxybenzaldehyde and 0.748 g (6.39 mmol) of 2,4-thiazolidinedione were placed in a round flask equipped with a Dean-Stark trap, and then dissolved in 20 ml of toluene, which is a reaction solvent, and then, 0.315 ml (3.19 mmol) of piperidine and 0.183 ml (3.19 mmol) of acetic acid were added thereto, followed by the reaction at a temperature of 80'C for 18 hours or more. The completion of the reaction was confirmed by TLC, and the resulting precipitate was recrystallized and then filtered under reduced pressure to obtain a pure solid.

Yield: 71.1%

1H NMR (300 MHz, DMSO-d6) δ 12.71 (s, 1H), δ 10.60 (s, 1H), δ 7.93 (s, 1H), δ 7.33 (t, J=8.04 Hz, 1H), δ 7.09 (d, J=8.04 Hz, 1H), δ 7.02 (d, J=8.04 Hz, 1H)

(2) Preparation of Compound 76 ((Z)-2-chloro-3-((2,4-dioxothiazolidin-5-ylidene)methyl)phenyl cyclopropanecarboxylate)

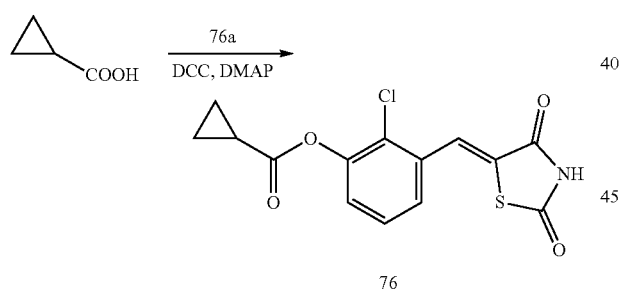

76

1 g (3.91 mmol) of 76a was added to a round-bottomed flask, and then, 0.311 g (3.91 mmol) of cyclopropanecarboxylic acid, and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 71.3%

1H NMR (300 MHz, DMSO-d6) δ 12.80 (s, 1H), δ 7.88 (s, 1H), δ 7.58 (t, J=8.07 Hz, 1H), δ 7.49 (dd, J=8.07 and 1.47 Hz, 1H), δ 7.44 (dd, J=8.07 and 1.47 Hz, 1H), δ 2.02 (m, 1H), δ 1.16 (m, 4H)

Example 77. Preparation of Compound 77 ((Z)-2-chloro-3-((2,4-dioxothiazolidin-5-ylidene)methyl)phenyl cyclobutanecarboxylate)

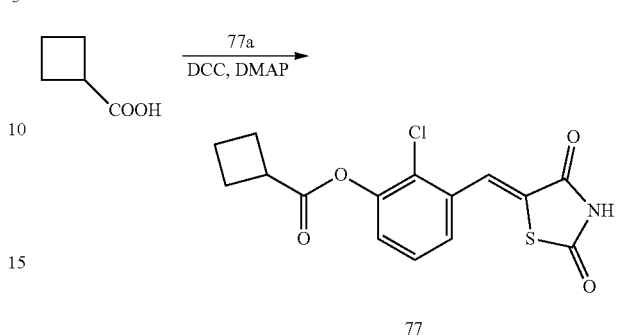

77

1 g (3.91 mmol) of 77a was added to a round-bottomed flask, and then, 0.374 g (3.91 mmol) of cyclobutanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 73.3%

1H NMR (300 MHz, DMSO-d6) δ 12.79 (s, 1H), δ 7.89 (s, 1H), δ 7.60 (t, J=8.07 Hz, 1H), δ 7.50 (dd, J=8.07 and 1.47 Hz, 1H), δ 7.46 (dd, J=8.07 and 1.47 Hz, 1H), δ 3.59 (m, 1H), δ 2.40 (m, 4H), δ 2.10 (m, 2H)

Example 78. Preparation of Compound 78 ((Z)-2-chloro-3-((2,4-dioxothiazolidin-5-ylidene)methyl) phenyl cyclopentanecarboxylate)

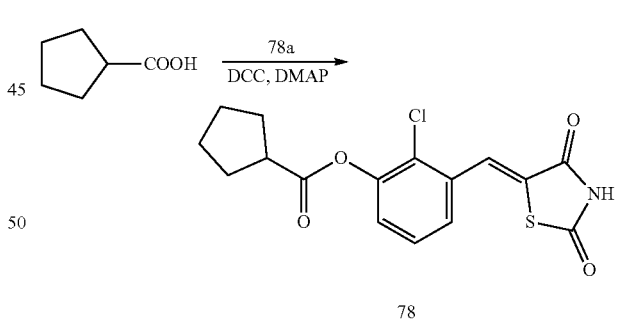

78

1 g (3.91 mmol) of 78a was added to a round-bottomed flask, and then, 0.425 g (3.91 mmol) of cyclopentanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 69.9%

1H NMR (300 MHz, DMSO-d6) δ 12.80 (s, 1H), δ 7.89 (s, 1H), δ 7.59 (t, J=7.68 Hz, 1H), δ 7.50 (dd, J=7.68 and 1.47 Hz, 1H), δ 7.45 (dd, J=7.68 and 1.47 Hz, 1H), δ 3.18 (m, 1H), δ 2.01 (m, 4H), δ 1.71 (m, 4H)

Example 79. Preparation of Compound 79 ((Z)-2-chloro-3-((2,4-dioxothiazolidin-5-ylidene)methyl)phenyl 2-cyclopentylacetate)

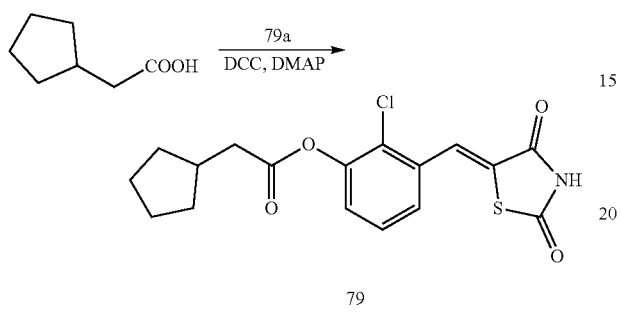

79

1 g (3.91 mmol) of 79a was added to a round-bottomed flask, and then, 0.491 g (3.91 mmol) of cyclopentylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 75.6%

1H NMR (300 MHz, DMSO-d6) δ 12.81 (s, 1H), δ 7.89 (s, 1H), δ 7.60 (t, J=8.07 Hz, 1H), δ 7.50 (dd, J=8.07 and 1.47 Hz, 1H), δ 7.44 (dd, J=8.07 and 1.47 Hz, 1H), δ 2.68 (d, J=7.32 Hz, 2H), δ 2.36 (m, J=7.32 Hz, 1H), δ 1.90 (m, 2H), δ1.68 (m, 4H), δ 1.30 (m, 2H)

Example 80. Preparation of Compound 80 ((Z)-2-chloro-3-((2,4-dioxothiazolidin-5-ylidene)methyl)phenyl 3-cyclopentylpropanoate)

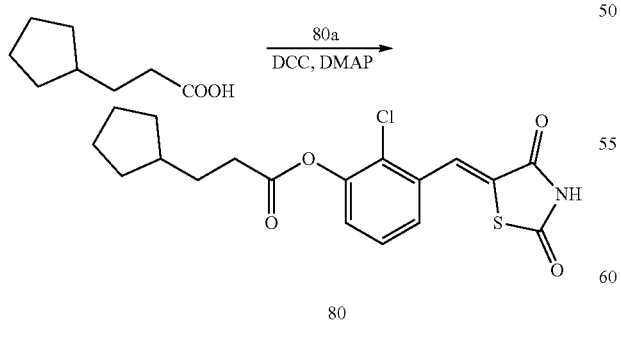

80

1 g (3.91 mmol) of 80a was added to a round-bottomed flask, and then, 0.558 g (3.91 mmol) of 3-cyclopentylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 76.6%

1H NMR (300 MHz, DMSO-d6) δ 12.80 (s, 1H), δ 7.89 (s, 1H), δ 7.60 (t, J=8.04 Hz, 1H), δ 7.50 (dd, J=8.04 and 1.83 Hz, 1H), δ 7.45 (dd, J=8.04 and 1.83 Hz, 1H), δ 2.69 (t, 2H), δ 1.85 (m, 5H), δ 1.59 (m, 4H), δ 1.15 (m, 2H)

Example 81. Preparation of Compound 81 ((Z)-2-chloro-3-((2,4-dioxothiazolidin-5-ylidene)methyl)phenyl cyclohexanecarboxylate)

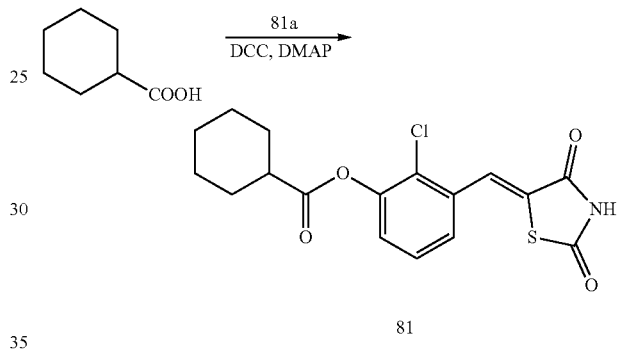

81

1 g (3.91 mmol) of 81a was added to a round-bottomed flask, and then, 0.501 g (3.91 mmol) of cyclohexanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 71.1%

1H NMR (300 MHz, DMSO-d6) δ 12.82 (s, 1H), δ 7.88 (s, 1H), δ 7.59 (t, J=7.68 Hz, 1H), δ 7.50 (dd, J=7.68 and 1.47 Hz, 1H), δ 7.44 (dd, J=7.68 and 1.47 Hz, 1H), δ 2.75 (m, 1H), δ 2.08 (m, 2H), δ1.76 (m, 2H), δ1.64 (m, 6H)

Example 82. Preparation of Compound 82 ((Z)-2-chloro-3-((2,4-dioxothiazolidin-5-ylidene)methyl)phenyl 2-cyclohexylacetate)

-continued

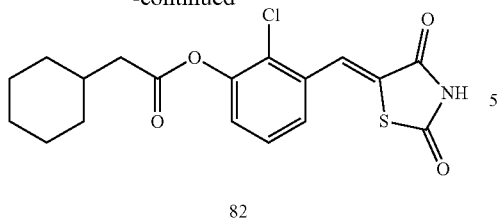

82

1 g (3.91 mmol) of 82a was added to a round-bottomed flask, and then, 0.556 g (3.91 mmol) of cyclohexylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 68.4%

1H NMR (300 MHz, DMSO-d6) δ 12.79 (s, 1H), δ 7.89 (s, 1H), δ 7.59 (t, J=7.68 Hz, 1H), δ 7.50 (dd, J=7.68 and 1.47 Hz, 1H), δ 7.43 (dd, J=7.68 and 1.47 Hz, 1H), δ 2.55 (d, 2H), δ 1.89 (m, 6H), δ 1.32 (m, 5H)

Example 83. Preparation of Compound 83 ((Z)-2-chloro-3-((2,4-dioxothiazolidin-5-ylidene)methyl) phenyl 3-cyclohexylpropanoate)

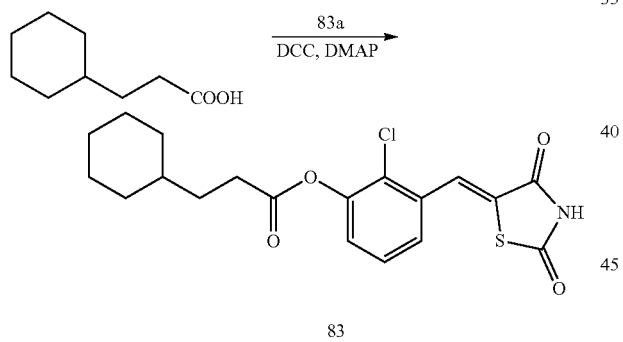

83

1 g (3.91 mmol) of 83a was added to a round-bottomed flask, and then, 0.611 g (3.91 mmol) of 3-cyclohexylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 79.9%

1H NMR (300 MHz, DMSO-d6) δ 12.79 (s, 1H), δ 7.89 (s, 1H), δ 7.59 (t, J=7.68 Hz, 1H), δ 7.50 (dd, J=7.68 and 1.83 Hz, 1H), δ 7.44 (dd, J=7.68 and 1.83 Hz, 1H), δ 2.69 (t, 2H), δ1.75 (m, 7H), δ 1.38 (m, 6H)

Example 84. Preparation of Compound 84 ((Z)-2-chloro-3-((2,4-dioxothiazolidin-5-ylidene)methyl) phenyl 4-cyclohexylbutanoate))

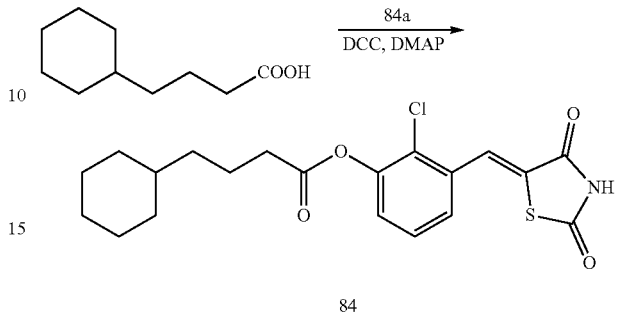

84

1 g (3.91 mmol) of 84a was added to a round-bottomed flask, and then, 0.666 g (3.91 mmol) of 4-cyclohexylbutyric acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 71.1%

1H NMR (300 MHz, DMSO-d6) δ 12.79 (s, 1H), δ 7.89 (s, 1H), δ 7.60 (t, J=8.04 Hz, 1H), δ 7.50 (dd, J=8.04 and 1.47 Hz, 1H), δ 7.44 (dd, J=8.04 and 1.47 Hz, 1H), δ 2.66 (t, 2H), δ1.71 (m, 7H), δ 1.31 (m, 6H), δ 0.92 (m, 2H)

Example 85. Preparation of Compound 85 ((Z)-2-chloro-3-((2,4-dioxothiazolidin-5-ylidene)methyl) phenyl 5-cyclohexylpentanoate)

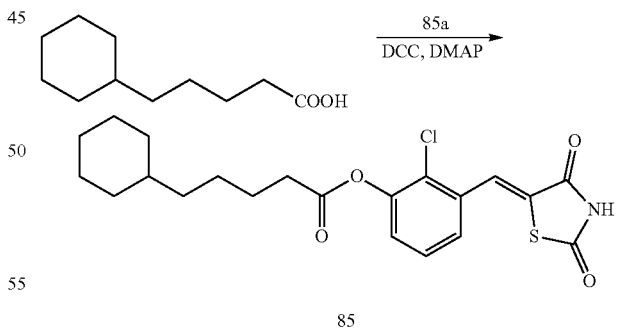

85

1 g (3.91 mmol) of 85a was added to a round-bottomed flask, and then, 0.751 g (3.91 mmol) of 5-cyclohexylpentanoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 69.2%

1H NMR (300 MHz, DMSO-d6) δ 12.80 (s, 1H), δ 7.89 (s, 1H), δ 7.60 (t, J=8.07 Hz, 1H), δ 7.51 (dd, J=8.07 and 1.47 Hz, 1H), δ 7.45 (dd, J=8.07 and 1.47 Hz, 1H), δ 2.68 (t, 2H), δ1.69 (m, 7H), δ 1.43 (m, 2H), δ1.22 (m, 6H), δ 0.90 (m, 2H)

Example 86. Preparation of Compound 86 ((Z)-2-chloro-3-((2,4-dioxothiazolidin-5-ylidene)methyl) phenyl benzoate)

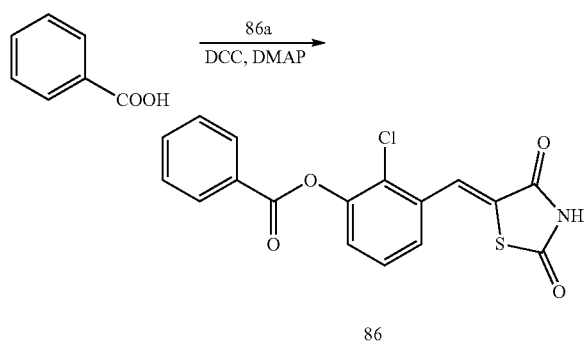

86

1 g (3.91 mmol) of 86a was added to a round-bottomed flask, and then, 0.478 g (3.91 mmol) of benzoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 66.6%

1H NMR (300 MHz, DMSO-d6) δ 12.83 (s, 1H), δ 8.19 (d, 2H), δ 7.92 (s, 1H), δ 7.83 (t, 1H), δ 7.67 (m, 4H), δ 7.59 (m, 1H), δ 1.69 (m, 7H), δ 1.43 (m, 2H), δ1.22 (m, 6H), δ 0.90 (m, 2H)

Example 87. Preparation of Compound 87 ((Z)-2-chloro-3-((2,4-dioxothiazolidin-5-ylidene)methyl) phenyl 2-phenylacetate)

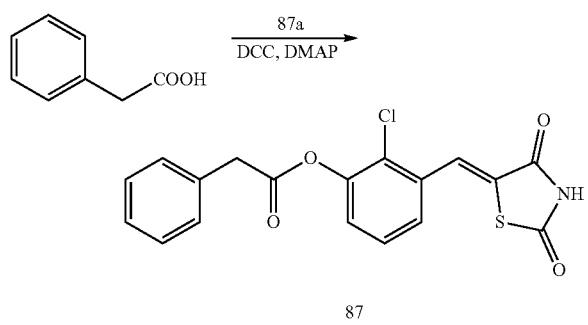

87

1 g (3.91 mmol) of 87a was added to a round-bottomed flask, and then, 0.533 g (3.91 mmol) of phenylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 77.8%

1H NMR (300 MHz, DMSO-d6) δ 12.81 (s, 1H), δ 7.87 (s, 1H), δ 7.60 (t, J=8.04 Hz, 1H), δ 7.51 (dd, J=8.04 and 1.47 Hz, 1H), δ 7.47 (dd, J=8.04 and 1.47 Hz, 1H), δ 7.42 (m, 5H), δ 4.07 (s, 2H)

Example 88. Preparation of Compound 88 ((Z)-2-chloro-3-((2,4-dioxothiazolidin-5-ylidene)methyl) phenyl 3-phenylpropanoate)

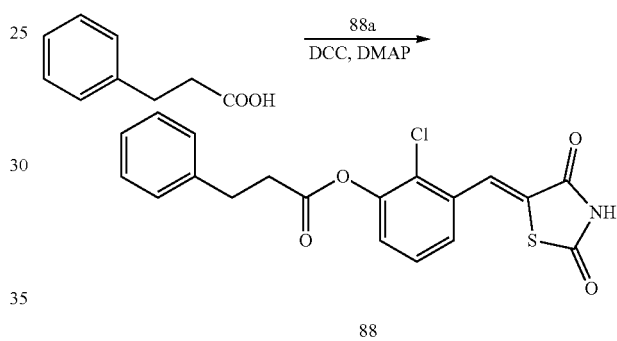

88

1 g (3.91 mmol) of 88a was added to a round-bottomed flask, and then, 0.587 g (3.91 mmol) of 3-phenylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 71.1%

1H NMR (300 MHz, DMSO-d6) δ 12.86 (s, 1H), δ 7.86 (s, 1H), δ 7.59 (t, J=8.04 Hz, 1H), δ 7.50 (dd, J=8.04 and 1.47 Hz, 1H), δ 7.36 (dd, J=8.04 and 1.47 Hz, 1H), δ 7.32 (m, 5H), δ 3.01 (t, 4H)

Example 89. Preparation of Compound 89 ((Z)-2-chloro-3-((2,4-dioxothiazolidin-5-ylidene)methyl) phenyl 4-phenylbutanoate)

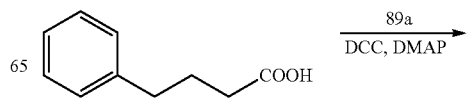

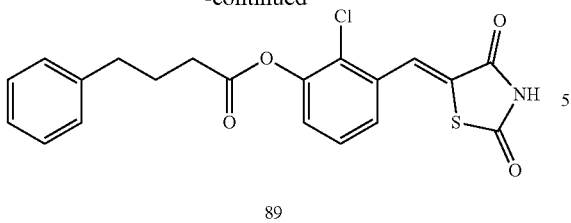

89

1 g (3.91 mmol) of 89a was added to a round-bottomed flask, and then, 0.642 g (3.91 mmol) of 4-phenylbutyric acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 80.7%

1H NMR (300 MHz, DMSO-d6) δ 12.82 (s, 1H), δ 7.89 (s, 1H), δ 7.60 (t, J=7.68 Hz, 1H), δ 7.51 (dd, J=7.68 and 1.44 Hz, 1H), δ 7.46 (dd, J=7.68 and 1.44 Hz, 1H), δ 7.34 (m, 5H), δ 2.72 (m, J=7.32 Hz, 4H), δ 2.02 (m, J=7.32 Hz, 2H)

Example 90. Preparation of Compound 90 ((Z)-2-chloro-3-((2,4-dioxothiazolidin-5-ylidene)methyl)phenyl 5-phenylpentanoate)

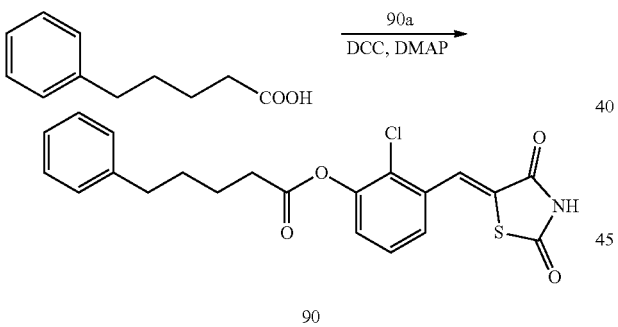

90

1 g (3.91 mmol) of 90a was added to a round-bottomed flask, and then, 0.697 g (3.91 mmol) of 5-phenylpentanoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 80.4%

1H NMR (300 MHz, DMSO-d6) δ 12.82 (s, 1H), δ 7.88 (s, 1H), δ 7.59 (t, J=7.68 Hz, 1H), δ 7.50 (dd, J=8.04 and 1.47 Hz, 1H), δ 7.44 (dd, J=8.04 and 1.47 Hz, 1H), δ 7.30 (m, 5H), δ 2.70 (m, 4H), δ 1.69 (m, 4H)

Example 91. Preparation of Compound 91 ((Z)-3-chloro-4-((2,4-dioxothiazolidin-5-ylidene)methyl)phenyl cyclopropanecarboxylate)

(1) Preparation of Reaction Intermediate

First, Compounds 91a to 105a (5-(2-chloro-4-hydroxybenzylidene)thiazolidine-2,4-dione), which are reactants used for synthesizing Compounds 91 to 105, were synthesized according to the following scheme.

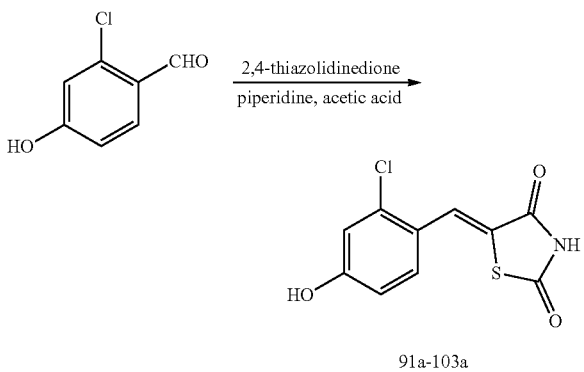

91a-103a 1 g (6.38 mmol) of 2-chloro-4-hydroxybenzaldehyde and 0.748 g (6.38 mmol) of 2,4-thiazolidinedione were placed in a round flask equipped with a Dean-Stark trap, and then dissolved in 20 ml of toluene, which is a reaction solvent, and then, 0.315 ml (3.19 mmol) of piperidine and 0.183 ml (3.19 mmol) of acetic acid were added thereto, followed by the reaction at a temperature of 80° C. for 18 hours or more. The completion of the reaction was confirmed by TLC, and the resulting precipitate was recrystallized and then filtered under reduced pressure to obtain a pure solid.

Yield: 95%

1H NMR (300 MHz, DMSO-d6) δ12.63 (s, 1H), δ10.76 (s, 1H), δ7.88 (s, 1H), δ7.44 (d, J=8.79 Hz, 1H), δ7.01 (d, J=2.58 Hz, 1H), δ6.95 (dd, J=8.79 and 2.58 Hz, 1H)

Preparation of (2) Compound 91 ((Z)-3-chloro-4-((2,4-dioxothiazolidin-5-ylidene)methyl)phenyl cyclopropanecarboxylate)

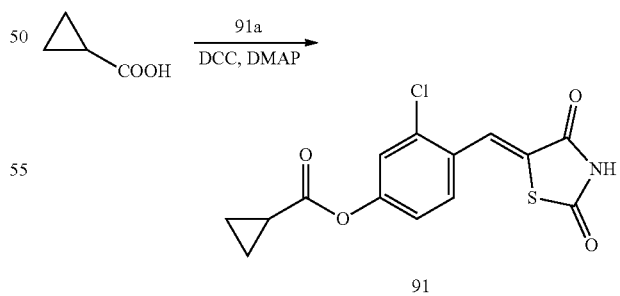

91

1 g (3.91 mmol) of 91a was added to a round-bottomed flask, and then, 0.311 g (3.91 mmol) of cyclopropanecarboxylic acid, and 0.04 g (0.33 mmol) of DMAP (4-(dimethylamino)pyridine) were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 92.1%

1H NMR (300 MHz, DMSO-d6) δ12.77 (s, 1H), δ7.88 (s, 1H), δ7.63 (d, J=8.79 Hz, 1H), δ7.59 (d, J=2.58 Hz, 1H), δ7.36 (dd, J=8.79 and 2.58 Hz, 1H), δ1.94 (m, 1H), δ1.11 (m, 4H)

Example 92. Preparation of Compound 92 ((Z)-3-chloro-4-((2,4-dioxothiazolidin-5-ylidene)methyl)phenyl cyclobutanecarboxylate)

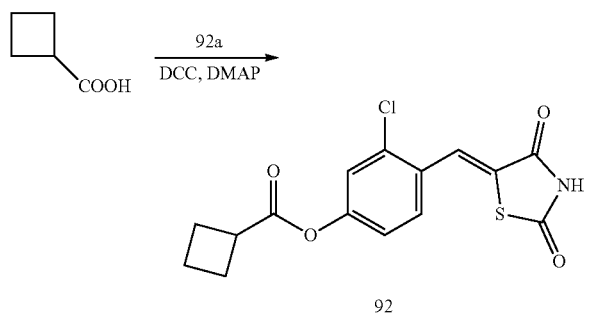

92

1 g (3.91 mmol) of 92a was added to a round-bottomed flask, and then, 0.374 g (3.91 mmol) of cyclobutanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.1%

1H NMR (300 MHz, DMSO-d6) δ12.78 (s, 1H), δ7.88 (s, 1H), δ7.62 (d, J=8.79 Hz, 1H), δ7.58 (d, J=2.19 Hz, 1H), δ7.35 (dd, J=8.79 and 2.19 Hz, 1H), δ3.52 (m, 1H), δ2.37 (m, 4H), δ2.05 (m, 2H)

Example 93. Preparation of Compound 93 ((Z)-3-chloro-4-((2,4-dioxothiazolidin-5-ylidene)methyl)phenyl cyclopentanecarboxylate)

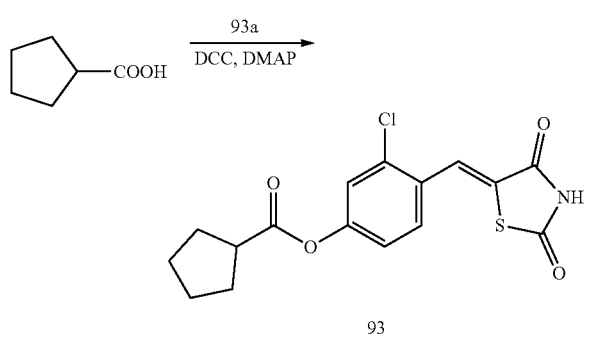

93

1 g (3.91 mmol) of 93a was added to a round-bottomed flask, and then, 0.425 g (3.91 mmol) of cyclopentanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 92.3%

1H NMR (300 MHz, DMSO-d6) δ12.77 (s, 1H), δ7.88 (s, 1H), δ7.62 (d, J=8.79 Hz, 1H), δ7.57 (d, J=2.19 Hz, 1H), δ7.34 (dd, J=8.79 and 2.19 Hz, 1H), δ3.08 (m, 1H), δ1.95 (m, 4H), δ1.66 (m, 4H)

Example 94. Preparation of Compound 94 ((Z)-3-chloro-4-((2,4-dioxothiazolidin-5-ylidene)methyl)phenyl 2-cyclopentylacetate)

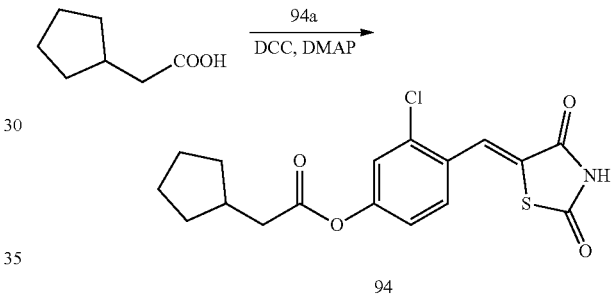

94

1 g (3.91 mmol) of 94a was added to a round-bottomed flask, and then, 0.491 g (3.91 mmol) of cyclopentylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 88.7%

1H NMR (300 MHz, DMSO-d6) δ12.78 (s, 1H), δ7.88 (s, 1H), δ7.63 (d, J=8.4 Hz, 1H), δ7.54 (d, J=2.19 Hz, 1H), δ7.34 (dd, J=8.4 and 2.19 Hz, 1H), δ2.62 (m, J=7.68 Hz, 2H), δ2.29 (m, J=7.68 Hz, 1H), δ1.88 (m, 2H), δ1.62 (m, 4H), δ1.28 (m, 2H)

Example 95. Preparation of Compound 95 ((Z)-3-chloro-4-((2,4-dioxothiazolidin-5-ylidene)methyl)phenyl 3-cyclopentylpropanoate)

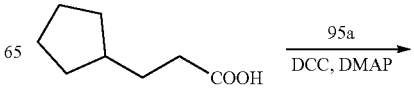

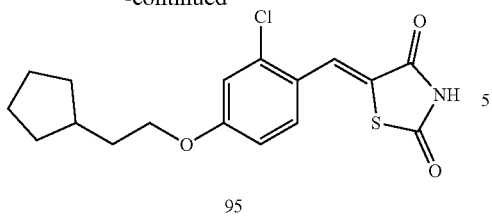

95

1 g (3.91 mmol) of 95a was added to a round-bottomed flask, and then, 0.558 g (3.91 mmol) of 3-cyclopentylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 93.3%

1H NMR (300 MHz, DMSO-d6) δ12.78 (s, 1H), δ7.88 (s, 1H), δ7.63 (d, J=8.43 Hz, 1H), δ7.56 (d, J=2.19 Hz, 1H), δ7.34 (dd, J=8.43 and 2.19 Hz, 1H), δ2.61 (t, 2H), δ1.80 (m, 10 OH), δ1.14 (m, 1H)

Example 96. Preparation of Compound 96 ((Z)-3-chloro-4-((2,4-dioxothiazolidin-5-ylidene)methyl) phenyl cyclohexanecarboxylate)

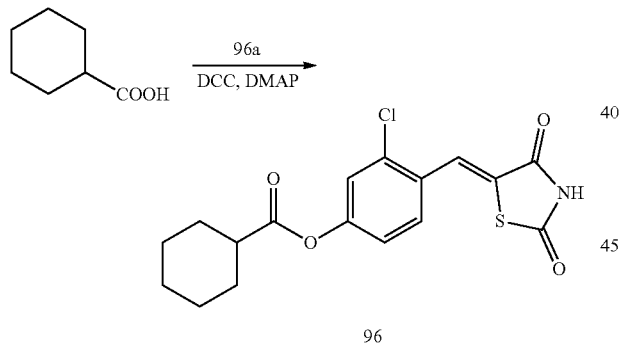

96

1 g (3.91 mmol) of 96a was added to a round-bottomed flask, and then, 0.501 g (3.91 mmol) of cyclohexanecarboxylic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 91.1%

1H NMR (300 MHz, DMSO-d6) δ12.77 (s, 1H), δ7.88 (s, 1H), δ7.63 (d, J=8.43 Hz, 1H), δ7.55 (d, J=2.22 Hz, 1H), δ7.33 (dd, J=8.43 and 2.22 Hz, 1H), δ2.62 (m, 1H), δ1.75 (m, 10H)

Example 97. Preparation of Compound 97 ((Z)-3-chloro-4-((2,4-dioxothiazolidin-5-ylidene)methyl) phenyl 2-cyclohexylacetate)

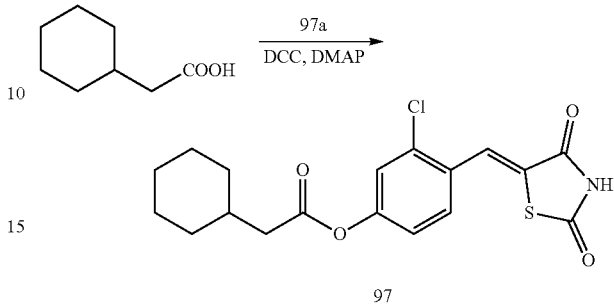

97

1 g (3.91 mmol) of 97a was added to a round-bottomed flask, and then, 0.556 g (3.91 mmol) of cyclohexylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 87.7%

1H NMR (300 MHz, DMSO-d6) δ12.78 (s, 1H), δ7.89 (s, 1H), δ7.63 (d, J=8.43 Hz, 1H), δ7.56 (d, J=2.19 Hz, 1H), δ7.33 (dd, J=8.43 and 2.19 Hz, 1H), δ1.86 (m, 7H), δ1.32 (m, 6H)

Example 98. Preparation of Compound 98 ((Z)-3-chloro-4-((2,4-dioxothiazolidin-5-ylidene)methyl) phenyl 3-cyclohexylpropanoate)

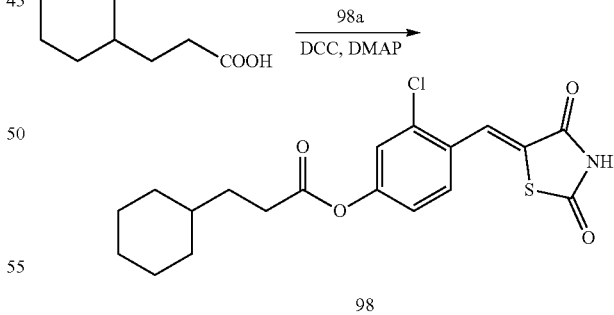

98

1 g (3.91 mmol) of 98a was added to a round-bottomed flask, and then, 0.611 g (3.91 mmol) of 3-cyclohexylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 90.8%

1H NMR (300 MHz, DMSO-d6) δ12.77 (s, 1H), δ7.88 (s, 1H), δ7.63 (d, J=8.4 Hz, 1H), δ7.55 (d, J=2.19 Hz, 1H), δ7.34 (dd, J=8.4 and 2.19 Hz, 1H), δ2.60 (t, 2H), δ1.73 (m, 8H), δ1.32 (m, 4H), δ0.95 (m, 1H)

Example 99. Preparation of Compound 99 ((Z)-3-chloro-4-((2,4-dioxothiazolidin-5-ylidene)methyl)phenyl 4-cyclohexylbutanoate)

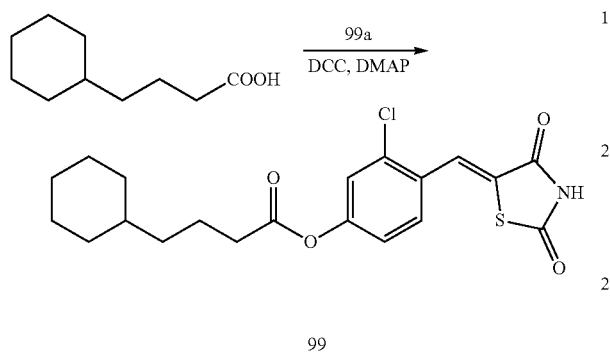

99

1 g (3.91 mmol) of 99a was added to a round-bottomed flask, and then, 0.666 g (3.91 mmol) of 4-cyclohexylbutyric acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 91.1%

1H NMR (300 MHz, DMSO-d6) δ12.78 (s, 1H), δ7.88 (s, 1H), δ7.63 (d, J=8.79 Hz, 1H), δ7.55 (d, J=2.19 Hz, 1H), δ7.34 (dd, J=8.79 and 2.19 Hz, 1H), δ2.60 (t, 2H), δ1.71 (m, 8H), δ1.26 (m, 6H), δ0.92 (m, 1H)

Example 100. Preparation of Compound 100 ((Z)-3-chloro-4-((2,4-dioxothiazolidin-5-ylidene)methyl)phenyl 5-cyclohexylpentanoate)

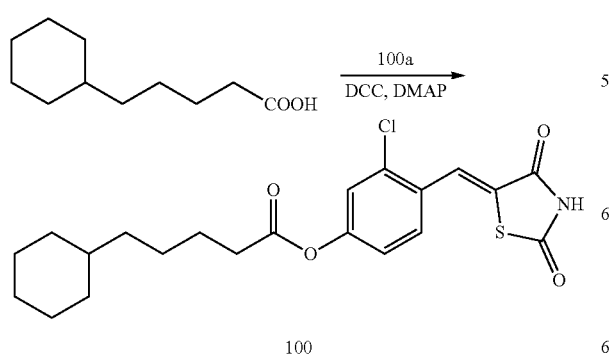

100

1 g (3.91 mmol) of 100a was added to a round-bottomed flask, and then, 0.751 g (3.91 mmol) of 5-cyclohexylpentanoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 90.7%

1H NMR (300 MHz, DMSO-d6) δ12.77 (s, 1H), δ7.88 (s, 1H), δ7.63 (d, J=8.43 Hz, 1H), δ7.54 (d, J=2.19 Hz, 1H), δ7.33 (dd, J=8.43 and 2.19 Hz, 1H), δ2.62 (t, 2H), δ1.69 (m, 8H), δ1.40 (m, 8H), δ0.90 (m, 1H)

Example 101. Preparation of Compound 101 ((Z)-3-chloro-4-((2,4-dioxothiazolidin-5-ylidene)methyl)phenyl benzoate)

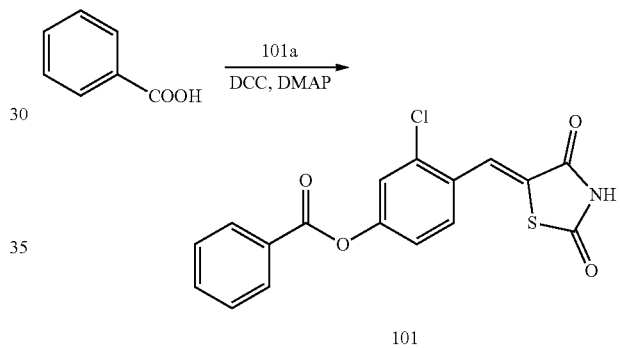

101

1 g (3.91 mmol) of 101a was added to a round-bottomed flask, and then, 0.478 g (3.91 mmol) of benzoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid·base extraction and recrystallization, thereby obtaining pure solid.

Yield: 87.1%

1H NMR (300 MHz, DMSO-d6) δ12.79 (s, 1H), δ8.15 (d, 2H), δ7.92 (s, 1H), δ7.80 (m, 6H)

Example 102. Preparation of Compound 102 ((Z)-3-chloro-4-((2,4-dioxothiazolidin-5-ylidene)methyl)phenyl 2-phenylacetate)

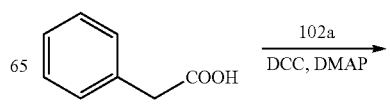

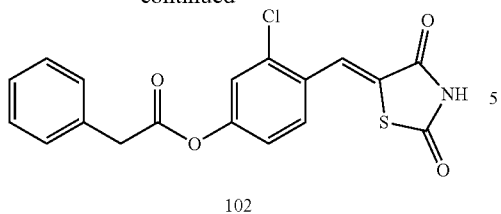

102

1 g (3.91 mmol) of 102a was added to a round-bottomed flask, and then, 0.533 g (3.91 mmol) of phenylacetic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 88.9%

1H NMR (300 MHz, DMSO-d6) δ12.77 (s, 1H), δ7.88 (s, 1H), δ7.63 (d, J=8.79 Hz, 1H), δ7.57 (d, J=2.19 Hz, 1H), δ7.40 (m, 6H), δ4.00 (s, 2H)

Example 103. Preparation of Compound 103 ((Z)-3-chloro-4-((2,4-dioxothiazolidin-5-ylidene)methyl)phenyl 3-phenylpropanoate)

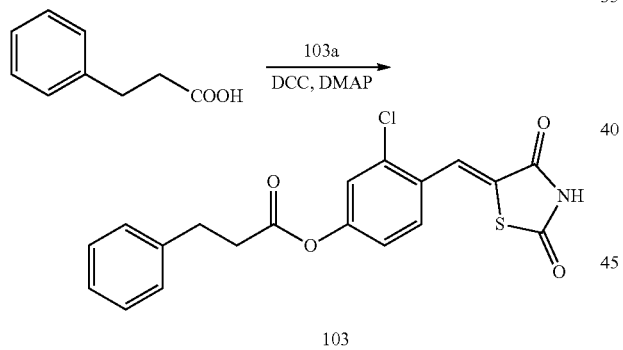

103

1 g (3.91 mmol) of 103a was added to a round-bottomed flask, and then, 0.587 g (3.91 mmol) of 3-phenylpropionic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 93.3%

1H NMR (300 MHz, DMSO-d6) δ12.77 (s, 1H), δ7.87 (s, 1H), δ7.62 (d, J=8.4 Hz, 1H), δ7.45 (d, J=2.19 Hz, 1H), δ7.34 (m, 6H), δ2.99 (m, 4H)

Example 104. Preparation of Compound 104 ((Z)-3-chloro-4-((2,4-dioxothiazolidin-5-ylidene)methyl)phenyl 4-phenylbutanoate)

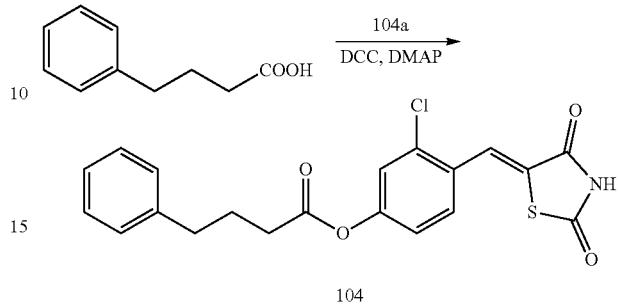

104

1 g (3.91 mmol) of 104a was added to a round-bottomed flask, and then, 0.642 g (3.91 mmol) of 4-phenylbutyric acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicydohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 88.8%

1H NMR (300 MHz, DMSO-d6) δ12.77 (s, 1H), δ7.88 (s, 1H), δ7.62 (d, J=8.79 Hz, 1H), δ7.54 (d, J=2.19 Hz, 1H), δ7.34 (m, 6H), δ2.70 (m, J=7.32 Hz, 4H), δ1.99 (m, J=7.32 Hz, 2H)

Example 105. Preparation of Compound 105 ((Z)-3-chloro-4-((2,4-dioxothiazolidin-5-ylidene)methyl)phenyl 5-phenylpentanoate)

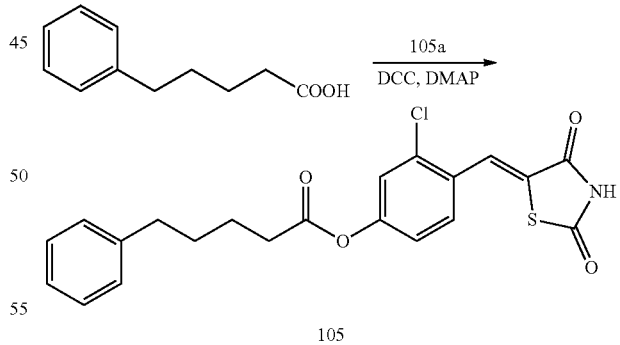

105

1 g (3.91 mmol) of 105a was added to a round-bottomed flask, and then, 0.697 g (3.91 mmol) of 5-phenylpentanoic acid and 0.04 g (0.33 mmol) of DMAP were added thereto, and then, the result was dissolved in dichloromethane (20 ml), followed by stirring in an ice bath. After 5 minutes, 0.742 g (3.60 mmol) of N, N'-dicyclohexylcarbodiimide (DCC) was added thereto and reacted at room temperature. When the reaction was completed, which was confirmed by TLC, the resulting urea in the form of solid was filtered under reduced pressure, and the filtrate was subjected to acid•base extraction and recrystallization, thereby obtaining pure solid.

Yield: 89.9%

1H NMR (300 MHz, DMSO-d6) δ12.77 (s, 1H), δ7.88 (s, 1H), δ7.62 (d, J=8.79 Hz, 1H), δ7.54 (d, J=2.19 Hz, 1H), δ7.33 (m, 6H), δ2.63 (m, 4H), δδ7 (m, 4H)

Experimental Example 1: Inhibitory Activity of Compounds 1 to 105 on 15-PGDH

In this experimental example, the 15-PGDH—inhibiting activity of Compounds 1 to 105 synthesized according to Examples 1 to 105 was analyzed.

(1) Expression and Purification of 15-PGDH

To confirm 15-PGDH inhibition capability of the compounds synthesized according to Examples 1 to 105, 15-PGDH was purified as follows. The 15-PGDH cDNA plasmid containing the BamHI of the pGEX-2T expression vector and EcoRI restriction enzyme sites was transfected into E. coli BL-21 LysS by using conventional methods used in the art. Then, the transfected cells were cultured in an LB medium (500 ml) containing 50 μg/ml of ampicillin at a temperature of 37° C. and at a rate of 220 rpm until the $OD_{600}$ reached 0.6. Then, isopropyl beta-D-thiogalactoxide (1 mM) was added and the cells were further cultured at the temperature of 25° C. for 12 hours. The cells were then centrifuged at the gravity of 4,000 g for 30 minutes at a temperature of 4° C. to collect a cell pellet. The cell pellet was dissolved in 20 ml of cell lysis buffer (containing 1×PBS buffer (pH 7.4): 1 mM EDTA and 0.1 mM DTT) and sonicated at a temperature of 4° C. for 14×10 s. The digested cells were centrifuged at the gravity of 4,000 g for 20 minutes at a temperature of 4° C. The supernatant was then slowly loaded onto a glutathione-sepharose 4B column equilibrated at a temperature of 4° C. with cell lysis buffer [containing 1×PBS buffer (pH 7.4), 1 mM EDTA, and 0.1 mM DTT]. Washing was performed thereon by using a dissolution buffer until the $OD_{280}$ reached 0.005 or less. Then, 15-PGDH was eluted from the glutathione-sepharose 4B column at room temperature for 5 minutes by using an elution buffer [containing 50 mM Tris-HCl (pH 8.0), 10 mM reduced glutathione, 1 mM EDTA, and 0.1 mM DTT). The concentration of the purified enzyme was measured, and the purification level thereof was confirmed by SDS-PAGE.

(2) Measurement of Activity of 15-PGDH Inhibitor

To confirm whether the compounds according to the present disclosure have an effect of inhibiting 15-PGDH, the NADH, which appears at the wavelength of 340 nm, of Compounds 1 to 105 purified in (1) nm was measured by using fluorescence spectra photometer. That is, the cells were treated with a solution including 50 mM Tris-HCl (pH 7.5), 0.1 mM DTT, 0.25 mM (NAD+), 10 μg of purified 15-PGDH enzyme, 21 μM $PGE_2$. and various concentrations (0.0001 μM to 64 μM) of the derivative compound according to the present disclosure. In this case, the total volume of the solution was 2 ml. Then, the absorbance of the reaction mixture was recorded at the wavelength of 340 nm. To measure the activity of the derivative compounds according to the present disclosure, which is an inhibitor of 15-PGDH, the average value of NADH absorbance at 340 nm at various concentrations was obtained from a standard curve. The results of the 15-PGDH inhibitory activity of the derivative compounds according to the present disclosure are shown in Tables 1 and 2 below. In Tables 1 and 2, $IC_{50}$ indicates a concentration at which the compound according to the present disclosure inhibits 50% of 15-PGDH activity.

As a result, it was confirmed that all of the compounds according to the present disclosure had an activity of inhibiting 15-PGDH as shown in Tables 1 and 2.

Experimental Example 2. Measurement of $PGE_2$ Concentration

A549 cells were subcultured in RPMI 1640 medium (containing+8% fetal bovine serum (FBS) and antibiotic-antimycotic (AA)) for one week, and then, inoculated in a 6-well plate at $2.5×10^5$ cells/mL ($5×10^5$ cells/well) and cultured for 24 hours in a 5% $CO_2$ incubator at a temperature of 37° C. A549 cells are adenocarcinomic human alveolar basal epithelial cells which are derived from lung tissues. When cells were grown to about 80% confluence, a 15-PGDH inhibitor in 1×PBS buffer was injected at a concentration of 5 μM. To compare the results, the same amount of 1×PBS buffer was injected into a negative control, and, the treated cells were cultured in 5% $CO_2$ incubator. After 12 hours, the medium was collected and the collected medium was assayed to measure $PGE_2$ concentration by using an ELISA Kit (Abcam) according to the manufacturer's instructions. The concentration may be expressed as an exact value by plotting the calibration curve by using the absorbance value after diluting the standard in the medium by concentration.

TABLE 1

| Compound | $IC_{50}$(μM) | Control (pg/mL) | PGE2 concentration (pg/ml) | Increment % |
|---|---|---|---|---|
| 1 | 2.0904 | 273.769 | 283.2688 | 3.47 |
| 2 | 0.7822 | 273.769 | 301.0364 | 9.96 |
| 3 | 0.1958 | 273.769 | 191.3645 | −30.1 |
| 4 | 0.0783 | 273.769 | 556.6271 | 103.32 |
| 5 | 0.0305 | 273.769 | 501.1889 | 83.07 |
| 6 | 0.1373 | 273.769 | 349.6304 | 27.71 |
| 7 | 0.0238 | 273.769 | 329.5084 | 20.36 |
| 8 | 0.0153 | 273.769 | 879.6746 | 221.32 |
| 9 | 0.0202 | 273.769 | 792.1232 | 189.34 |
| 10 | 0.0317 | 273.769 | 520.1337 | 89.99 |
| 11 | 0.0319 | 119.6754 | 25.94563 | −78.32 |
| 12 | 0.0635 | 119.6754 | 77.92065 | −34.89 |
| 13 | 0.0418 | 119.6754 | 139.2902 | 16.39 |
| 14 | 0.022 | 119.6754 | 586.3975 | 389.99 |
| 15 | 0.044 | 119.6754 | 220.3344 | 84.11 |
| 16 | 0.2201 | 253.0363 | 283.7043 | 12.12 |
| 17 | 0.1057 | 253.0363 | 395.597 | 56.34 |
| 18 | 0.05 | 253.0363 | 198.1274 | −21.7 |
| 19 | 0.0198 | 253.0363 | 232.5151 | −8.11 |
| 20 | 0.0158 | 253.0363 | 828.2384 | 227.32 |
| 21 | 0.0376 | 253.0363 | 411.1081 | 62.47 |
| 22 | 0.0206 | 253.0363 | 480.187 | 89.77 |
| 23 | 0.0166 | 253.0363 | 1040.03 | 311.02 |
| 24 | 0.0154 | 253.0363 | 1010.425 | 299.32 |
| 25 | 0.0263 | 253.0363 | 266.5484 | 5.34 |
| 26 | 0.0254 | 197.2043 | 175.2752 | −11.12 |
| 27 | 0.0406 | 197.2043 | 393.7184 | 99.65 |
| 28 | 0.0284 | 197.2043 | 572.5235 | 190.32 |
| 29 | 0.0145 | 197.2043 | 922.5414 | 367.81 |
| 30 | 0.0235 | 197.2043 | 280.7203 | 42.35 |
| 31 | 1.1039 | 197.2043 | 199.4327 | 1.13 |
| 32 | 1.1186 | 197.2043 | 316.7495 | 60.62 |
| 33 | 0.4936 | 197.2043 | 192.6292 | −2.32 |
| 34 | 0.0602 | 197.2043 | 57.64282 | −70.77 |
| 35 | 0.0234 | 197.2043 | 455.1278 | 130.79 |
| 36 | 0.2423 | 202.7598 | 408.196 | 101.32 |
| 37 | 0.0278 | 202.7598 | 382.9119 | 88.85 |
| 38 | 0.0173 | 202.7598 | 859.6813 | 323.99 |

TABLE 1-continued

| Compound | IC$_{50}$(μM) | Control (pg/mL) | PGE2 concentration (pg/ml) | Increment % |
|---|---|---|---|---|
| 39 | 0.0175 | 202.7598 | 649.318 | 220.24 |
| 40 | 0.0282 | 202.7598 | 218.7373 | 7.88 |
| 41 | 0.1507 | 202.7598 | 23.64179 | −88.34 |
| 42 | 0.0422 | 202.7598 | 400.7345 | 97.64 |
| 43 | 0.0286 | 202.7598 | 432.4258 | 113.27 |
| 44 | 0.0239 | 202.7598 | 810.6337 | 299.80 |
| 45 | 0.0389 | 202.7598 | 362.494 | 78.78 |
| 46 | 2.1723 | 273.9787 | 278.8555 | 1.78 |
| 47 | 1.6214 | 273.9787 | 185.1274 | −32.43 |
| 48 | 1.403 | 273.9787 | 211.539 | −22.79 |
| 49 | 0.1285 | 273.9787 | 299.5683 | 9.34 |
| 50 | 0.0290 | 273.9787 | 519.6554 | 89.67 |
| 51 | 0.549 | 273.9787 | 283.1296 | 3.34 |
| 52 | 0.0328 | 273.9787 | 223.32 | −18.49 |
| 53 | 0.0245 | 273.9787 | 792.73 | 189.34 |

TABLE 2

| Compound | IC$_{50}$(μM) | Control (pg/mL) | PGE$_2$ concentration (pg/ml) | Increment % |
|---|---|---|---|---|
| 54 | 0.0238 | 273.9787 | 828.9774 | 202.57 |
| 55 | 0.0344 | 273.9787 | 295.349 | 7.8 |
| 56 | 0.298 | 159.1332 | 108.7675 | −31.65 |
| 57 | 0.1185 | 159.1332 | 131.3485 | −17.46 |
| 58 | 0.0943 | 159.1332 | 171.8161 | 7.97 |
| 59 | 0.0439 | 159.1332 | 1081.055 | 579.34 |
| 60 | 0.0584 | 159.1332 | 300.5549 | 88.87 |
| 61 | 1.41 | 159.1332 | 0.04774 | −99.97 |
| 62 | 0.4307 | 159.1332 | 178.4361 | 12.13 |
| 63 | 0.1787 | 159.1332 | 237.6336 | 49.33 |
| 64 | 0.0521 | 159.1332 | 199.4576 | 25.34 |
| 65 | 0.0232 | 159.1332 | 284.8007 | 78.97 |
| 66 | 0.0888 | 129.1737 | 132.3901 | 2.49 |
| 67 | 0.0305 | 129.1737 | 139.9468 | 8.34 |
| 68 | 0.0184 | 129.1737 | 255.0535 | 97.45 |
| 69 | 0.0261 | 129.1737 | 302.8477 | 134.45 |
| 70 | 0.0504 | 129.1737 | 219.5565 | 69.97 |
| 71 | 0.1236 | 129.1737 | 53.76209 | −58.38 |
| 72 | 0.1083 | 129.1737 | 105.832 | −18.07 |
| 73 | 0.0544 | 129.1737 | 261.4347 | 102.39 |
| 74 | 0.0507 | 129.1737 | 164.9677 | 27.71 |
| 75 | 0.0921 | 129.1737 | 159.2841 | 23.31 |
| 76 | 0.5424 | 119.6754 | 123.6726 | 3.34 |
| 77 | 0.4818 | 119.6754 | 187.3399 | 56.54 |
| 78 | 0.0562 | 119.6754 | 39.10992 | −67.32 |
| 79 | 0.0428 | 119.6754 | 116.875 | −2.34 |
| 80 | 0.0347 | 119.6754 | 236.9453 | 97.99 |
| 81 | 0.0558 | 210.4123 | 232.1268 | 10.32 |
| 82 | 0.0327 | 210.4123 | 610.1325 | 189.97 |
| 83 | 0.0228 | 210.4123 | 634.0143 | 201.32 |
| 84 | 0.0225 | 210.4123 | 245.488 | 16.67 |
| 85 | 0.0256 | 210.4123 | 194.0212 | −7.79 |
| 86 | 0.0541 | 210.4123 | 184.9103 | −12.12 |
| 87 | 0.1049 | 210.4123 | 399.2994 | 89.77 |
| 88 | 0.0225 | 210.4123 | 449.1671 | 113.47 |
| 89 | 0.0251 | 210.4123 | 1048.274 | 398.2 |
| 90 | 0.046 | 210.4123 | 416.8478 | 98.11 |
| 91 | 1.0833 | 111.6575 | 106.5773 | −4.5498 |
| 92 | 0.2056 | 111.6575 | 47.25859 | −57.6754 |
| 93 | 0.0710 | 111.6575 | 114.9832 | 2.9785 |
| 94 | 0.0327 | 111.6575 | 220.1299 | 97.1474 |
| 95 | 0.0508 | 111.6575 | 238.3412 | 113.4574 |
| 96 | 0.0268 | 111.6575 | 121.5809 | 8.8874 |
| 97 | 0.0277 | 111.6575 | 120.703 | 8.1011 |
| 98 | 0.0324 | 111.6575 | 266.5808 | 138.7487 |
| 99 | 0.0392 | 111.6575 | 186.2131 | 66.7717 |
| 100 | 0.0394 | 111.6575 | 107.4803 | −3.7411 |
| 101 | 0.0451 | 111.6575 | 200.4108 | 79.4871 |
| 102 | 0.0753 | 111.6575 | 222.4242 | 99.2022 |
| 103 | 0.0875 | 111.6575 | 290.2972 | 159.989 |
| 104 | 0.0749 | 111.6575 | 349.9990 | 213.4577 |
| 105 | 0.1298 | 111.6575 | 211.5461 | 89.4598 |

Experimental Example 3. Wound Treatment Assay

HaCaT cells subcultured for about one week in DMEM [containing+8% FBS, AA] medium were inoculated in a 6-well plate at 2×10⁵ cells/mL (4×10 s cells/well). Then, the cells were cultured for about 24 hours until the cells reached 80% confluency. HaCaT cells are an adult human skin-derived and spontaneously transfected aneuploid immortal keratinocyte cell line. After the culture, the cells were washed with 1×PBS buffer and the used medium was replaced with an FBS and antibiotic-free medium. Then, mitomycin was added thereto at a concentration of 30 μg/mL and the cells were cultured for 2 hours. Then, the cells were washed with 1×PBS buffer, and a cell monolayer on the bottom surface of each well was scratched by using a 200 μL pipette tip to harm the cells. Since some cells were washed away by the scratching, the plate was washed repeatedly with 1×PBS buffer and then, filled with DMEM medium containing FBS and AA, and photographed at the time of 0 hour.

The 15-PGDH inhibitor was then injected at a concentration of 5 μM or the indicated concentration. For comparison with the results, in the case of the negative control, nothing was added, and in the case of the positive control, TGF-β1 was injected at a concentration of 1 ng/mL and then, the cells were cultured for 48 hours. After 48 hours, the picture of the cells was taken again to confirm how much the cells were grown due to the drug effect.

Figure 2:
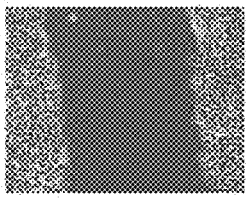
FIG. 2 shows images showing the wound treatment effect when Compounds 59 and 89 are used at a concentration of 5 µM.
Figure 2:
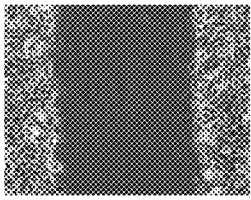
Figure 2:
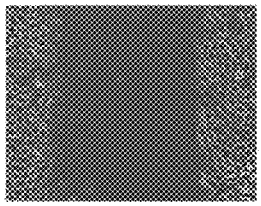
Figure 2:
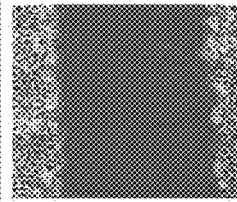
Figure 2:
Figure 2:
Figure 2:
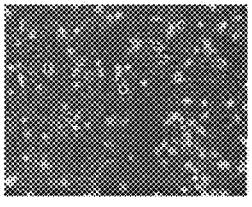
Figure 2:
Figure 3:
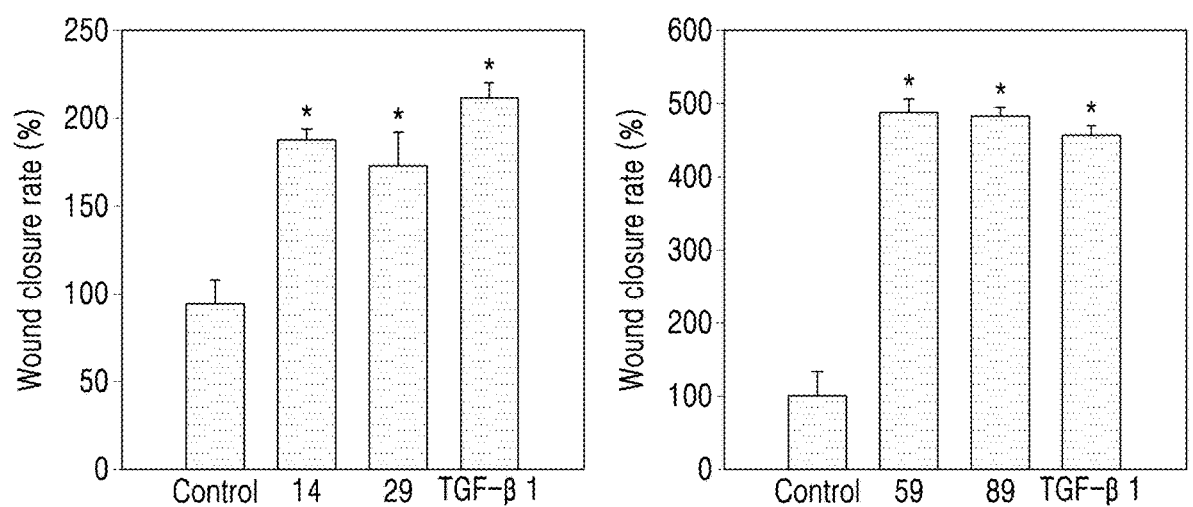
FIG. 3 illustrates a graph of a wound closure rate obtained from the results shown in FIGS. 1 and 2.
Figure 6:
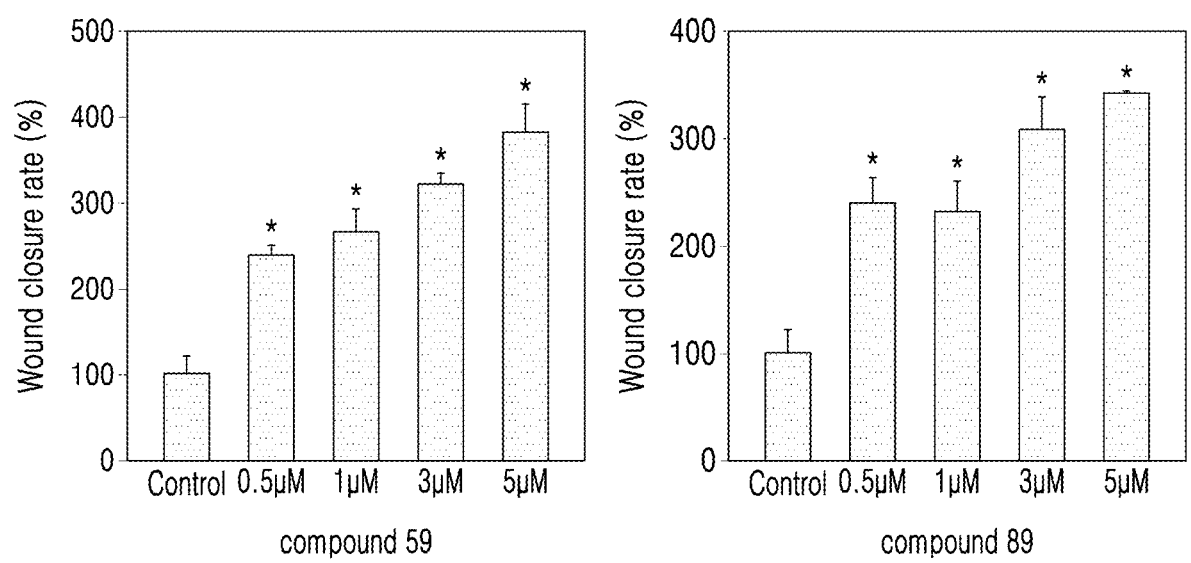
FIG. 6 illustrates a graph of a wound closure rate obtained from the results shown in FIGS. 4 and 5.

The results are shown in FIGS. 1 to 6. FIG. 1 shows images showing the wound treatment effect when Compounds 14 and 29 are used at a concentration of 5 μM. FIG. 2 shows images showing the wound treatment effect when Compounds 59 and 89 are used at a concentration of 5 μM. FIG. 3 illustrates a graph of a wound closure rate obtained from the results shown in FIGS. 1 and 2. In FIGS. 3 and 6, * represents P<0.05. As shown in FIGS. 1 to 3, Compounds 1, 14, 59, and 89 showed significantly higher wound closure rates than the control. FIG. 4 shows images showing the wound treatment effect of Compound 59 used at various concentrations, and FIG. 5 shows images showing the wound treatment effect of Compound 89 used at various concentrations. FIG. 6 illustrates a graph of a wound closure rate obtained from the results shown in FIGS. 4 and 5. As shown in FIGS. 4 to 6, Compound 59 and Compound 89 showed a significantly high wound closure rate at 0.5 μM to 5 μM compared to the control.

The invention claimed is:

1. A compound represented by any one of Formulae 1a and 1b or a pharmaceutically acceptable salt thereof:

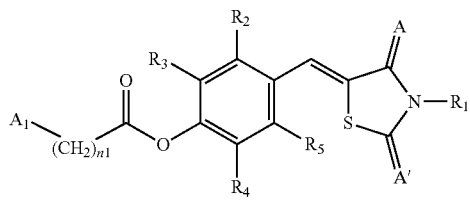

Formula 1a

-continued

Formula 1b

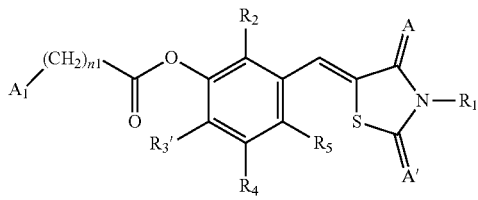

wherein, in Formulae 1a and 1b,
A and A' are O;
$A_1$ is a substituted or unsubstituted $C_3$-$C_{10}$ cycloalkyl group, or an unsubstituted $C_6$-$C_{20}$ aryl group;
$R_1$ is hydrogen or deuterium;
$R_2$, $R_3$ and $R_3'$ are each independently selected from hydrogen, deuterium, —F, —Cl, —Br, —I, and a substituted or unsubstituted $C_1$-$C_{10}$ alkoxy group;
$R_4$ and $R_5$ are each independently hydrogen or deuterium;
n1 is an integer from 1 to 10; and
at least one substituent of the substituted $C_1$-$C_{10}$ alkoxy group and the substituted $C_3$-$C_{10}$ cycloalkyl group is selected from deuterium, —F, —Cl, —Br, —I, —OH, a cyano group, a nitro group, an amino group, an amidino group, and a $C_1$-$C_{10}$ alkyl group.

2. The compound or pharmaceutically acceptable salt thereof of claim 1, wherein, in Formulae 1a and 1b, n1 is an integer from 1 to 6.

3. The compound or pharmaceutically acceptable salt thereof of claim 1, wherein the substituted or unsubstituted $C_1$-$C_{10}$ alkoxy group is an unsubstituted $C_1$-$C_6$ alkoxy group, the substituted or unsubstituted $C_3$-$C_{10}$ cycloalkyl group is an unsubstituted $C_3$-$C_{10}$ cycloalkyl group, and the unsubstituted $C_6$-$C_{20}$ aryl group is an unsubstituted $C_6$-$C_{12}$ aryl group.

4. The compound or pharmaceutically acceptable salt thereof of claim 2, wherein $A_1$ in Formulae 1a and 1b is selected from groups represented by Formulae 2-1 to 2-4, and 2-10:

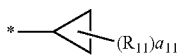
Formula 2-1

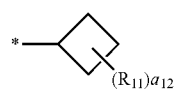
Formula 2-2

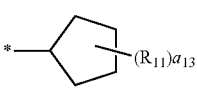
Formula 2-3

Formula 2-4

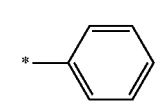
Formula 2-10 wherein, in Formulae 2-1 to 2-4, and 2-10, $R_{11}$ is selected from hydrogen, deuterium, —F, —Cl, —Br, —I, and a $C_1$-$C_{10}$ alkyl group, $a_{11}$ is an integer from 0 to 2, $a_{12}$ is an integer from 0 to 3, $a_{13}$ is an integer from 0 to 4, $a_{14}$ is an integer from 0 to 5, and * indicates a binding site to a neighboring atom.

5. The compound or pharmaceutically acceptable salt thereof of claim 4, wherein $R_{11}$ in Formulae 2-1 to 2-4 is hydrogen or deuterium.

6. The compound or pharmaceutically acceptable salt thereof of claim 2, wherein $A_1$ in Formulae 1a and 1b is selected from groups represented by Formulae 2-6 to 2-10:

*—△
Formula 2-6

*—□
Formula 2-7

*—⬠
Formula 2-8

*—⬡
Formula 2-9

*—⬡
Formula 2-10 wherein * in Formulae 2-6 to 2-10 indicates a binding site to a neighboring atom.

7. The compound or pharmaceutically acceptable salt thereof of a claim 1, being represented by one of Formulae 3-1 to 3-5:

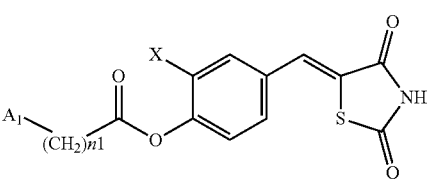
Formula 3-1

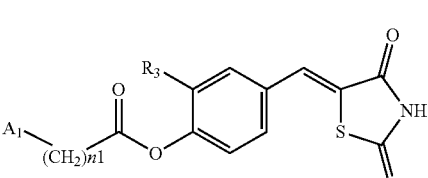
Formula 3-2

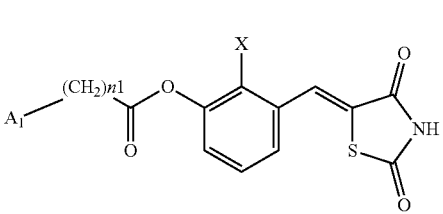
Formula 3-3

Formula 3-4

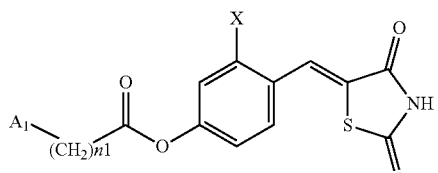

Formula 3-5

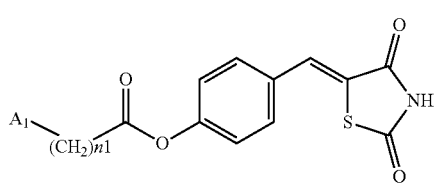

wherein, in Formulae 3-1 to 3-5, $A_1$ and n1 are the same as explained in connection with Formulae 1a and 1b, X is —F, —Cl, —Br, or —I, and $R_3$ is a substituted or unsubstituted $C_1$-$C_{10}$ alkoxy group.

8. The compound or pharmaceutically acceptable salt thereof of claim 7, wherein $A_1$ in Formulae 3-1 to 3-5 is selected from groups represented by Formulae 2-1 to 2-4, and 2-10:

Formula 2-1

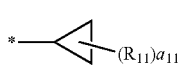

Formula 2-2

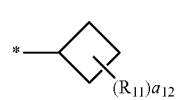

Formula 2-3

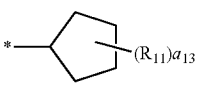

Formula 2-4

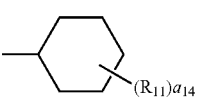

Formula 2-10

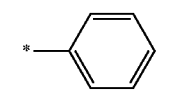

wherein $R_{11}$ in Formulae 2-1 to 2-4, is selected from hydrogen, deuterium, —F, —Cl, —Br, —I, and a $C_1$-$C_{10}$ alkyl group, $a_{11}$ is an integer from 0 to 2, a12 is an integer from 0 to 3, $a_{13}$ is an integer from 0 to 4, a14 is an integer from 0 to 5, and * indicates a binding site to a neighboring atom.

9. The compound or pharmaceutically acceptable salt thereof of claim 8, wherein $R_{11}$ in Formulae 2-1 to 2-4, is hydrogen or deuterium.

10. The compound or pharmaceutically acceptable salt thereof of claim 7, wherein $A_1$ in Formulae 3-1 to 3-5 is selected from groups represented by Formulae 2-6 to 2-10:

Formula 2-6

Formula 2-7

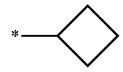

Formula 2-8

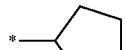

Formula 2-9

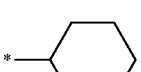

Formula 2-10

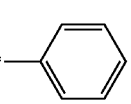

wherein* in Formulae 2-6 to 2-10 indicates a binding site to a neighboring atom.

11. The compound or pharmaceutically acceptable salt thereof of claim 7, wherein the compounds represented by Formulae 3-1 to 3-4 is any one of compounds represented by 3-6 to 3-11:

Formula 3-6

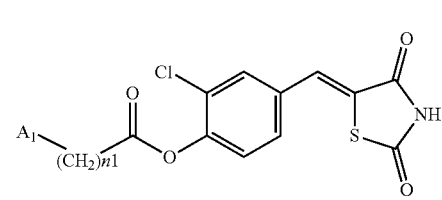

Formula 3-7

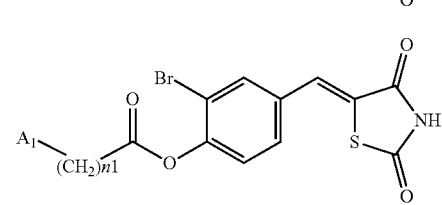

Formula 3-8

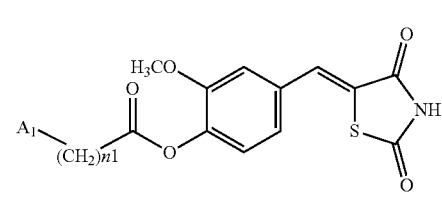

Formula 3-9

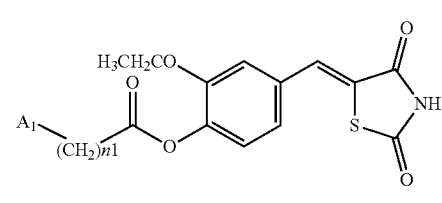

Formula 3-10

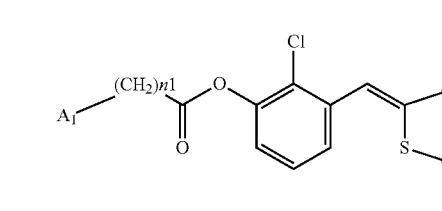

Formula 3-11
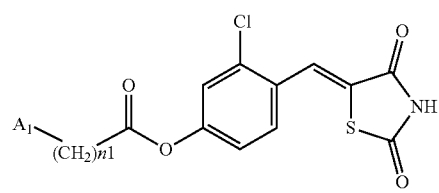
wherein A₁ and n1 in Formulae 3-6 to 3-11 are the same as explained in connection with Formulae 1a and 1b.
12. The compound or pharmaceutically acceptable salt thereof of claim 1, being selected from compounds represented by Formulae 4, 5, 7 to 10, 12 to 15, 19, 20, 22 to 25, 27 to 30, 34, 35, 37 to 40, 42 to 45, 49, 50, 52 to 55, 57 to 60, 64, 65, 67 to 70, 72 to 75, 79, 80, 82 to 85, 87 to 90, 94, 95, 97 to 100, and 102 to 105:
4
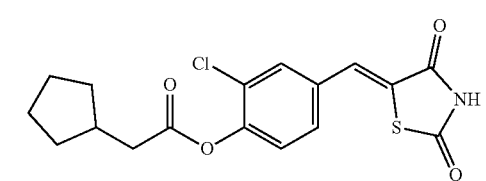
5
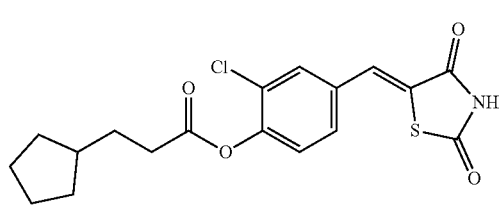
7
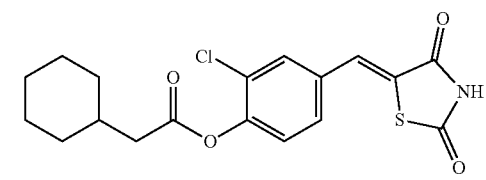
8
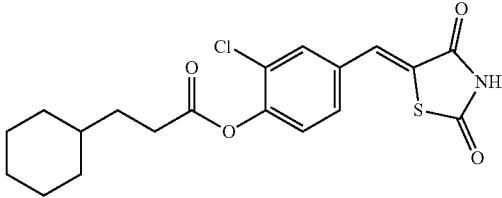
9
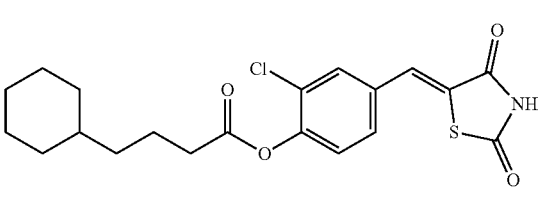
10
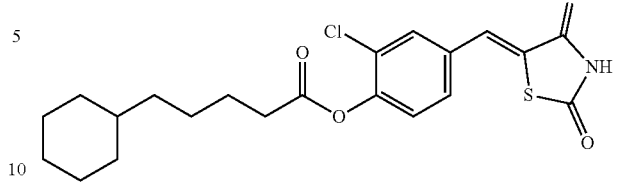
12
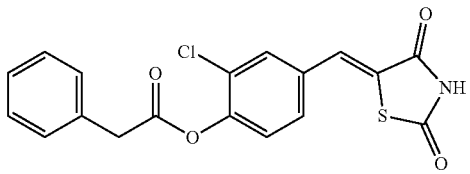
13
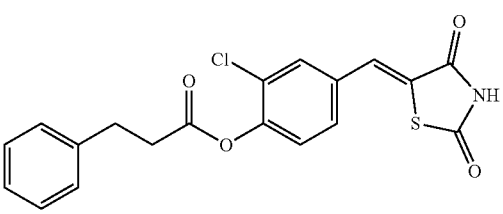
14
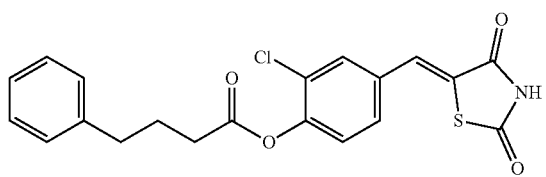
15
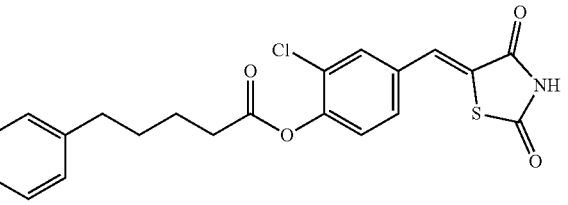
19
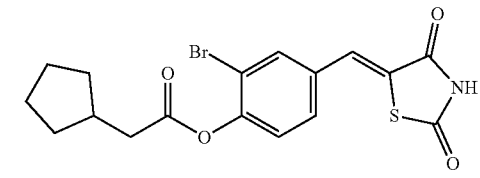
20
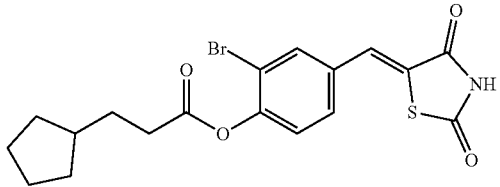
22
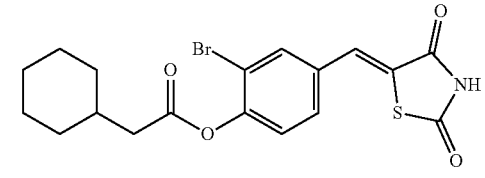

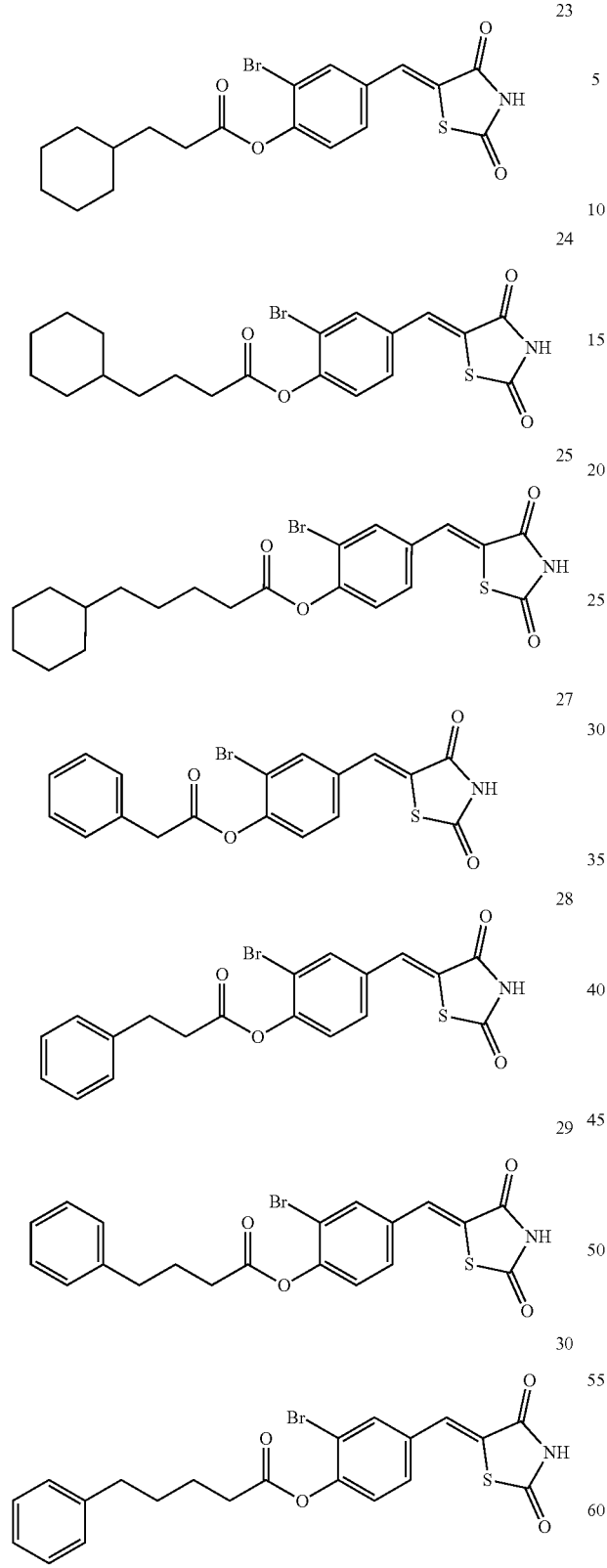
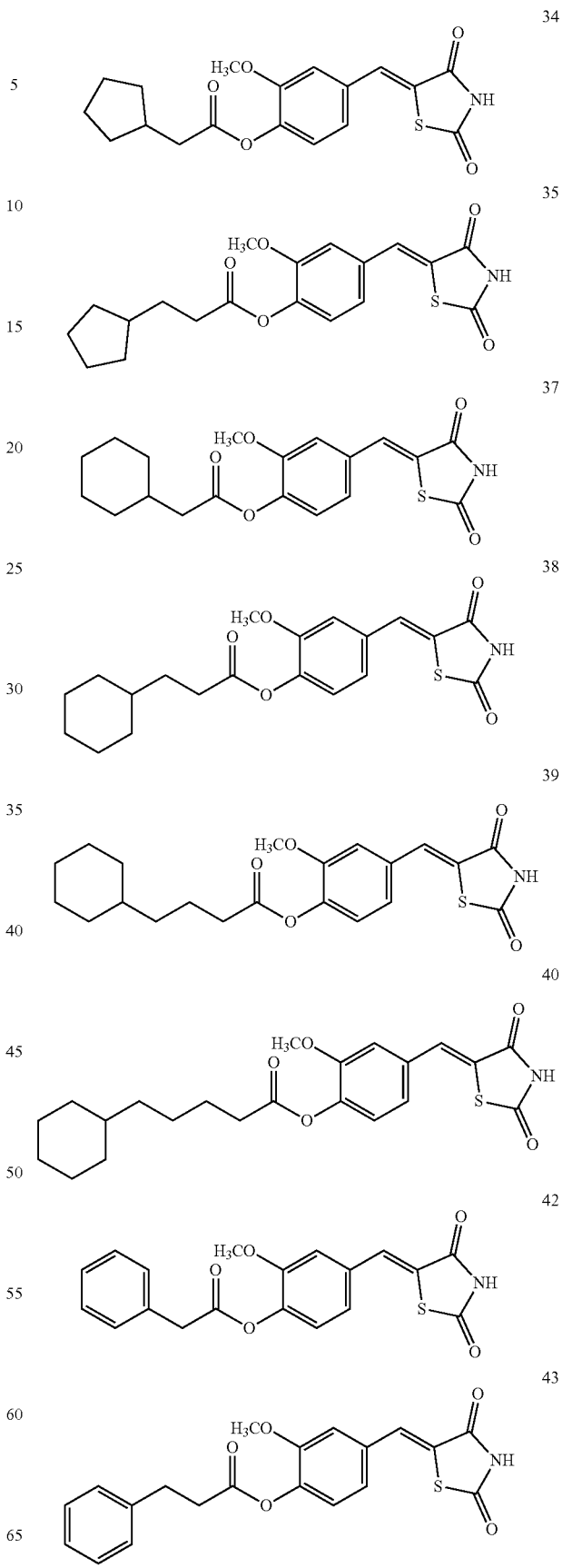

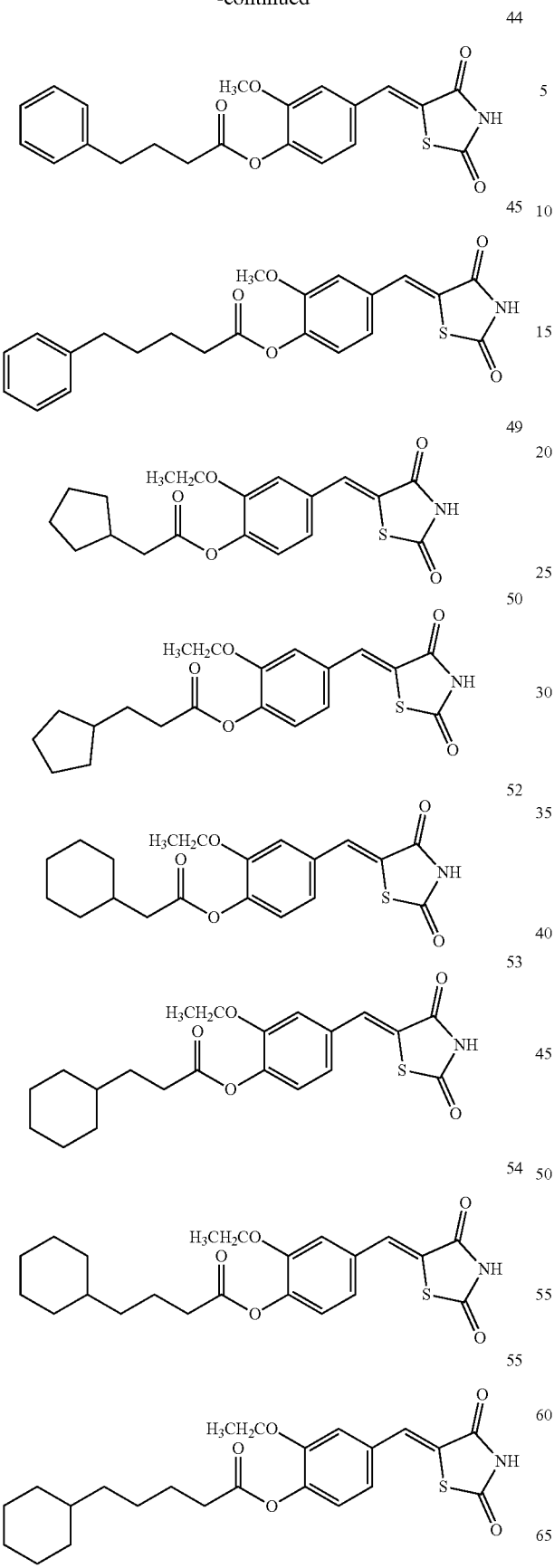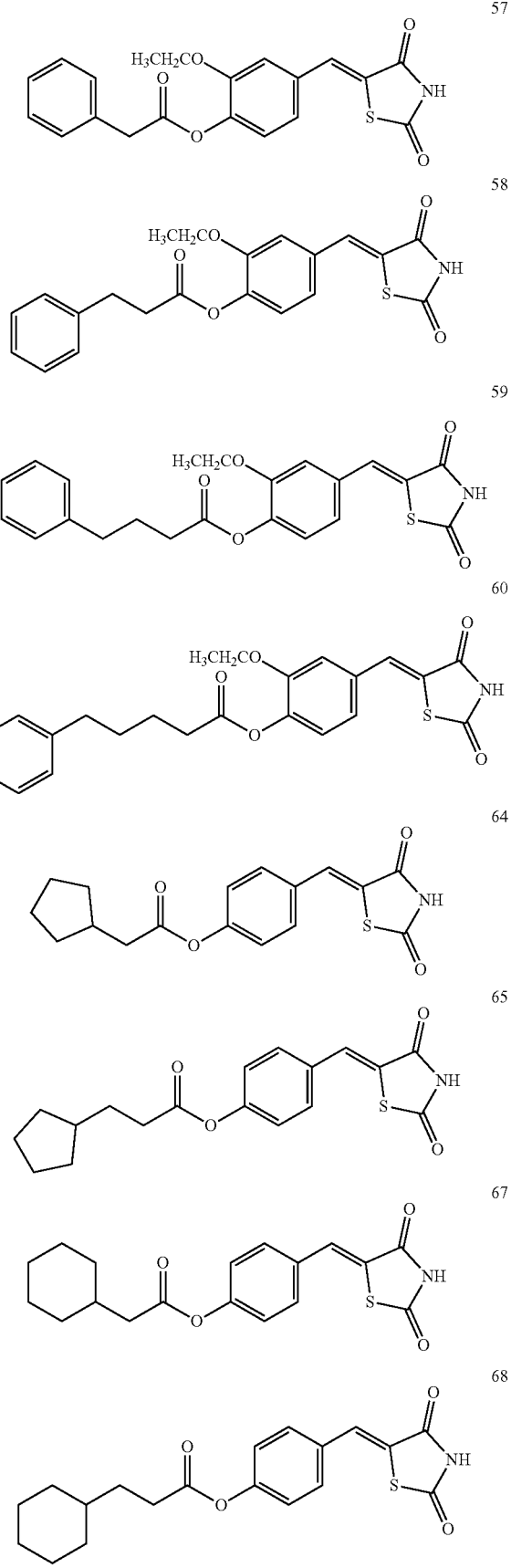

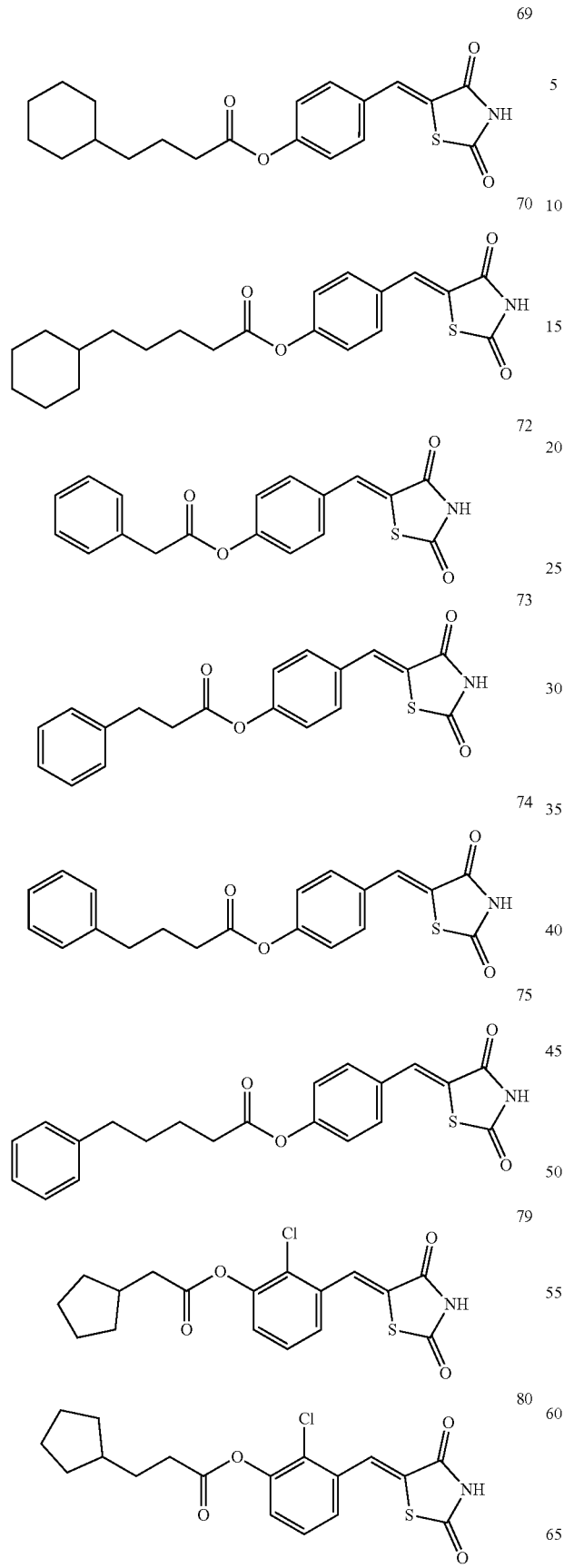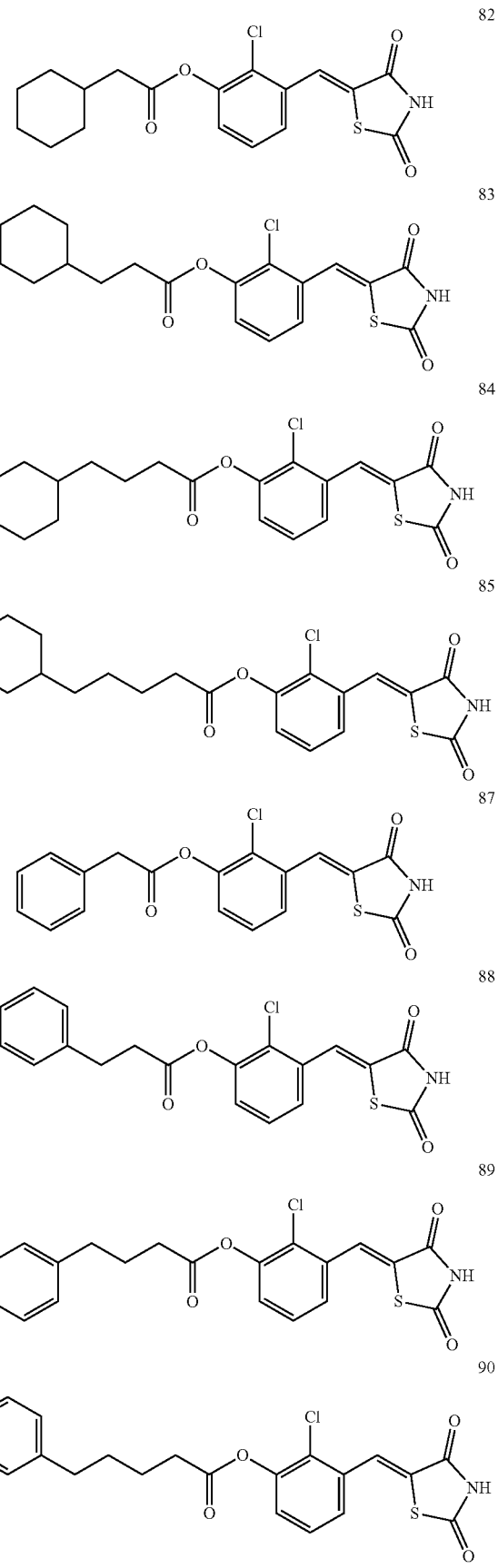

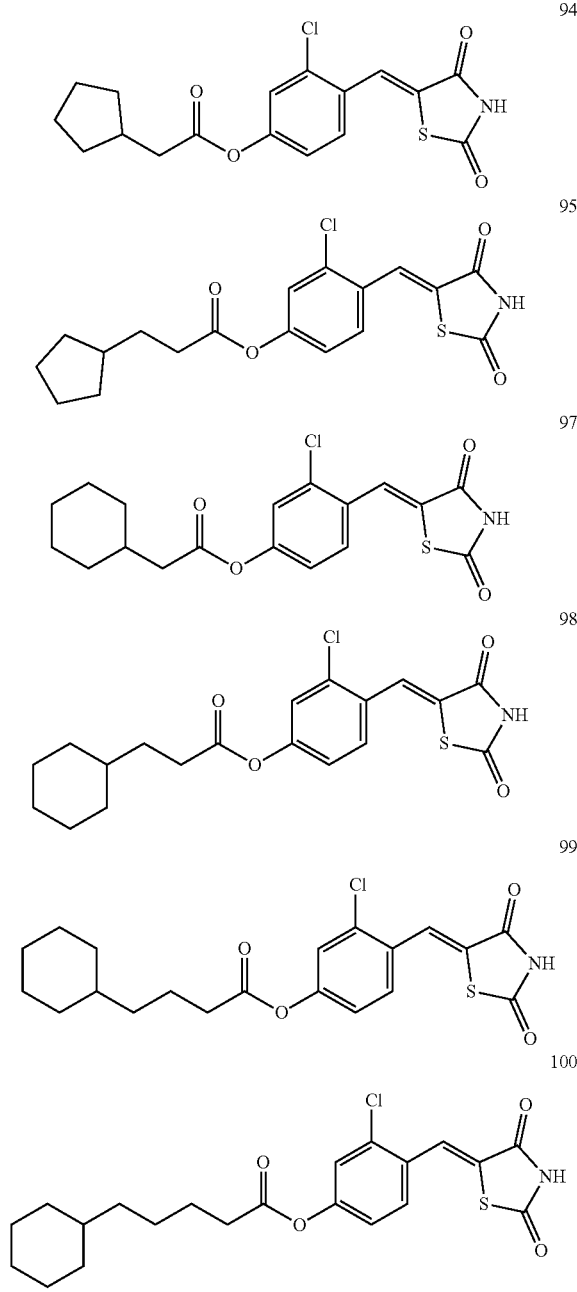

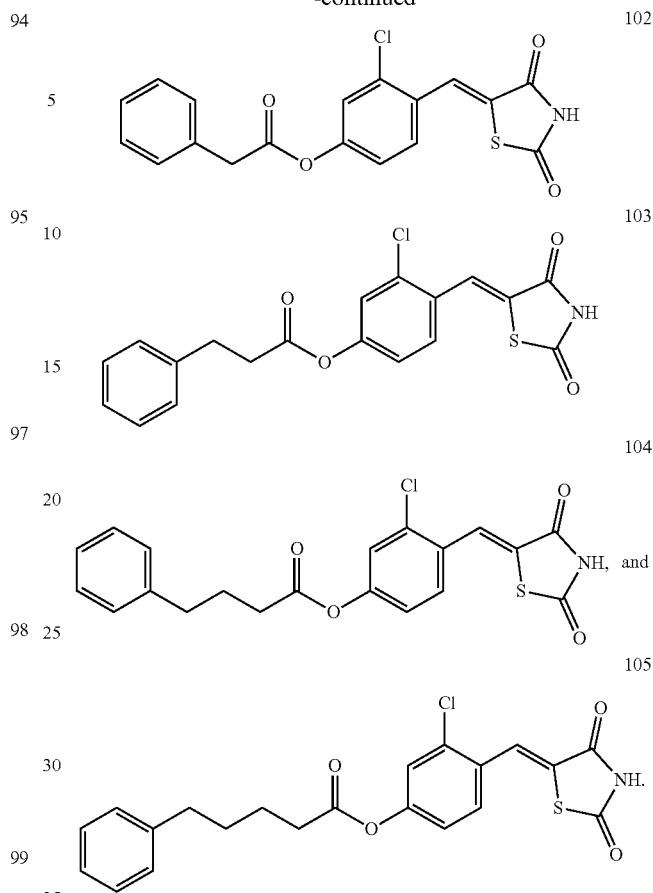

13. A pharmaceutical composition for increasing prostaglandin $E_2$, the pharmaceutical composition comprising the compound or pharmaceutically acceptable salt thereof of claim 1 as an active ingredient.

14. A method of increasing prostaglandin $E_2$ in a subject, the method including administering the compound or pharmaceutically acceptable salt thereof of claim 1 to the subject.

15. The method of claim 14, for preventing alopecia or promoting hair growth in a subject, treating cardiovascular diseases, gastrointestinal diseases, kidney diseases, atopy, burns or wounds, or promoting cell regeneration or bone formation.

\* \* \* \* \*